United States Patent
Mata et al.

(10) Patent No.: US 7,973,079 B2
(45) Date of Patent: Jul. 5, 2011

(54) METHODS AND COMPOUNDS FOR TREATING RETINOL-RELATED DISEASES

(75) Inventors: Nathan L. Mata, San Diego, CA (US); Kim B. Phan, San Diego, CA (US); Tam V. Bui, Laguna Niguel, CA (US); Mustapha Haddach, San Diego, CA (US)

(73) Assignee: Revision Therapeutics, Inc., San Diego, CA (US)

( * ) Notice: Subject to any disclaimer, the term of this patent is extended or adjusted under 35 U.S.C. 154(b) by 218 days.

(21) Appl. No.: 12/210,802

(22) Filed: Sep. 15, 2008

(65) Prior Publication Data

US 2009/0088435 A1   Apr. 2, 2009

Related U.S. Application Data

(60) Provisional application No. 60/975,765, filed on Sep. 27, 2007, provisional application No. 60/981,322, filed on Oct. 19, 2007.

(51) Int. Cl.
| | |
|---|---|
| *A61K 31/235* | (2006.01) |
| *A61K 31/165* | (2006.01) |
| *A61K 31/192* | (2006.01) |
| *A61K 31/197* | (2006.01) |
| *C07C 233/01* | (2006.01) |
| *C07C 233/58* | (2006.01) |
| *C07C 229/28* | (2006.01) |
| *C07C 31/08* | (2006.01) |
| *C07C 61/06* | (2006.01) |

(52) U.S. Cl. ........ 514/622; 514/619; 514/617; 514/532; 514/529; 562/507; 562/433; 564/163

(58) Field of Classification Search .................. 562/433, 562/507; 564/163; 514/617, 619, 622, 532, 514/529
See application file for complete search history.

(56) References Cited

U.S. PATENT DOCUMENTS

| 2,526,534 A | 10/1950 | Britton et al. |
| 4,255,152 A | 3/1981 | Hewitt et al. |
| 2006/0140953 A1 | 6/2006 | Newell et al. |

FOREIGN PATENT DOCUMENTS

| JP | 57-007480 A | 1/1982 |
| WO | WO 2005/092062 A2 * | 10/2005 |
| WO | WO 2005100301 A1 * | 10/2005 |
| WO | WO-2005-116010 A1 | 12/2005 |

OTHER PUBLICATIONS

Thornton et al. Eye 2005, 19, 935-944.*
http://www.mayoclinic.com/health/macular-degeneration/DS00284/DSECTION=treatments-and-drugs. Visited Jul. 26, 2010.*
Byrn et al., Chapter 11 Hydrates and Solvates in Solid-State Chemistry of Drugs (2nd Ed.), 1999, 233-247.*
Morissette et al. Adv. Drug Delivery Rev. 2004, 56, 275-300.*
A.M. Rouhi, Chem. & Eng. News, Feb. 24, 2003, 81(8), 32-35.*
Sandham et al. Bioorg. Med. Chem. Lett. 2007, 17, 4347-4350.*
Kryuchkova et al. Izvestiya Vysshikh Uchebnykh Zavedenii, Khimiya i Khimicheskaya Tekhnologiya 1974, 17(7), 1104-6 (Abstract and structures from CAPLUS provided).*
Nicola et al. Biochemical and Biophysical Research Communications 2007, 358(3), 686-691.*
Ulven et al. J. Med. Chem. 2006, 49, 6638-6641.*
Mohile et al., "Ionic liquids: efficient additives for *Candida rugosa* lipase-catalysed enantioselective hydrolysis of butyl 2-(4-chlorophenoxy)propionate," J. Mol. Catalysis B: Enzymatic 30:(5-6):185-188 (2004).
Motani, A. et al., "Identification and Characterization of a Non-Retinoid Ligand for Retinol-Binding Protein 4 Which Lowers Serum Retinol-Binding Protein 4 Levels In Vivo," JBC Papers in Press, pp. 1-16, Jan. 15, 2009, http://www.jbc.org/cgi/doi/10.1074/jbc.M809654200.
PCT/US08/76499 Search Report dated Mar. 24, 2009.
Science IP Search dated Jul. 13, 2006.
Science IP Search dated Sep. 10, 2007.
Supplementary EP Search Report and Written Opinion 08834564 dated Nov. 10, 2010.

* cited by examiner

*Primary Examiner* — Jason M Nolan

(74) *Attorney, Agent, or Firm* — Wilson Sonsini Goodrich & Rosati

(57) ABSTRACT

Compounds that reduce serum retinol levels are used to treat ophthalmic conditions associated with the overproduction of waste products that accumulate during the course of the visual cycle. We describe methods, compounds, and compositions to treat, for example, the macular degenerations and dystrophies or to alleviate symptoms associated with such ophthalmic conditions.

10 Claims, 11 Drawing Sheets

METHODS AND COMPOUNDS FOR TREATING RETINOL-RELATED DISEASES

CROSS REFERENCE TO RELATED APPLICATIONS

This application claims the benefit of U.S. Provisional Application No. 60/975,765 titled Methods and Compounds for Treating Retinol-Related Diseases, filed on Sep. 27, 2007, and U.S. Provisional Application No. 60/981,322 titled Methods and Compounds for Treating Retinol-Related Diseases, filed on Oct. 19, 2007, the disclosures of which are hereby incorporated by reference in their entirety.

FIELD OF THE INVENTION

The methods and compositions described herein are directed to the treatment of retinol-related diseases in a subject by modulating the activity or availability of serum retinol, retinol-binding protein (RBP) and/or transthyretin (TTR) in the subject.

BACKGROUND OF THE INVENTION

Retinoids are essential for maintenance of normal growth, development, immunity, reproduction, vision and other physiological processes. Conversely, abnormal production or processing of retinoids correlates with the manifestation of disease processes.

For example, more than 100 million of the world's children are vitamin-A deficient, causing blindness and death among these children. Excess vitamin-A levels in target organs and tissues, such as the eye, may also cause a variety of retinal diseases, including macular degeneration. A large variety of conditions, generally referred to as vitreoretinal diseases, can affect the vitreous and retina that lie on the back part of the eye, including the retinopathies and macular degenerations and dystrophies. Macular degeneration is a group of eye diseases that is the leading cause of blindness for those aged 55 and older in the United States, affecting more than 10 million Americans. Some studies predict a six-fold increase in the number of new cases of macular degeneration over the next decade, taking on the characteristics of an epidemic. Age-related macular degeneration or dystrophy, a particularly debilitating disease, leads to gradual loss of vision and eventually severe damage to the central vision.

There are two general categories of age-related macular degeneration: the wet and dry forms. Dry macular degeneration, which accounts for about 90 percent of all cases, is also known as atrophic, nonexudative, or drusenoid macular degeneration. With dry macular degeneration, drusen typically accumulates beneath the RPE tissue in the retina. Vision loss can then occur when drusen interfere with the function of photoreceptors in the macula. This form of macular degeneration results in the gradual loss of vision over many years.

Wet macular degeneration, which accounts for about 10 percent of cases, is also known as choroidal neovascularization, subretinal neovascularization, exudative, or disciform degeneration. In wet macular degeneration, abnormal blood vessel growth can form beneath the macula; these vessels can leak blood and fluid into the macula and damage photoreceptor cells. Studies have shown that the dry form of macular degeneration can lead to the wet form of macular degeneration. The wet form of macular degeneration can progress rapidly and cause severe damage to central vision.

SUMMARY OF THE INVENTION

Presented herein are methods, compounds, and compositions for the treatment of retinol-related diseases in a human subject or patient. Such diseases are macular degenerations, macular dystrophies and retinal dystrophies, including dry-form macular degenerations, geographic atrophy, and/or photoreceptor degeneration. Also presented herein are methods, compounds, and compositions for the treatment of hyperretinolemia (excess serum retinol levels) in a human subject or patient. Also presented herein are methods, compounds and compositions for lowering levels of serum retinol, a serum RBP (retinol binding protein), and/or a serum TTR (transthyretin) in a human subject or patient. Also presented herein are methods, compounds, and compositions for the treatment of vitreoretinal diseases such that the level of serum retinol in the body of a patient is lowered. In some embodiments, the vitreoretinal diseases are macular degenerations, macular dystrophies and retinal dystrophies. In some embodiment, the vitreoretinal diseases are dry form macular degeneration, photoreceptor degeneration, geographic atrophy, macular dystrophies, diabetic retinopathy, wet form of macular degeneration, retinopathy of prematurity, and/or retinitis pigmentosa.

In one aspect is a pharmaceutical composition comprising a compound of Formula (I):

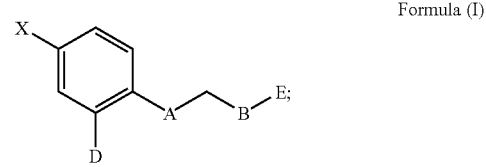

Formula (I)

wherein:

A is O, NH, or S;

B is a bond, —$(C_2$-$C_7)$alkyl, —$(C_2$-$C_7)$alkenyl, —$(C_3$-$C_8)$cycloalkyl, —$(C_2$-$C_7)$heteroalkyl, —$(C_3$-$C_8)$heterocycloalkyl, —$(C_3$-$C_8)$cycloalkenyl, —$(C_3$-$C_8)$heterocycloalkenyl;

D is isopropyl, isobutyl, sec-butyl, tert-butyl, neopentyl, sec-pentyl, isopentyl, cyclopropyl, cyclobutyl, cyclopentyl, methylenecyclopropyl, methylenecyclobutyl, methylenecyclopentyl;

E is (C=O)—OR, —O—(C=O)—R, —(C=O)—R, —OR, a carboxylic acid bioisostere, —(C=O)—$NR^1R$, $NR^1$—(C=O)—R, —$(C_1$-$C_7)$alkyl-(C=O)—OR, or —$(C_1$-$C_7)$alkyl-(C=O)—$NR^1R$;

R is H or

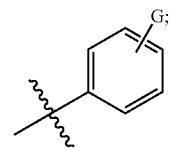

G is —$OR^1$, —$(C_1$-$C_6)$alkyl, —$(C_1$-$C_6)$alkyl-$OR^1$, halogen, —$CO_2R^1$, —$(C_1$-$C_6)$alkyl-$CO_2R^1$, $NHR^1$, —$(C_1$-$C_6)$alkyl-$NHR^1$, —(C=O)$NHR^1$, —$(C_1$-$C_6)$alkyl-(C=O)$NHR^1$, —$NHR^1$(C=O)$R^1$, —$(C_1$-$C_6)$alkyl-$NHR^1$(C=O)$R^1$;

$R^1$ is H or $(C_1$-$C_6)$alkyl;

X is a halogen;

or an active metabolite, or a pharmaceutically acceptable prodrug, salt, or solvate thereof, and a pharmaceutically acceptable excipient. In one embodiment, the pharmaceutical composition is an oral pharmaceutical composition for systemic administration of the compound of Formula (I).

In one embodiment is a pharmaceutical composition comprising a compound having the structure of Formula (II):

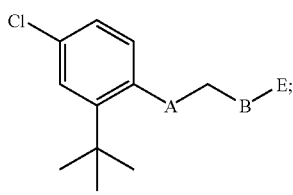

Formula (II)

wherein:

A is O, NH, or S;

B is a bond, —($C_2$-$C_7$)alkyl, —($C_2$-$C_7$)alkenyl, —($C_3$-$C_8$) cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;

E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;

R is H or

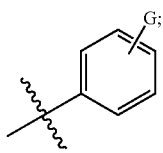

G is —$OR^1$, —($C_1$-$C_6$)alkyl, —($C_1$-$C_6$)alkyl-$OR^1$, halogen, —$CO_2R^1$, —($C_1$-$C_6$)alkyl-$CO_2R^1$, $NHR^1$, —($C_1$-$C_6$)alkyl-$NHR^1$, —(C=O)$NHR^1$, —($C_1$-$C_6$)alkyl-(C=O)$NHR^1$, —$NHR^1$(C=O)$R^1$—($C_1$-$C_6$)alkyl-$NHR^1$(C=O)$R^1$;

$R^1$ is H or ($C_1$-$C_6$)alkyl;

or an active metabolite, or a pharmaceutically acceptable prodrug, salt, or solvate thereof, and a pharmaceutically acceptable excipient. In one embodiment, the pharmaceutical composition is an oral pharmaceutical composition for systemic administration of the compound of Formula (II).

In another embodiment is a pharmaceutical composition comprising a compound having the structure of Formula (II) wherein A is O. In a further embodiment is a pharmaceutical composition comprising a compound having the structure of Formula (II) wherein B is —($CH_2$), and n is 1-6, or B is —($C_3$-$C_8$)cycloalkyl. In yet a further embodiment is a pharmaceutical composition comprising a compound having the structure of Formula (II) wherein E is (C=O)—OR, a carboxylic acid bioisostere, —(C=O)—$NR^1R$, —($C_1$-$C_7$) alkyl-(C=O)—OR, or —($C_1$-$C_7$)alkyl-(C=O)—$NR^1R$. In one embodiment is a pharmaceutical composition comprising a compound having the structure of Formula (II) wherein A is O, B is ($C_3$-$C_8$)cycloalkyl, E is (C=O)—OR, and R is H. In a further embodiment, B is cyclohexyl, and R is H. In yet a further embodiment, B is cyclopentyl and R is H. In yet a further embodiment, is a compound having the structure

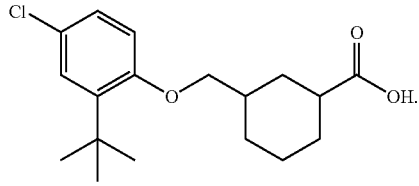

In another embodiment is a compound having the structure

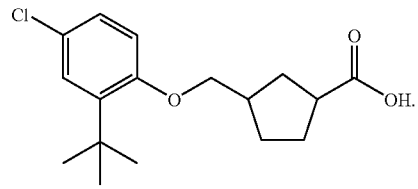

In one embodiment is a pharmaceutical composition comprising a compound having the structure of Formula (II) wherein R is

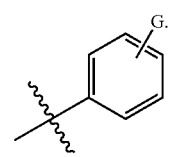

In another embodiment is a pharmaceutical composition comprising a compound having the structure of Formula (II) wherein E is (C=O)—OR. In a further embodiment is a pharmaceutical composition comprising a compound having the structure of Formula (II) wherein R is H. In yet a further embodiment is a composition comprising a compound of Formula (I) selected from the group consisting of: 5-(2-tert-butyl-4-chlorophenoxy)-N-(4-hydroxyphenyl)pentanamide, 7-(2-tert-butyl-4-chlorophenoxy)-N-(4-hydroxyphenyl)heptanamide, 4-(5-(2-tert-butyl-4-chlorophenoxy)pentanamido) benzoic acid, 4-(3-((2-tert-butyl-4-chlorophenoxy)methyl) cyclopentanamido)benzoic acid, 5-(2-tert-butyl-4-chlorophenoxy)pentanoic acid, 4-(2-tert-butyl-4-chlorophenoxy)butanoic acid, 2-(3-((2-tert-butyl-4-chlorophenoxy)methyl)cyclopentyl)acetic acid, 7-(2-tert-butyl-4-chlorophenoxy)heptanoic acid, 4-(5-(2-tert-butyl-4-chlorophenoxy)pentanamido)benzamide, 3-((2-tert-butyl-4-chlorophenoxy)methyl)cyclohexanecarboxylic acid, 3-((2-tert-butyl-4-chlorophenoxy)methyl)cyclopentanecarboxylic acid, 3-((2-tert-butyl-4-chlorophenylamino)methyl)cyclopentanamide, 4-(3-((2-tert-butyl-4-chlorophenoxy)methyl) cyclopentanecarboxamido)benzoic acid, and 5-(2-tert-butyl-4-chlorophenylthio)pentanoic acid In one embodiment is a pharmaceutical composition comprising a compound of Formula (I) that inhibits retinol-retinol binding protein-transthyretin complex formation wherein the $IC_{50}$ of the inhibition is less than about 5 μM. In a further embodiment is a pharmaceutical composition comprising a compound of Formula (I) wherein the $IC_{50}$ of the inhibition is less than about 1 μM. In another embodiment is a pharmaceutical composition comprising a compound of Formula (I) that inhibits cytochrome $P_{450}$ to less than about 50%. In yet a further embodiment is a pharmaceutical composition comprising a compound of Formula (I) that inhibits cytochrome P450 to less than about 10%. In yet another embodiment is a pharmaceutical composition comprising a compound of Formula (I) wherein the compound of Formula (I) is used for the treatment of a vitreoretinal disease. In a further embodiment is a pharmaceutical composition comprising a compound of Formula (I) wherein the vitreoretinal disease is selected from the group consisting of: dry form macular degeneration, photoreceptor degeneration, geographic atrophy, macular dystrophies, diabetic retinopathy, wet form of macular degeneration, retinopathy of prematurity, and retinitis pigmentosa.

In one aspect is a pharmaceutical composition comprising a compound of Formula (I):

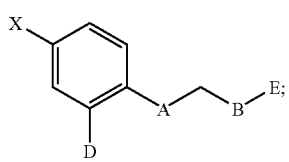

Formula (I)

wherein:
A is O, NH, or S;
B is a bond, —($C_2$-$C_7$)alkyl, —($C_2$-$C_7$)alkenyl, —($C_3$-$C_8$) cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;
D is isopropyl, isobutyl, sec-butyl, tert-butyl, neopentyl, sec-pentyl, isopentyl, cyclopropyl, cyclobutyl, cyclopentyl, methylenecyclopropyl, methylenecyclobutyl, methylenecyclopentyl;
E is (C═O)—OR, —O—(C═O)—R, —(C═O)—R, —OR, a carboxylic acid bioisostere, —(C═O)—$NR^1R$, $NR^1$—(C═O)—R, —($C_1$-$C_7$)alkyl-(C═O)—OR, or —($C_1$-$C_7$)alkyl-(C═O)—$NR^1R$;
R is H, an optionally substituted aryl, or an optionally substituted heteroaryl;
X is a halogen;
or an active metabolite, or a pharmaceutically acceptable prodrug, salt, or solvate thereof; and a pharmaceutically acceptable excipient or carrier. In one embodiment, the pharmaceutical composition is an oral pharmaceutical composition for systemic administration of the compound of Formula (I).

In one embodiment is a pharmaceutical composition comprising a compound having the structure of Formula (II):

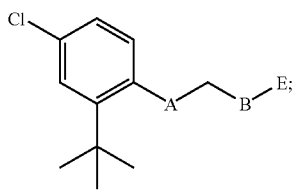

Formula (II)

wherein:
A is O, NH, or S;
B is a bond, —($C_2$-$C_7$)alkyl, —($C_2$-$C_7$)alkenyl, —($C_3$-$C_8$) cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;
E is (C═O)—OR, —O—(C═O)—R, —(C═O)—R, —OR, a carboxylic acid bioisostere, —(C═O)— $NR^1R$, $NR^1$—(C═O)—R, —($C_1$-$C_7$)alkyl-(C═O)— OR, or —($C_1$-$C_7$)alkyl-(C═O)—$NR^1R$;
R is H, an optionally substituted aryl, or an optionally substituted heteroaryl;
or an active metabolite, or a pharmaceutically acceptable prodrug, salt, or solvate thereof, and a pharmaceutically acceptable excipient or carrier. In one embodiment, the pharmaceutical composition is an oral pharmaceutical composition for systemic administration of the compound of Formula (II).

In one embodiment is a pharmaceutical composition comprising a compound having the structure of Formula (II) wherein A is O, B is ($C_3$-$C_8$)cycloalkyl, E is (C═O)—OR, and R is H; or an active metabolite, or a pharmaceutically acceptable prodrug, salt, or solvate thereof, and a pharmaceutically acceptable excipient or carrier. In a further embodiment, is a pharmaceutical composition comprising a compound having the structure of Formula (II) wherein A is O, B is cyclohexyl, and R is H; or an active metabolite, or a pharmaceutically acceptable prodrug, salt, or solvate thereof, and a pharmaceutically acceptable excipient or carrier. In yet a further embodiment, is a pharmaceutical composition comprising a compound having the structure of Formula (II) wherein A is O, B is cyclopentyl and R is H; or an active metabolite, or a pharmaceutically acceptable prodrug, salt, or solvate thereof, and a pharmaceutically acceptable excipient or carrier. In yet a further embodiment is a pharmaceutical composition comprising a compound having the structure

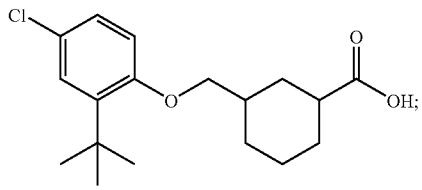

or an active metabolite, or a pharmaceutically acceptable prodrug, salt, or solvate thereof, and a pharmaceutically acceptable excipient or carrier. In another embodiment is a pharmaceutical composition comprising a compound having the structure

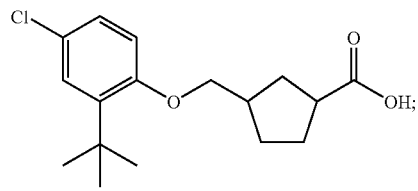

or an active metabolite, or a pharmaceutically acceptable prodrug, salt, or solvate thereof, and a pharmaceutically acceptable excipient or carrier.

In another embodiment is a pharmaceutical composition comprising a compound of Formula (I) wherein the composition is in an amount sufficient to modulate the serum retinol or ocular tissue retinol level or activity in a mammal.

In one aspect is a method of treating dry form macular degeneration, photoreceptor degeneration, geographic atrophy, macular dystrophies, diabetic retinopathy, wet form of macular degeneration, retinopathy of prematurity, or retinitis pigmentosa in a patient in need, comprising administering to the patient a therapeutically effective amount of a compound of Formula (I):

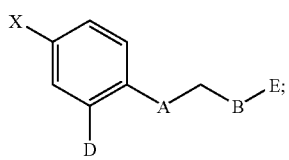

Formula (I)

wherein:
A is O, NH, or S;
B is a bond, —($C_2$-$C_7$)alkyl, —($C_2$-$C_7$)alkenyl, —($C_3$-$C_8$)cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;
D is isopropyl, isobutyl, sec-butyl, tert-butyl, cyclopropyl, cyclobutyl, cyclopentyl, methylenecyclopropyl, methylenecyclobutyl, methylenecyclopentyl;
E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;
R is H, an optionally substituted aryl, an optionally substituted heterocycloalkyl, or an optionally substituted heteroaryl;
X is a halogen;
or an active metabolite, or a pharmaceutically acceptable prodrug, salt, or solvate thereof. In one embodiment, the therapeutically effective amount of a compound of Formula (I) is provided in the form of an oral pharmaceutical composition for systemic administration of the compound.

In one embodiment is a method of treating dry form macular degeneration, photoreceptor degeneration, geographic atrophy, macular dystrophies, diabetic retinopathy, wet form of macular degeneration, retinopathy of prematurity, and retinitis pigmentosa in a patient in need, comprising administering to the patient a therapeutically effective amount of a compound of Formula (II):

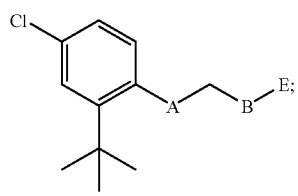

Formula (II)

wherein:
A is O, NH, or S;
B is a bond, —($C_2$-$C_7$)alkyl, —($C_2$-$C_7$)alkenyl, —($C_3$-$C_8$)cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;
E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;
R is H, an optionally substituted aryl, an optionally substituted heterocycloalkyl, or an optionally substituted heteroaryl;
or an active metabolite, or a pharmaceutically acceptable prodrug, salt, or solvate thereof. In one embodiment, the therapeutically effective amount of a compound of Formula (II) is provided in the form of an oral pharmaceutical composition for systemic administration of the compound.

In one aspect is a method of treating a vitreoretinal disease, comprising administering to a mammal a therapeutically effective amount of a compound of Formula (I):

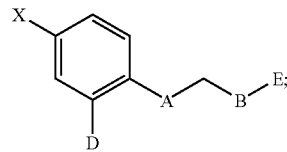

Formula (I)

wherein:
A is O, NH, or S;
B is a bond, —($C_2$-$C_7$)alkyl, —($C_2$-$C_7$)alkenyl, —($C_3$-$C_8$)cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;
D is isopropyl, isobutyl, sec-butyl, tert-butyl, cyclopropyl, cyclobutyl, cyclopentyl, methylenecyclopropyl, methylenecyclobutyl, methylenecyclopentyl;
E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;
R is H, an optionally substituted aryl, an optionally substituted heterocycloalkyl, or an optionally substituted heteroaryl;
X is a halogen;
or an active metabolite, or a pharmaceutically acceptable prodrug, salt, or solvate thereof,
wherein the compound of Formula (I) modulates a retinol binding protein level or activity in the mammal. In one embodiment, the therapeutically effective amount of a compound of Formula (I) is provided in the form of an oral pharmaceutical composition for systemic administration of the compound.

In one embodiment is a method of treating a vitreoretinal disease comprising administering to a mammal a therapeutically effective amount of a compound of Formula (II):

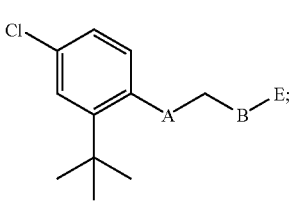

Formula (II)

wherein:
A is O, NH, or S;
B is a bond, —($C_2$-$C_7$)alkyl, —($C_2$-$C_7$)alkenyl, —($C_3$-$C_8$)cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;
E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;
R is H, an optionally substituted aryl, an optionally substituted heterocycloalkyl, or an optionally substituted heteroaryl;
or an active metabolite, or a pharmaceutically acceptable prodrug, salt, or solvate thereof, wherein the compound of Formula (I) modulates a retinol binding protein level or activity in the mammal. In one embodiment, the therapeutically effective amount of a compound of Formula (II) is provided in the form of an oral pharmaceutical composition for systemic administration of the compound.

In another embodiment is a method of treating a vitreoretinal disease comprising administering to a mammal a therapeutically effective amount of a compound of Formula (I) or (II) wherein the retinol binding protein is RBP4. In a further embodiment is a method of treating a vitreoretinal disease comprising administering to a mammal a therapeutically effective amount of a compound of Formula (I) or (II) wherein the vitreoretinal disease is dry form macular degeneration, photoreceptor degeneration, geographic atrophy, macular dystrophies, diabetic retinopathy, wet form of macular degeneration, retinopathy of prematurity, and retinitis pigmentosa.

In one aspect is a method of lowering serum retinol binding protein or transthyretin levels or activity in a mammal, comprising administering a therapeutically effective amount of a compound of Formula (I):

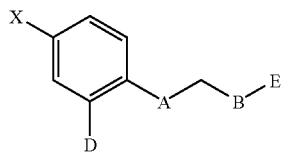

Formula (I)

wherein:

A is O, NH, or S;

B is a bond, —(C$_2$-C$_7$)alkyl, —(C$_2$-C$_7$)alkenyl, —(C$_3$-C$_8$)cycloalkyl, —(C$_2$-C$_7$)heteroalkyl, —(C$_3$-C$_8$)heterocycloalkyl, —(C$_3$-C$_8$)cycloalkenyl, —(C$_3$-C$_8$)heterocycloalkenyl;

D is isopropyl, isobutyl, sec-butyl, tert-butyl, cyclopropyl, cyclobutyl, cyclopentyl, methylenecyclopropyl, methylenecyclobutyl, methylenecyclopentyl;

E is (C=O)—OR, —O—(C=O)—R, —(C=O)—R, —OR, a carboxylic acid bioisostere, —(C=O)—NR$^1$R, NR$^1$—(C=O)—R, —(C$_1$-C$_7$)alkyl-(C=O)—OR, or —(C$_1$-C$_7$)alkyl-(C=O)—NR$^1$R;

R is H, an optionally substituted aryl, an optionally substituted heterocycloalkyl, or an optionally substituted heteroaryl;

X is a halogen;

or an active metabolite, or a pharmaceutically acceptable prodrug, salt, or solvate thereof, wherein the compound of Formula (I) modulates a serum retinol binding protein or transthyretin level or activity in the mammal. In one embodiment, the therapeutically effective amount of a compound of Formula (I) is provided in the form of an oral pharmaceutical composition for systemic administration of the compound.

In one aspect is a method of lowering serum retinol binding protein or transthyretin levels or activity in a mammal comprising administering a therapeutically effective amount of a compound of Formula (II):

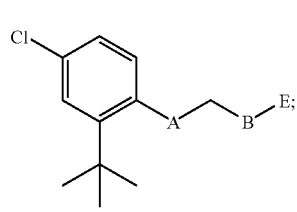

Formula (II)

wherein:

A is O, NH, or S;

B is a bond, —(C$_2$-C$_7$)alkyl, —(C$_2$-C$_7$)alkenyl, —(C$_3$-C$_8$)cycloalkyl, —(C$_2$-C$_7$)heteroalkyl, —(C$_3$-C$_8$)heterocycloalkyl, —(C$_3$-C$_8$)cycloalkenyl, —(C$_3$-C$_8$)heterocycloalkenyl;

E is (C=O)—OR, —O—(C=O)—R, —(C=O)—R, —OR, a carboxylic acid bioisostere, —(C=O)—NR$^1$R, NR$^1$—(C=O)—R, —(C$_1$-C$_7$)alkyl-(C=O)—OR, or —(C$_1$-C$_7$)alkyl-(C=O)—NR$^1$R;

R is H, an optionally substituted aryl, an optionally substituted heterocycloalkyl, or an optionally substituted heteroaryl;

or an active metabolite, or a pharmaceutically acceptable prodrug, salt, or solvate thereof, wherein the compound of Formula (II) modulates a serum retinol binding protein or transthyretin level or activity in the mammal. In one embodiment, the therapeutically effective amount of a compound of Formula (II) is provided in the form of an oral pharmaceutical composition for systemic administration of the compound.

In yet a further embodiment is a method of lowering a serum retinol binding protein or transthyretin level or activity in a mammal comprising administering a therapeutically effective amount of a compound of Formula (I) or (II) wherein the serum retinol binding protein is RBP4. In one embodiment is a method of lowering serum retinol binding protein or transthyretin levels or activity in a mammal comprising administering a therapeutically effective amount of a compound of Formula (I) or (II) wherein the compound of Formula (I) or (II) inhibits transcription of retinol binding protein or transthyretin in the mammal. In a further embodiment is a method of lowering serum retinol binding protein or transthyretin levels or activity in a mammal comprising administering a therapeutically effective amount of a compound of Formula (I) or (II) wherein the compound of Formula (I) or (II) inhibits translation of retinol binding protein or transthyretin in the mammal. In yet another embodiment is a method of lowering serum retinol binding protein or transthyretin levels or activity in a mammal comprising administering a therapeutically effective amount of a compound of Formula (I) or (II) wherein the compound of Formula (I) or (II) inhibits the binding of retinol to retinol binding protein. In one embodiment is a method of lowering serum retinol binding protein or transthyretin levels or activity in a mammal comprising administering a therapeutically effective amount of a compound of Formula (I) or (II) wherein the compound of Formula (I) or (II) inhibits the binding of retinol binding protein to transthyretin. In another embodiment is a method of lowering serum retinol binding protein or transthyretin levels or activity in a mammal comprising administering a therapeutically effective amount of a compound of Formula (I) or (II) wherein the compound of Formula (I) or (II) increases retinol binding protein or transthyretin clearance in the mammal.

In one aspect is a method for treating a retinol-related disease in a mammal, comprising administering to the mammal a therapeutically effective amount of a compound of Formula (I):

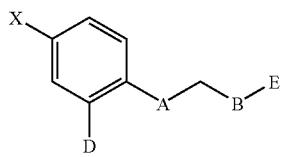

Formula (I)

wherein:

A is O, NH, or S;

B is a bond, —($C_2$-$C_7$)alkyl, —($C_2$-$C_7$)alkenyl, —($C_3$-$C_8$) cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;

D is isopropyl, isobutyl, sec-butyl, tert-butyl, cyclopropyl, cyclobutyl, cyclopentyl, methylenecyclopropyl, methylenecyclobutyl, methylenecyclopentyl;

E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;

R is H, an optionally substituted aryl, an optionally substituted heterocycloalkyl, or an optionally substituted heteroaryl;

X is a halogen;

or an active metabolite, or a pharmaceutically acceptable prodrug, salt, or solvate thereof. In one embodiment, the therapeutically effective amount of a compound of Formula (I) is provided in the form of an oral pharmaceutical composition for systemic administration of the compound.

In one embodiment is a method for treating a retinol-related disease in a mammal comprising administering a therapeutically effective amount of a compound of Formula (II):

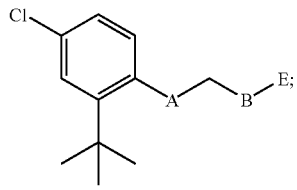

Formula (II)

wherein:

A is O, NH, or S;

B is a bond, —($C_2$-$C_7$)alkyl, —($C_2$-$C_7$)alkenyl, —($C_3$-$C_8$) cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;

E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;

R is H, an optionally substituted aryl, an optionally substituted heterocycloalkyl, or an optionally substituted heteroaryl;

or an active metabolite, or a pharmaceutically acceptable prodrug, salt, or solvate thereof. In one embodiment, the therapeutically effective amount of a compound of Formula (II) is provided in the form of an oral pharmaceutical composition for systemic administration of the compound.

In another embodiment is a method for treating a retinol-related disease in a mammal, comprising administering to the mammal a therapeutically effective amount of a compound of Formula (I) or (II) wherein the retinol-related disease is hyperostosis, idiopathic intracranial hypertension, amyloidosis, Alzheimer's disease, and Alström-Hallgren syndrome.

In one aspect is a method for reducing serum retinol levels in a mammal with dry form age related macular degeneration comprising administering to the mammal a therapeutically effective amount of a compound of Formula (I):

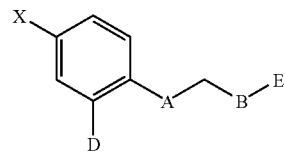

Formula (I)

wherein:

A is O, NH, or S;

B is a bond, —($C_2$-$C_7$)alkyl, —($C_2$-$C_7$)alkenyl, —($C_3$-$C_8$) cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;

D is isopropyl, isobutyl, sec-butyl, tert-butyl, cyclopropyl, cyclobutyl, cyclopentyl, methylenecyclopropyl, methylenecyclobutyl, methylenecyclopentyl;

E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;

R is H, an optionally substituted aryl, an optionally substituted heterocycloalkyl, or an optionally substituted heteroaryl;

X is a halogen;

or an active metabolite, or a pharmaceutically acceptable prodrug, salt, or solvate thereof, wherein the compound of Formula (I) does not directly modulate the activity of an enzyme or protein in the visual cycle. In one embodiment, the therapeutically effective amount of a compound of Formula (I) is provided in the form of an oral pharmaceutical composition for systemic administration of the compound.

In one embodiment is a method for reducing serum retinol levels in a mammal with dry form age related macular degeneration comprising administering a therapeutically effective amount of a compound of Formula (II):

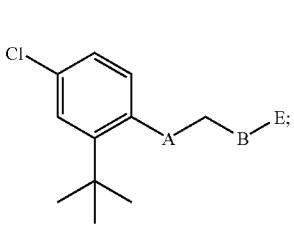

Formula (II)

wherein:

A is O, NH, or S;

B is a bond, —($C_2$-$C_7$)alkyl, —($C_2$-$C_7$)alkenyl, —($C_3$-$C_8$)cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;

E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;

R is H, an optionally substituted aryl, an optionally substituted heterocycloalkyl, or an optionally substituted heteroaryl;

or an active metabolite, or a pharmaceutically acceptable prodrug, salt, or solvate thereof, wherein the compound of Formula (II) does not directly modulate the activity of an enzyme or protein in the visual cycle. In one embodiment, the therapeutically effective amount of a compound of Formula (II) is provided in the form of an oral pharmaceutical composition for systemic administration of the compound.

In another embodiment is a method for reducing serum retinol levels in a mammal with dry form age related macular degeneration comprising administering to the mammal a compound of Formula (I) or (II) wherein the compound of Formula (I) or (II) does not directly inhibit or bind to an enzyme or protein in the visual cycle.

In a further embodiment is a method for reducing a serum retinol level in a mammal with dry form age related macular degeneration comprising administering to the mammal a compound of Formula (I) or (II) wherein the compound of Formula (I) or (II) does not affect the rate of rhodopsin regeneration.

In yet another embodiment is a method for reducing a serum retinol level in a mammal with dry form age related macular degeneration comprising administering to the mammal a compound of Formula (I) or (II) wherein the compound of Formula (I) or (II) does not worsen delayed dark adaptation.

In yet a further embodiment is a method for reducing a serum retinol level in a mammal with dry form age related macular degeneration comprising administering to the mammal a compound of Formula (I) or (II) wherein the compound of Formula (I) or (II) limits the spread of geographic atrophy or photoreceptor degeneration.

In one aspect is a method for treating hyperretinolemia comprising administering to a mammal a therapeutically effective amount of a compound of Formula (I):

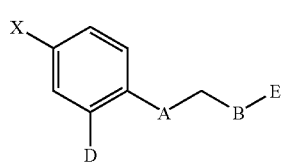

Formula (I)

wherein:

A is O, NH, or S;

B is a bond, —($C_2$-$C_7$)alkyl, —($C_2$-$C_7$)alkenyl, —($C_3$-$C_8$)cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;

D is isopropyl, isobutyl, sec-butyl, tert-butyl, cyclopropyl, cyclobutyl, cyclopentyl, methylenecyclopropyl, methylenecyclobutyl, methylenecyclopentyl;

E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;

R is H, an optionally substituted aryl, an optionally substituted heterocycloalkyl, or an optionally substituted heteroaryl;

X is a halogen;

or an active metabolite, or a pharmaceutically acceptable prodrug, salt, or solvate thereof. In one embodiment, the therapeutically effective amount of a compound of Formula (I) is provided in the form of an oral pharmaceutical composition for systemic administration of the compound.

In another embodiment is a method for treating hyperretinolemia comprising administering a therapeutically effective amount of a compound of Formula (II):

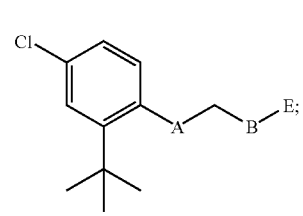

Formula (II)

wherein:

A is O, NH, or S;

B is a bond, —($C_2$-$C_7$)alkyl, —($C_2$-$C_7$)alkenyl, —($C_3$-$C_8$)cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;

E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;

R is H, an optionally substituted aryl, an optionally substituted heterocycloalkyl, or an optionally substituted heteroaryl;

or an active metabolite, or a pharmaceutically acceptable prodrug or solvate thereof. In one embodiment, the therapeutically effective amount of a compound of Formula (II) is provided in the form of an oral pharmaceutical composition for systemic administration of the compound.

In a further embodiment is a method for treating hyperretinolemia comprising administering to a mammal a compound of Formula (I) or (II) wherein hyperretinolemia is associated with a vitreoretinal disease.

In a yet another embodiment is a method for treating hyperretinolemia comprising administering to a mammal a compound of Formula (I) or (II) wherein hyperretinolemia is associated with diabetes or Alzheimer's disease.

In one aspect is a method for treating a retinol-related disease in a mammal, comprising administering to the mammal an effective amount of a compound of Formula (I):

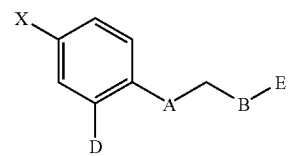

Formula (I)

wherein:

A is O, NH, or S;

B is a bond, —($C_2$-$C_7$)alkyl, —($C_2$-$C_7$)alkenyl, —($C_3$-$C_8$)cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;

D is isopropyl, isobutyl, sec-butyl, tert-butyl, cyclopropyl, cyclobutyl, cyclopentyl, methylenecyclopropyl, methylenecyclobutyl, methylenecyclopentyl;

E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;

R is H, an optionally substituted aryl, an optionally substituted heterocycloalkyl, or an optionally substituted heteroaryl;

X is a halogen;

or an active metabolite, or a pharmaceutically acceptable prodrug, salt, or solvate thereof, wherein the compound of Formula (I) inhibits a retinol-retinol binding protein-transthyretin complex formation; wherein an $IC_{50}$ inhibition is less than about 5 μM. In one embodiment, the effective amount of a compound of Formula (I) is provided in the form of an oral pharmaceutical composition for systemic administration of the compound.

In one embodiment is a method for treating a retinol-related disease in a mammal comprising administering to the mammal an effective amount of a compound of Formula (II):

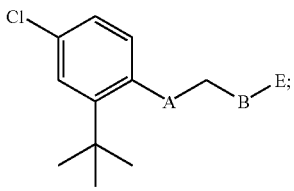

Formula (II)

wherein:

A is O, NH, or S;

B is a bond, —($C_2$-$C_7$)alkyl, —($C_2$-$C_7$)alkenyl, —($C_3$-$C_8$)cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;

E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;

R is H, an optionally substituted aryl, an optionally substituted heterocycloalkyl, or an optionally substituted heteroaryl;

or an active metabolite, or a pharmaceutically acceptable prodrug, salt, or solvate thereof, wherein the compound of Formula (II) inhibits the retinol-retinol binding protein-transthyretin complex formation; wherein the $IC_{50}$ inhibition is less than about 5M. In one embodiment, the effective amount of a compound of Formula (II) is provided in the form of an oral pharmaceutical composition for systemic administration of the compound.

In one embodiment is a method for treating a retinol-related disease in a mammal, comprising administering to the mammal an effective amount of a compound of Formula (I) or (II), wherein the compound of Formula (I) or (II) inhibits the retinol-retinol binding protein-transthyretin complex formation; wherein the $IC_{50}$ inhibition is less than about 1 μM.

In another embodiment is a method for treating a retinol-related disease in a mammal, comprising administering to the mammal an effective amount of a compound of Formula (I) or (II), wherein the compound of Formula (I) or (II) inhibits the retinol-retinol binding protein-transthyretin complex formation and wherein the compound of Formula (I) or (II) further inhibits cytochrome $P_{450}$ at less than about 50%.

In another embodiment is a method for treating a retinol-related disease in a mammal, comprising administering to the mammal an effective amount of a compound of Formula (I) or (II), wherein the compound of Formula (I) or (II) inhibits the retinol-retinol binding protein-transthyretin complex formation and wherein the compound of Formula (I) or (II) further inhibits cytochrome $P_{450}$ inhibition at less than about 10%.

In one aspect is a method for treating Type I or Type II diabetes in a mammal, comprising administering to the mammal a therapeutically effective amount of a compound of Formula (I):

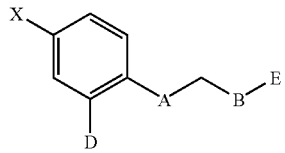

Formula (I)

wherein:

A is O, NH, or S;

B is a bond, —($C_2$-$C_7$)alkyl, —($C_2$-$C_7$)alkenyl, —($C_3$-$C_8$)cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;

D is isopropyl, isobutyl, sec-butyl, tert-butyl, cyclopropyl, cyclobutyl, cyclopentyl, methylenecyclopropyl, methylenecyclobutyl, methylenecyclopentyl;

E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;

R is H, an optionally substituted aryl, an optionally substituted heterocycloalkyl, or an optionally substituted heteroaryl;

X is a halogen;

or an active metabolite, or a pharmaceutically acceptable prodrug, salt, or solvate thereof, wherein the compound of Formula (I) modulates retinol binding protein or transthyretin levels or activity in the mammal. In one embodiment, the therapeutically effective amount of a compound of Formula (I) is provided in the form of an oral pharmaceutical composition for systemic administration of the compound.

In one embodiment is a method for treating Type I or Type II diabetes in a mammal, comprising administering to the mammal a therapeutically effective amount of a compound of Formula (II):

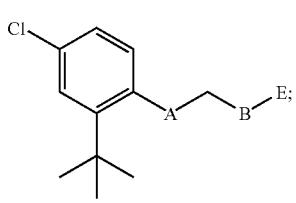

Formula (II)

wherein:

A is O, NH, or S;

B is a bond, —(C$_2$-C$_7$)alkyl, —(C$_2$-C$_7$)alkenyl, —(C$_3$-C$_8$)cycloalkyl, —(C$_2$-C$_7$)heteroalkyl, —(C$_3$-C$_8$)heterocycloalkyl, —(C$_3$-C$_8$)cycloalkenyl, —(C$_3$-C$_8$)heterocycloalkenyl;

E is (C=O)—OR, —O—(C=O)—R, —(C=O)—R, —OR, a carboxylic acid bioisostere, —(C=O)—NR$^1$R, NR$^1$—(C=O)—R, —(C$_1$-C$_7$)alkyl-(C=O)—OR, or —(C$_1$-C$_7$)alkyl-(C=O)—NR$^1$R;

R is H, an optionally substituted aryl, an optionally substituted heterocycloalkyl, or an optionally substituted heteroaryl;

or an active metabolite, or a pharmaceutically acceptable prodrug, salt, or solvate thereof, wherein the compound of Formula (II) modulates retinol binding protein or transthyretin levels or activity in the mammal. In one embodiment, the therapeutically effective amount of a compound of Formula (II) is provided in the form of an oral pharmaceutical composition for systemic administration of the compound.

In one aspect is a method for reducing the serum retinol or ocular tissue retinol levels in a mammal, comprising administering to the mammal a therapeutically effective amount of a compound of Formula (I):

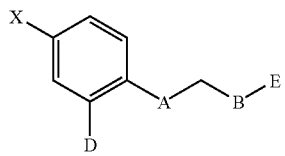

Formula (I)

wherein:

A is O, NH, or S;

B is a bond, —(C$_2$-C$_7$)alkyl, —(C$_2$-C$_7$)alkenyl, —(C$_3$-C$_8$)cycloalkyl, —(C$_2$-C$_7$)heteroalkyl, —(C$_3$-C$_8$)heterocycloalkyl, —(C$_3$-C$_8$)cycloalkenyl, —(C$_3$-C$_8$)heterocycloalkenyl;

D is isopropyl, isobutyl, sec-butyl, tert-butyl, cyclopropyl, cyclobutyl, cyclopentyl, methylenecyclopropyl, methylenecyclobutyl, methylenecyclopentyl;

E is (C=O)—OR, —O—(C=O)—R, —(C=O)—R, —OR, a carboxylic acid bioisostere, —(C=O)—NR$^1$R, NR$^1$—(C=O)—R, —(C$_1$-C$_7$)alkyl-(C=O)—OR, or —(C$_1$-C$_7$)alkyl-(C=O)—NR$^1$R;

R is H, an optionally substituted aryl, an optionally substituted heterocycloalkyl, or an optionally substituted heteroaryl;

X is a halogen;

or an active metabolite, or a pharmaceutically acceptable prodrug, salt, or solvate thereof. In one embodiment, the therapeutically effective amount of a compound of Formula (I) is provided in the form of an oral pharmaceutical composition for systemic administration of the compound.

In one embodiment is a method for reducing the serum retinol or ocular tissue retinol levels in a mammal, comprising administering to the mammal a therapeutically effective amount of a compound of Formula (II):

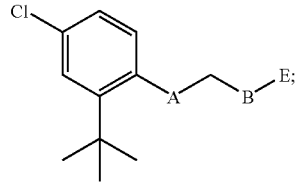

Formula (II)

wherein:

A is O, NH, or S;

B is a bond, —(C$_2$-C$_7$)alkyl, —(C$_2$-C$_7$)alkenyl, —(C$_3$-C$_8$)cycloalkyl, —(C$_2$-C$_7$)heteroalkyl, —(C$_3$-C$_8$)heterocycloalkyl, —(C$_3$-C$_8$)cycloalkenyl, —(C$_3$-C$_8$)heterocycloalkenyl;

E is (C=O)—OR, —O—(C=O)—R, —(C=O)—R, —OR, a carboxylic acid bioisostere, —(C=O)—NR$^1$R, NR$^1$—(C=O)—R, —(C$_1$-C$_7$)alkyl-(C=O)—OR, or —(C$_1$-C$_7$)alkyl-(C=O)—NR$^1$R;

R is H, an optionally substituted aryl, an optionally substituted heterocycloalkyl, or an optionally substituted heteroaryl;

or an active metabolite, or a pharmaceutically acceptable prodrug, salt, or solvate thereof. In one embodiment, the therapeutically effective amount of a compound of Formula (II) is provided in the form of an oral pharmaceutical composition for systemic administration of the compound.

In another embodiment is a method for reducing the serum retinol or ocular tissue retinol levels in a mammal, comprising administering to the mammal an effective amount of a compound of Formula (I) or (II) wherein the mammal is a human.

In a further embodiment is a method for reducing the serum retinol or ocular tissue retinol levels in a mammal, comprising administering to the mammal an effective amount of a compound of Formula (I) or (II) wherein the serum retinol or ocular tissue retinol level is reduced by at least 20%.

In yet a further embodiment is a method for reducing the serum retinol or ocular tissue retinol levels in a mammal, comprising administering to the mammal an effective amount of a compound of Formula (I) or (II) further comprising administering at least one additional agent selected from the group consisting of an inducer of nitric oxide production, an anti-inflammatory agent, a physiologically acceptable antioxidant, a physiologically acceptable mineral, a negatively charged phospholipid, a carotenoid, a statin, an anti-angiogenic drug, a matrix metalloproteinase inhibitor, resveratrol and other trans-stilbene compounds, and 13-cis-retinoic acid.

In one aspect is a composition comprising a compound of Formula (I):

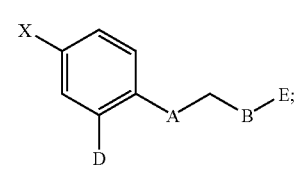

Formula (I)

wherein:

A is O, NH, or S;

B is a bond, —(C$_2$-C$_7$)alkyl, —(C$_2$-C$_7$)alkenyl, —(C$_3$-C$_8$)cycloalkyl, —(C$_2$-C$_7$)heteroalkyl, —(C$_3$-C$_8$)heterocycloalkyl, —(C$_3$-C$_8$)cycloalkenyl, —(C$_3$-C$_8$)heterocycloalkenyl; with the proviso that —(C$_2$-C$_7$)heteroalkyl cannot contain a nitrogen atom, —C(=O)—, —S—, —S(=O)—, —S(=O)$_2$—, —NR$^1$(C=O)—, —(C=O)NR$^1$—, S(=O)$_2$NR$^1$—, —NR$^1$S(=O)$_2$, —O(C=O)NR$^1$—, —NR$^1$(C=O)O—, —O(C=O) O—, —NR$^1$(C=O)NR$^1$—, —(C=O)O—, —O(C=O)—;

D is isopropyl, isobutyl, sec-butyl, tert-butyl, cyclopropyl, cyclobutyl, cyclopentyl, methylenecyclopropyl, methylenecyclobutyl, methylenecyclopentyl;

E is (C=O)—OR, —O—(C=O)—R, —(C=O)—R, —OR, a carboxylic acid bioisostere, —(C=O)—NR$^1$R, NR$^1$—(C=O)—R; —(C$_1$-C$_7$)alkyl-(C=O)—OR, —(C$_1$-C$_7$)alkyl-(C=O)—NR$^1$R, C$_1$-C$_4$ alkyl, C$_2$-C$_4$ alkynyl, C$_3$-C$_6$ cycloalkyl, C$_1$-C$_4$alkyl-(C$_3$-C$_6$cycloalkyl), aryl, heteroaryl, substituted heteroaryl, substituted aryl, arylalkyl, —C(O)R$^2$, hydroxy-(C$_1$-C$_6$ alkyl), arloxy, halo, C$_1$-C$_6$-haloalkyl, cyano, hydroxy, nitro, —O—C(O)NR$^2$R$^3$, —NR$^2$R$^3$(C=O)OR$^1$, —SO$_2$NR$^2$R$^3$, with the proviso that heteroaryl cannot contain a nitrogen atom;

R$^2$ and R$^3$ are each independently selected from among H, C$_1$-C$_6$ alkyl, and C$_3$-C$_6$ cycloalkyl;

R is H, an optionally substituted aryl, or an optionally substituted heteroaryl with the proviso that when B is —S—, R cannot be pyrimidine; and when B is —(C$_2$-C$_7$)alkyl, R cannot be imidazole;

R$^1$ is H or (C$_1$-C$_6$)alkyl;

X is a halogen;

with the proviso that E cannot be

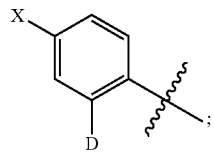

or an active metabolite, or a pharmaceutically acceptable prodrug, salt, or solvate thereof.

In one embodiment is a composition comprising a compound of Formula (I):

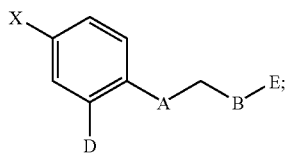

wherein:

A is O, NH, or S;

B is a bond, —(C$_2$-C$_7$)alkyl, —(C$_2$-C$_7$)alkenyl, —(C$_3$-C$_8$) cycloalkyl, —(C$_2$-C$_7$)heteroalkyl, —(C$_3$-C$_8$)heterocloalkyl, —(C$_3$-C$_8$)cycloalkenyl, —(C$_3$-C$_8$)heterocloalkenyl; with the proviso that —(C$_2$-C$_7$)heteroalkyl cannot contain a nitrogen atom, —C(=O)—, —S—, —S(=O)—, —S(=O)$_2$—, —NR$^1$(C=O)—, —(C=O)NR$^1$—, S(=O)$_2$NR$^1$—, —NR$^1$S(=O)$_2$, —O(C=O)NR$^1$—, —NR$^1$(C=O)O—, —O(C=O) O—, —NR$^1$(C=O)NR$^1$—, —(C=O)O—, —O(C=O)—;

D is tert-butyl;

E is (C=O)—OR, —O—(C=O)—R, —(C=O)—R, —OR, a carboxylic acid bioisostere, —(C=O)—NR$^1$R, NR$^1$—(C=O)—R; —(C$_1$-C$_7$)alkyl-(C=O)—OR, —(C$_1$-C$_7$)alkyl-(C=O)—NR$^1$R, C$_1$-C$_4$ alkyl, C$_2$-C$_4$ alkynyl, C$_3$-C$_6$ cycloalkyl, C$_1$-C$_4$alkyl-(C$_3$-C$_6$cycloalkyl), aryl, substituted aryl, arylalkyl, —C(O) R$^2$, hydroxy-(C$_1$-C$_6$ alkyl), arloxy, halo, C$_1$-C$_6$-haloalkyl, cyano, hydroxy, nitro, —O—C(O)NR$^2$R$^3$, —NR$^2$R$^3$(C=O)OR$^1$, —SO$_2$NR$^2$R$^3$;

R$^2$ and R$^3$ are each independently selected from among H, C$_1$-C$_6$ alkyl, and C$_3$-C$_6$ cycloalkyl;

R is H, an optionally substituted aryl, or an optionally substituted heteroaryl with the proviso that when B is —S—, R cannot be pyrimidine; and when B is —(C$_2$-C$_7$)alkyl, R cannot be imidazole;

R$^1$ is H or (C$_1$-C$_6$)alkyl;

X is Cl;

with the proviso that the compound of Formula (I) cannot be a dimer;

or an active metabolite, or a pharmaceutically acceptable prodrug, salt, or solvate thereof.

A pharmaceutical composition comprising the compound of Formula (I):

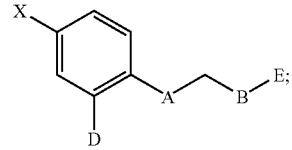

wherein:

A is O, NH, or S;

B is a bond, —(C$_2$-C$_7$)alkyl, —(C$_2$-C$_7$)alkenyl, —(C$_3$-C$_8$) cycloalkyl, —(C$_2$-C$_7$)heteroalkyl, —(C$_3$-C$_8$)heterocloalkyl, —(C$_3$-C$_8$)cycloalkenyl, —(C$_3$-C$_8$)heterocloalkenyl; with the proviso that —(C$_2$-C$_7$)heteroalkyl cannot contain a nitrogen atom, —C(=O)—, —S—, —S(=O)—, —S(=O)$_2$—, —NR$^1$(C=O)—, —(C=O)NR$^1$—, S(=O)$_2$NR$^1$—, —NR$^1$S(=O)$_2$, —O(C=O)NR$^1$—, —NR$^1$(C=O)O—, —O(C=O) O—, —NR$^1$(C=O)NR$^1$—, —(C=O)O—, —O(C=O)—;

D is isopropyl, isobutyl, sec-butyl, tert-butyl, cyclopropyl, cyclobutyl, cyclopentyl, methylenecyclopropyl, methylenecyclobutyl, methylenecyclopentyl;

E is (C=O)—OR, —O—(C=O)—R, —(C=O)—R, —OR, a carboxylic acid bioisostere, —(C=O)—NR$^1$R, NR$^1$—(C=O)—R; —(C$_1$-C$_7$)alkyl-(C=O)—OR, —(C$_1$-C$_7$)alkyl-(C=O)—NR$^1$R, C$_1$-C$_4$ alkyl, C$_2$-C$_4$ alkynyl, C$_3$-C$_6$ cycloalkyl, C$_1$-C$_4$alkyl-(C$_3$-C$_6$cycloalkyl), aryl, substituted aryl, arylalkyl, —C(O) R$^2$, hydroxy-(C$_1$-C$_6$ alkyl), arloxy, halo, C$_1$-C$_6$-haloalkyl, cyano, hydroxy, nitro, —O—C(O)NR$^2$R$^3$, —NR$^2$R$^3$(C=O)OR$^1$, —SO$_2$NR$^2$R$^3$;

R$^2$ and R$^3$ are each independently selected from among H, C$_1$-C$_6$ alkyl, and C$_3$-C$_6$ cycloalkyl;

R is H, an optionally substituted aryl, or an optionally substituted heteroaryl with the proviso that when B is —S—, R cannot be pyrimidine; and when B is —(C$_2$-C$_7$)alkyl, R cannot be imidazole;

$R^1$ is H or $(C_1-C_6)$alkyl;

X is a halogen;

with the proviso that the compound of Formula (I) cannot be a dimer;

and a pharmaceutically acceptable carrier or excipient. In one embodiment, the pharmaceutical composition is an oral pharmaceutical composition for systemic administration of the compound of Formula (I).

In some embodiments are compositions wherein E is $(C=O)$—OR, —O—$(C=O)$—R, —$(C=O)$—R, —OR, a carboxylic acid bioisostere, —$(C=O)$—$NR^1R$, $NR^1$—$(C=O)$—R; —$(C_1-C_7)$alkyl-$(C=O)$—OR, or —$(C_1-C_7)$alkyl-$(C=O)$—$NR^1R$. In other embodiments are compositions wherein X is Cl and D is isopropyl, tert-butyl or cyclopropyl. In further embodiments are compositions wherein D is tert-butyl and X is Cl. In some embodiments are compositions wherein B is —$(CH_2)$, and n is 1-6, or B is —$(C_3-C_8)$cycloalkyl. In some embodiments are compositions wherein A is O. In other embodiments are compositions wherein A is NH or S.

In some embodiments are methods for treatment described herein comprising administering to a mammal a therapeutically effective amount of the composition of the compound of Formula (I):

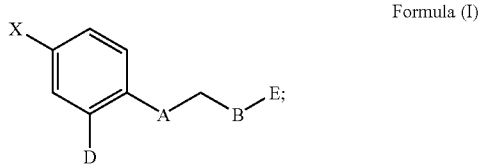

Formula (I)

wherein:

A is O, NH, or S;

B is a bond, —$(C_2-C_7)$alkyl, —$(C_2-C_7)$alkenyl, —$(C_3-C_8)$cycloalkyl, —$(C_2-C_7)$heteroalkyl, —$(C_3-C_8)$heterocycloalkyl, —$(C_3-C_8)$cycloalkenyl, —$(C_3-C_8)$heterocycloalkenyl; with the proviso that —$(C_2-C_7)$heteroalkyl cannot contain a nitrogen atom, —$C(=O)$—, —S—, —$S(=O)$—, —$S(=O)_2$—, —$NR^1(C=O)$—, —$(C=O)NR^1$—, $S(=O)_2NR^1$—, —$NR^1S(=O)_2$, —$O(C=O)NR^1$—, —$NR^1(C=O)O$—, —$O(C=O)$ O—, —$NR^1(C=O)NR^1$—, —$(C=O)O$—, —$O(C=O)$—;

D is tert-butyl;

E is $(C=O)$—OR, —O—$(C=O)$—R, —$(C=O)$—R, —OR, a carboxylic acid bioisostere, —$(C=O)$—$NR^1R$, $NR^1$—$(C=O)$—R; —$(C_1-C_7)$alkyl-$(C=O)$—OR, —$(C_1-C_7)$alkyl-$(C=O)$—$NR^1R$, $C_1-C_4$ alkyl, $C_2-C_4$ alkynyl, $C_3-C_6$ cycloalkyl, $C_1-C_4$alkyl-$(C_3-C_6$cycloalkyl), aryl, substituted aryl, arylalkyl, —$C(O)$ $R^2$, hydroxy-$(C_1-C_6$ alkyl), arloxy, halo, $C_1-C_6$-haloalkyl, cyano, hydroxy, nitro, —O—$C(O)NR^2R^3$, —$NR^2R^3(C=O)OR^1$, —$SO_2NR^2R^3$;

$R^2$ and $R^3$ are each independently selected from among H, $C_1-C_6$ alkyl, and $C_3-C_6$ cycloalkyl;

R is H, an optionally substituted aryl, or an optionally substituted heteroaryl with the proviso that when B is —S—, R cannot be pyrimidine; and when B is —$(C_2-C_7)$alkyl, R cannot be imidazole;

$R^1$ is H or $(C_1-C_6)$alkyl;

X is Cl;

with the proviso that the compound of Formula (I) cannot be a dimer;

or an active metabolite, or a pharmaceutically acceptable prodrug, salt, or solvate thereof.

In one aspect is a compound of Formula (I):

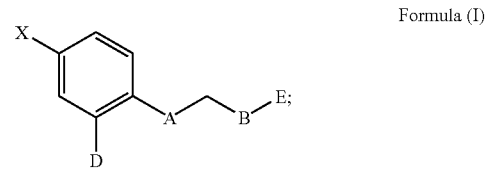

Formula (I)

wherein:

A is O;

B is a bond, —$(C_2-C_7)$alkyl, —$(C_2-C_7)$alkenyl, —$(C_3-C_8)$cycloalkyl, —$(C_2-C_7)$heteroalkyl, —$(C_3-C_8)$heterocycloalkyl, —$(C_3-C_8)$cycloalkenyl, —$(C_3-C_8)$heterocycloalkenyl; with the proviso that —$(C_2-C_7)$heteroalkyl cannot contain a nitrogen atom, —$C(=O)$—, —S—, —$S(=O)$—, —$S(=O)_2$—, —$NR^1(C=O)$—, —$(C=O)NR^1$—, $S(=O)_2NR^1$—, —$NR^1S(=O)_2$, —$O(C=O)NR^1$—, —$NR^1(C=O)O$—, —$O(C=O)$ O—, —$NR^1(C=O)NR^1$—, —$(C=O)O$—, —$O(C=O)$—;

D is isopropyl, isobutyl, sec-butyl, tert-butyl, cyclopropyl, cyclobutyl, cyclopentyl, methylenecyclopropyl, methylenecyclobutyl, methylenecyclopentyl;

E is $(C=O)$—OR, —O—$(C=O)$—R, —$(C=O)$—R, —OR, a carboxylic acid bioisostere, —$(C=O)$—$NR^1R$, $NR^1$—$(C=O)$—R; —$(C_1-C_7)$alkyl-$(C=O)$—OR, —$(C_1-C_7)$alkyl-$(C=O)$—$NR^1R$, $C_1-C_4$ alkyl, $C_2-C_4$ alkynyl, $C_3-C_6$ cycloalkyl, $C_1-C_4$alkyl-$(C_3-C_6$cycloalkyl), aryl, substituted aryl, arylalkyl, —$C(O)$ $R^2$, hydroxy-$(C_1-C_6$ alkyl), arloxy, halo, $C_1-C_6$-haloalkyl, cyano, hydroxy, nitro, —O—$C(O)NR^2R^3$—, $NR^2(C=O)OR^1$, or —$SO_2NR^2R^3$;

$R^2$ and $R^3$ are each independently selected from among H, $C_1-C_6$ alkyl, and $C_3-C_6$ cycloalkyl;

R is H, —$(C_2-C_7)$alkyl, an optionally substituted aryl, or an optionally substituted heteroaryl with the proviso that when B is —S—, R cannot be pyrimidine; and when B is —$(C_2-C_7)$alkyl, R cannot be imidazole;

$R^1$ is H or $(C_1-C_6)$alkyl; and

X is a halogen;

or an active metabolite, or a pharmaceutically acceptable prodrug, salt, or solvate thereof.

In some embodiments is a compound of Formula (I), wherein B is —$(CH_2)$, and n is 1-6, or B is —$(C_3-C_8)$cycloalkyl. In other embodiments, E is $(C=O)$—OR, a carboxylic acid bioisostere, —$(C=O)$—$NR^1R$, —$(C_1-C_7)$alkyl-$(C=O)$—OR, or —$(C_1-C_7)$alkyl-$(C=O)$—$NR^1R$. In further embodiments is a compound of Formula (I), wherein D is isopropyl, tert-butyl or cyclopropyl. In some embodiments, X is Cl and D is tert-butyl.

In another aspect is a compound of Formula (I):

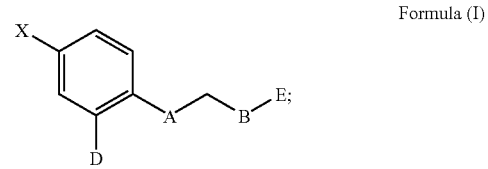

Formula (I)

wherein:

A is NH, or S;

B is a bond, —$(C_2-C_7)$alkyl, —$(C_2-C_7)$alkenyl, —$(C_3-C_8)$cycloalkyl, —$(C_2-C_7)$heteroalkyl, —$(C_3-C_8)$heterocycloalkyl, —$(C_3-C_8)$cycloalkenyl, —$(C_3-C_8)$heterocycloalkenyl;

D is isopropyl, isobutyl, sec-butyl, tert-butyl, cyclopropyl, cyclobutyl, cyclopentyl, methylenecyclopropyl, methylenecyclobutyl, methylenecyclopentyl;

E is (C=O)—OR, —O—(C=O)—R, —(C=O)—R, —OR, a carboxylic acid bioisostere, —(C=O)—NR$^1$R, NR$^1$—(C=O)—R; —(C$_1$-C$_7$)alkyl-(C=O)—OR, —(C$_1$-C$_7$)alkyl-(C=O)—NR$^1$R, C$_1$-C$_4$ alkyl, C$_2$-C$_4$ alkynyl, C$_3$-C$_6$ cycloalkyl, C$_1$-C$_4$alkyl-(C$_3$-C$_6$cycloalkyl), aryl, substituted aryl, arylalkyl, —C(O)R$^2$, hydroxy-(C$_1$-C$_6$ alkyl), aroxy, halo, C$_1$-C$_6$-haloalkyl, cyano, hydroxy, nitro, —O—C(O)NR$^2$R$^3$, —NR$^2$(C=O)OR$^1$, or —SO$_2$NR$^2$R$^3$;

R$^2$ and R$^3$ are each independently selected from among H, C$_1$-C$_6$ alkyl, and C$_3$-C$_6$ cycloalkyl;

R is H, —(C$_2$-C$_7$)alkyl, an optionally substituted aryl, or an optionally substituted heteroaryl;

R$^1$ is H or (C$_1$-C$_6$)alkyl; and

X is a halogen;

or an active metabolite, or a pharmaceutically acceptable prodrug, salt, or solvate thereof.

In some embodiments is a compound of Formula (I), wherein B is —(CH$_2$), and n is 1-6, or B is —(C$_3$-C$_8$)cycloalkyl. In other embodiments, E is (C=O)—OR, a carboxylic acid bioisostere, —(C=O)—NR$^1$R, —(C$_1$-C$_7$)alkyl-(C=O)—OR, or —(C$_1$-C$_7$)alkyl-(C=O)—NR$^1$R. In further embodiments is a compound of Formula (I), wherein D is isopropyl, tert-butyl or cyclopropyl. In some embodiments, X is Cl and D is tert-butyl.

Other objects, features and advantages of the methods, compounds, and compositions described herein will become apparent from the following detailed description. It should be understood, however, that the detailed description and the specific examples, while indicating specific embodiments, are given by way of illustration only.

DETAILED DESCRIPTION OF THE INVENTION

Figure 1:
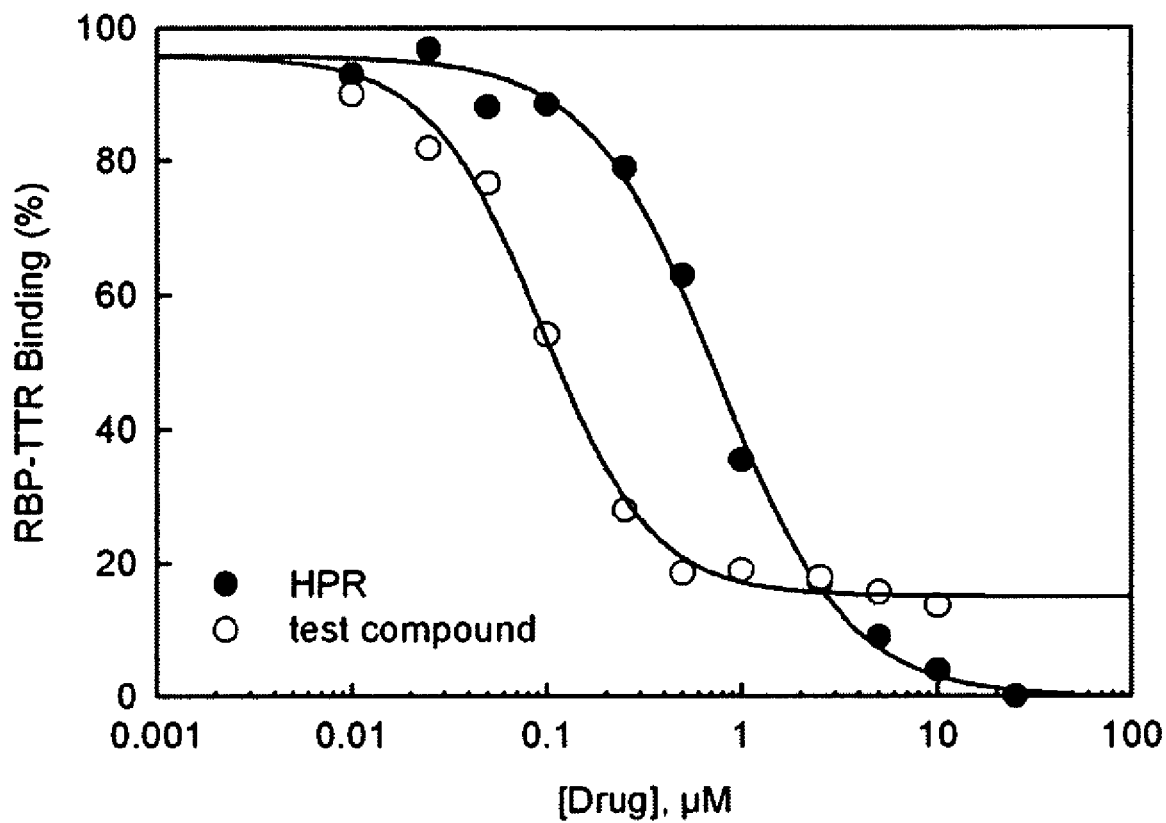
FIG. 1. Dose-response relationship of a test compound compared to fenretinide (HPR). The data show that the test compound (with a chemical structure consistent with Formula I) is approximately 7-fold more potent than HPR at disrupting RBP4-TTR interaction (IC$_{50}$=0.1 vs. IC$_{50}$=0.7, respectively).

Reference will now be made in detail to embodiments of the methods and compositions disclosed herein. Examples of the embodiments are illustrated in the following Examples section.

Of interest, the compounds of Formula (I) and (II) are used to provide benefit to patients suffering from or susceptible to various vitreoretinal diseases, including but not limited to, macular degeneration and dystrophy. Compounds of Formula (I) and (II) provide at least one of the following benefits to such patients: reduction in the level of serum retinol or RBP, modulation in the level of transthyretin, reduction in the formation of drusen, reduction in the formation of the retinol-retinol-binding protein complex, and reduction in the formation of the retinol-binding protein-transthyretin complex. As used herein, RBP refers to the protein RBP4.

The use of compounds of Formula (I) and (II) also includes as a preventative therapy for wet form age-related macular degeneration. In addition, the compounds of Formula (I) and (II) provide further therapeutic effect for wet-form age-related macular degeneration because such compounds additionally have anti-angiogenic activity.

The Visual Cycle

The vertebrate retina contains two types of photoreceptor cells—rods and cones. Rods are specialized for vision under low light conditions. Cones are less sensitive, provide vision at high temporal and spatial resolutions, and afford color perception. Under daylight conditions, the rod response is saturated and vision is mediated entirely by cones. Both cell types contain a structure called the outer segment comprising a stack of membranous discs. The reactions of visual transduction take place on the surfaces of these discs. The first step in vision is absorption of a photon by an opsin-pigment molecule (rhodopsin), which involves 11-cis to all-trans isomerization of the chromophore. Before light sensitivity can be regained, the resulting all-trans-retinal must be converted back 11-cis-retinal in a multi-enzyme process which takes place in the retinal pigment epithelium, a monolayer of cells adjacent to the retina.

Macular or Retinal Degenerations and Dystrophies

Macular degeneration (also referred to as retinal degeneration) is a disease of the eye that involves deterioration of the macula, the central portion of the retina. Approximately 85% to 90% of the cases of macular degeneration are the "dry" (atrophic or non-neovascular) type. In dry macular degeneration, the deterioration of the retina is associated with the formation of small yellow deposits, known as drusen, under the macula; in addition, the accumulation of lipofuscin in the RPE leads to photoreceptor degeneration and geographic atrophy. This phenomena leads to a thinning and degeneration of the macula. The location and amount of thinning in the retina caused by the drusen directly correlates to the amount of central vision loss. Degeneration of the pigmented layer of the retina and photoreceptors overlying drusen become atrophic and can cause a slow loss of central vision. Ultimately, loss of retinal pigment epithelium and underlying photoreceptor cells results in geographic atrophy. Administration of at least one compound having the structure of Formula (I) or (II) to a mammal reduces the formation of, or limit the spread of, photoreceptor degeneration and/or geographic atrophy in the eye of the mammal. By way of example only, administration of a compound of Formula (I) or (II) to a mammal, is used to treat photoreceptor degeneration and/or geographic atrophy in the eye of the mammal.

In "wet" macular degeneration new blood vessels form (i.e., neovascularization) to improve the blood supply to retinal tissue, specifically beneath the macula, a portion of the retina that is responsible for our sharp central vision. The new vessels are easily damaged and sometimes rupture, causing bleeding and injury to the surrounding tissue. Although wet macular degeneration only occurs in about 10 percent of all macular degeneration cases, it accounts for approximately 90% of macular degeneration-related blindness. Neovascularization can lead to rapid loss of vision and eventual scarring of the retinal tissues and bleeding in the eye. This scar tissue and blood produces a dark, distorted area in the vision, often rendering the eye legally blind. Wet macular degeneration usually starts with distortion in the central field of vision. Straight lines become wavy. Many people with macular degeneration also report having blurred vision and blank spots (scotoma) in their visual field. Growth promoting proteins called vascular endothelial growth factor, or VEGF, have been targeted for triggering this abnormal vessel growth in the eye. This discovery has lead to aggressive research of experimental drugs that inhibit or block VEGF. Studies have shown that anti-VEGF agents blocks and prevents abnormal blood vessel growth. Such anti-VEGF agents stop or inhibit VEGF stimulation, so there is less growth of blood vessels. Such anti-VEGF agents may also be successful in anti-angiogenesis or blocking VEGF's ability to induce blood vessel growth beneath the retina, as well as blood vessel leakiness. In one embodiment, administration of at least one compound having the structure of Formula (I) or (II) to a mammal reduces the formation of, or limit the spread of, wet-form age-related macular degeneration in the eye of the mammal. By way of example only, administration of a compound of Formula (I) or (II) to a mammal, is used to treat wet-form age-related macular degeneration in the eye of the mammal. Similarly, the compounds of Formula (I) or (II) are used to treat choroidal neovascularization and the formation of abnormal blood vessels beneath the macula of the eye of a mammal. In one embodiment, such therapeutic benefits result from a number of effects: lowering of serum retinol and thus ocular retinol levels; anti-angiogenic activity, and/or the quelling of geographic atrophy.

Stargardt Disease is a macular dystrophy that manifests as a recessive form of macular degeneration with an onset during childhood. See e.g., Allikmets et al., Science, 277:1805-07 (1997); Lewis et al., Am J. Hum. Genet., 64:422-34 (1999); Stone et al., Nature Genetics, 20:328-29 (1998); Allikmets, Am. J. Hum. Gen., 67:793-799 (2000); Klevering, et al, Opthalmology, 111:546-553 (2004). Stargardt Disease is characterized clinically by progressive loss of central vision and progressive atrophy of the RPE overlying the macula. Mutations in the human ABCA4 gene for Rim Protein (RmP) are responsible for Stargardt Disease. Early in the disease course, patients show delayed dark adaptation but otherwise normal rod function. Histologically, Stargardt Disease is associated with deposition of lipofuscin pigment granules in RPE cells.

Mutations in ABCA4 have also been implicated in recessive retinitis pigmentosa, see, e.g., Cremers et al., Hum. Mol. Genet., 7:355-62 (1998), recessive cone-rod dystrophy, see id., and non-exudative age-related macular degeneration, see e.g., Allikmets et al., Science, 277:1805-07 (1997); Lewis et al., Am. J. Hum. Genet., 64:422-34 (1999), although the prevalence of ABCA4 mutations in AMD is still uncertain. See Stone et al., Nature Genetics, 20:328-29 (1998); Allikmets, Am. J. Hum. Gen., 67:793-799 (2000); Klevering, et al, Opthalmology, 111:546-553 (2004). Similar to Stargardt Disease, these diseases are associated with delayed rod dark-adaptation. See Steinmetz et al., Brit. J. Ophthalm., 77:549-54 (1993). Lipofuscin deposition in RPE cells is also seen prominently in AMD, see Kliffen et al., Microsc. Res. Tech., 36:106-22 (1997) and some cases of retinitis pigmentosa. See Bergsma et al., Nature, 265:62-67 (1977). In addition, an autosomal dominant form of Stargardt Disease is caused by mutations in the ELOV4 gene. See Karan, et al, Proc. Natl. Acad. Sci. (2005).

In addition, there are several types of macular degenerations that affect children, teenagers or adults that are commonly known as early onset or juvenile macular degeneration. Many of these types are hereditary and are looked upon as macular dystrophies instead of degeneration. Some examples of macular dystrophies include: Cone-Rod Dystrophy, Corneal Dystrophy, Fuch's Dystrophy, Sorsby's Macular Dystrophy, Best Disease, and Juvenile Retinoschisis, as well as Stargardt Disease.

Modulation of Vitamin A Levels

Vitamin A (all-trans retinol) is a vital cellular nutrient which cannot be synthesized de novo and therefore must be obtained from dietary sources. Vitamin A is a generic term which may designate any compound possessing the biological activity, including binding activity, of retinol. One retinol equivalent (RE) is the specific biologic activity of 1 μg of all-trans retinol (3.33 IU) or 6 μg (10 IU) of beta-carotene. Beta-carotene, retinol and retinal (vitamin A aldehyde) all possess effective and reliable vitamin A activity. Each of these compounds are derived from the plant precursor molecule, carotene (a member of a family of molecules known as carotenoids). Beta-carotene, which consists of two molecules of retinal linked at their aldehyde ends, is also referred to as the provitamin form of vitamin A.

Ingested β-carotene is cleaved in the lumen of the intestine by β-carotene dioxygenase to yield retinal. Retinal is reduced to retinol by retinaldehyde reductase, an NADPH requiring enzyme within the intestines, and thereafter esterified to palmitic acid.

Following digestion, retinol in food material is transported to the liver bound to lipid aggregates. See Bellovino et al., Mol. Aspects. Med., 24:411-20 (2003). Once in the liver, retinol forms a complex with retinol binding protein (RBP) and is then secreted into the blood circulation. Before the retinol-RBP holoprotein can be delivered to extra-hepatic target tissues, such as by way of example, the eye, it must bind with transthyretin (TTR). Zanotti and Berni, Vitam. Horm., 69:271-95 (2004). It is this secondary complex which allows retinol to remain in the circulation for prolonged periods. Association with TTR facilitates RBP release from hepatocytes, and prevents renal filtration of the RBP-retinol complex. The retinol-RBP-TTR complex is delivered to target tissues where retinol is taken up and utilized for various cellular processes. Delivery of retinol to cells through the circulation by the RBP-TTR complex is the major pathway through which cells and tissue acquire retinol.

Retinol uptake from its complexed retinol-RBP-TTR form into cells occurs by binding of RBP to cellular receptors on target cells. This interaction leads to endocytosis of the RBP-receptor complex and subsequent release of retinol from the complex, or binding of retinol to cellular retinol binding proteins (CRBP), and subsequent release of apoRBP by the cells into the plasma. Other pathways contemplate alternative mechanisms for the entry of retinol into cells, including uptake of retinol alone into the cell. See Blomhoff (1994) for review.

The methods, compounds, and compositions described herein are useful for the modulation of vitamin A levels in a mammalian subject. In particular, modulation of vitamin A levels occurs through the regulation of retinol binding protein (RBP) and transthyretin (TTR) availability or activity in a mammal. The methods, compounds, and compositions described herein provide for the modulation of RBP and TTR levels or activity in a mammalian subject, and subsequently modulation of vitamin A levels. Increases or decreases in vitamin A levels in a subject have effects on retinol availability in target organs and tissues. Therefore, providing a means of modulating retinol or retinol derivative availability will correspondingly modulate disease conditions caused by a lack of or excess in local retinol or retinol derivative concentrations in the target organs and tissues. In addition, the therapeutic methods described herein are used for the treatment of hyperretinolemia, in which excessive levels of serum retinol lead to vitreoretinal diseases, or symptoms associated with vitreoretinal diseases (e.g., formation of lipofuscin or drusen).

For example, A2E, the major fluorophore of lipofuscin, is formed in macular or retinal degeneration or dystrophy, including age-related macular degeneration and Stargardt Disease, due to excess production of the visual-cycle retinoid, all-trans-retinaldehyde, a precursor of A2E. Reduction of vitamin A and all-trans retinaldehyde in the retina, therefore, will be beneficial in reducing A2E and lipofuscin build-up, and treatment of age-related macular degeneration.

Modulators (e.g. compounds of Formula (I) and (II)) that inhibit delivery of retinol to cells either through interruption of binding of retinol to apo RBP or holo RBP (RBP+retinol) to its transport protein, TTR, or the increased renal excretion of RBP and TTR, therefore, are useful in decreasing serum vitamin A levels, and buildup of retinol and its derivatives in target tissues such as the eye.

Similarly, modulators which affect the availability of the retinol transport proteins, retinol binding protein (RBP) and transthyretin (TTR), are useful in decreasing serum vitamin A levels, and buildup of retinol (e.g., hyperretinolemia) and its derivatives and physical manifestations in target tissues, such as the eye. TTR, for example, has been shown to be a component of Drusen constituents, suggesting a direct involvement of TTR in age-related macular degeneration. Mullins, R F, FASEB J. 14:835-846 (2000); Pfeffer B A, et al., Molecular Vision 10:23-30 (2004).

The same approach to modulation of RBP and/or TTR levels or activity in a mammal is expected to find use in the treatment of metabolic disorders, such as type I or type II diabetes (obese and/or non-obese), IIH, bone-related disorders, such as hyperostosis, protein misfolding and aggregation diseases, such as systemic amyloidoses and Alzheimer's disease, and Alström-Hallgren syndrome.

One embodiment of the methods, compounds, and compositions disclosed herein, therefore, provides for the modulation of RBP or TTR levels or activity in a mammal by administering to a mammal a therapeutically effective amount of at least one of the compounds of Formula (I) or Formula (II).

Retinol Binding Protein (RBP) and Transthyretin (TTR)

Retinol binding protein, or RBP, is a single polypeptide chain, with a molecular weight of approximately 21 kD. RBP has been cloned and sequenced, and its amino acid sequence determined. Colantuni et al., Nuc. Acids Res., 11:7769-7776 (1983). The three-dimensional structure of RBP reveals a specialized hydrophobic pocket designed to bind and protect the fat-soluble vitamin retinol. Newcomer et al., EMBO J., 3:1451-1454 (1984). In in vitro experiments, cultured hepatocytes have been shown to synthesize and secrete RBP. Blaner, W. S., Endocrine Rev., 10:308-316 (1989). Subsequent experiments have demonstrated that many cells contain mRNA for RBP, suggesting a widespread distribution of RBP synthesis throughout the body. See Blaner (1989). Most of the RBP secreted by the liver contains retinol in a 1:1 molar ratio, and retinol binding to RBP is required for normal RBP secretion.

In cells, RBP tightly binds to retinol in the endoplasmic reticulum, where it is found in high concentrations. Binding of retinol to RBP initiates a translocation of retinol-RBP from endoplasmic reticulum to the Golgi complex, followed by secretion of retinol-RBP from the cells. RBP secreted from hepatocytes also assists in the transfer of retinol from hepatocytes to stellate cells, where direct secretion of retinol-RBP into plasma takes place.

In plasma, approximately 95% of the plasma RBP is associated with transthyretin (TTR) in a 1:1 mol/mol ratio, wherein essentially all of the plasma vitamin A is bound to RBP. TTR is a well-characterized plasma protein consisting of four identical subunits with a molecular weight of 54,980 Daltons. The full three-dimensional structure, elucidated by X-ray diffraction, reveals extensive β-sheets arranged tetrahedrally. Blake et al., J. Mol. Biol., 121:339-356 (1978). A channel runs through the center of the tetramer which contains two binding sites for thyroxine. However, only one thyroxine molecule appears to be bound normally to TTR due to negative cooperativity. The complexation of TTR to RBP-retinol is thought to reduce the glomerular filtration of retinol, thereby increasing the half-life of retinol and RBP in plasma by about threefold.

Modulation of RBP or TTR Binding or Clearance in a Subject

Before retinol bound to RBP is transported in the blood stream for delivery to the eye, it must be complexed with TTR. It is this secondary complex which allows retinol to remain in the circulation for prolonged periods. In the absence of TTR, the retinol-RBP complex is rapidly excreted in the urine. Similarly, in the absence of RBP, retinol transport in the blood stream and uptake by cells is diminished.

Another embodiment described herein, therefore, is to modulate availability of RBP or TTR for complexing to retinol or retinol-RBP in the blood stream by lowering RBP or TTR binding characteristics or clearance rates. As mentioned above, the TTR binding to RBP holoprotein decreases the clearance rate of RBP and retinol. Therefore, by modulating either RBP or TTR availability or activity, retinol levels will be likewise modulated in a subject in need thereof.

For example, antagonists of retinol binding to RBP are used in the methods, compounds, and compositions disclosed herein. An antagonist of retinol binding to RBP includes compounds of Formula (I) or (II) which compete with the binding of retinol to RBP.

As mentioned above, one means by which RBP binding to retinol is modulated is to competitively bind compounds of Formula (I) or (II). Therefore, one embodiment of the methods and compositions disclosed herein provides for lowering RBP levels or activity via compounds having the structure of Formula

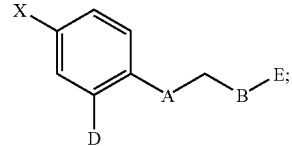

Formula (I)

wherein:

A is O, NH, or S;

B is a bond, —($C_2$-$C_7$)alkyl, —($C_2$-$C_7$)alkenyl, —($C_3$-$C_8$)cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;

D is isopropyl, isobutyl, sec-butyl, tert-butyl, cyclopropyl, cyclobutyl, cyclopentyl, methylenecyclopropyl, methylenecyclobutyl, methylenecyclopentyl;

E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;

R is H, an optionally substituted aryl, or an optionally substituted heteroaryl;

X is a halogen;

or an active metabolite, or a pharmaceutically acceptable prodrug, salt, or solvate thereof, wherein the compound of Formula (I) modulates RBP levels or activity;

Another embodiment of the methods and compositions disclosed herein provides for lowering RBP levels or activity via compounds having the structure of Formula (II):

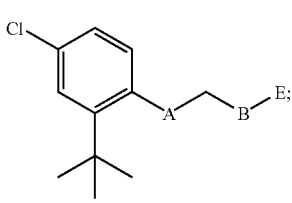

Formula (II)

wherein:

A is O, NH, or S;

B is a bond, —(C$_2$-C$_7$)alkyl, —(C$_2$-C$_7$)alkenyl, —(C$_3$-C$_8$)cycloalkyl, —(C$_2$-C$_7$)heteroalkyl, —(C$_3$-C$_8$)heterocycloalkyl, —(C$_3$-C$_8$)cycloalkenyl, —(C$_3$-C$_8$)heterocycloalkenyl;

E is (C=O)—OR, —O—(C=O)—R, —(C=O)—R, —OR, a carboxylic acid bioisostere, —(C=O)—NR$^1$R, NR$^1$—(C=O)—R, —(C$_1$-C$_7$)alkyl-(C=O)—OR, or —(C$_1$-C$_7$)alkyl-(C=O)—NR$^1$R;

R is H or

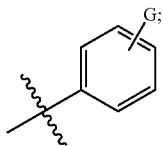

G is —OR$^1$, —(C$_1$-C$_6$)alkyl, —(C$_1$-C$_6$)alkyl-OR$^1$, halogen, —CO$_2$R$^1$, —(C$_1$-C$_6$)alkyl-CO$_2$R$^1$, NHR$^1$, —(C$_1$-C$_6$)alkyl-NHR$^1$, —(C=O)NHR$^1$, —(C$_1$-C$_6$)alkyl-(C=O)NHR$^1$, —NHR$^1$(C=O)R$^1$, —(C$_1$-C$_6$)alkyl-NHR$^1$(C=O)R$^1$;

R$^1$ is H or (C$_1$-C$_6$)alkyl;

or an active metabolite, or a pharmaceutically acceptable prodrug, salt, or solvate thereof, wherein the compound of Formula (II) modulates RBP levels of activity.

Detection of Modulator Activity

In some embodiments, the compounds and compositions disclosed herein are also be used in assays for detecting perturbations in RBP or TTR availability through conventional means. For example, a subject is treated with any of the compounds or compositions disclosed herein, and RBP or TTR levels quantified using conventional assay techniques. See Sundaram, M., et al., Biochem. J. 362:265-271 (2002). For example, a typical non-competitive sandwich assay is an assay disclosed in U.S. Pat. No. 4,486,530, incorporated herein by reference. In this method, a sandwich complex, for example an immune complex, is formed in an assay medium. The complex comprises the analyte, a first antibody, or binding member, that binds to the analyte and a second antibody, or binding member that binds to the analyte or a complex of the analyte and the first antibody, or binding member. Subsequently, the sandwich complex is detected and is related to the presence and/or amount of analyte in the sample. The sandwich complex is detected by virtue of the presence in the complex of a label wherein either or both the first antibody and the second antibody, or binding members, contain labels or substituents capable of combining with labels. For example, the sample is plasma, blood, feces, tissue, mucus, tears, saliva, or urine, for example for detecting modulation of clearance rates for RBP or TTR. For a more detailed discussion of this approach see U.S. Pat. Nos. Re 29,169 and 4,474,878, the relevant disclosures of which are incorporated herein by reference.

In a variation of the above sandwich assay, the sample in a suitable medium is contacted with labeled antibody or binding member for the analyte and incubated for a period of time. Then, the medium is contacted with a support to which is bound a second antibody, or binding member, for the analyte. After an incubation period, the support is separated from the medium and washed to remove unbound reagents. The support or the medium is examined for the presence of the label, which is related to the presence or amount of analyte. For a more detailed discussion of this approach see U.S. Pat. No. 4,098,876, the relevant disclosure of which is incorporated herein by reference.

In some embodiments, the modulators disclosed herein are also used in in vitro assays for detecting perturbations in RBP or TTR activity. For example, the modulator is added to a sample comprising RBP, TTR and retinol to detect complex disruption. A component, for example, RBP, TTR, retinol or the modulator, is labeled to determine if disruption of complex formation occurs. For example, complex formation and subsequent disruption is detected and/or measured through conventional means, such as the sandwich assays disclosed above. Other detection systems are also used to detect modulation of RBP or TTR binding, for example, FRET detection of RBP-TTR-retinol complex formation. See U.S. Provisional Patent Application No. 60/625,532 "Fluorescence Assay for Modulators of Retinol Binding," herein incorporated by reference.

In addition, other potential modulators which include, but are not limited to, small molecules, polypeptides, nucleic acids and antibodies, are also screened using the in vitro detection methods described above. For example, the methods and compositions described herein is used to screen small molecule libraries, nucleic acid libraries, peptide libraries or antibody libraries in conjunction with the teachings disclosed herein. Methods for screening libraries, such as combinatorial libraries and other libraries disclosed above, are found, for example, in U.S. Pat. Nos. 5,591,646; 5,866,341; and 6,343,257, which are hereby incorporated by reference.

In Vivo Detection of Modulator Activity

In addition to the in vitro methods disclosed above, in some embodiments, the methods and compositions disclosed herein are used in conjunction with in vivo detection and/or quantitation of modulator activity on TTR or RBP availability. For example, labeled TTR or RBP is injected into a subject, wherein a candidate modulator added before, during or after the injection of the labeled TTR or RBP. The subject is a mammal, for example a human; however other mammals, such as primates, horse, dog, sheep, goat, rabbit, mice or rats are further examples. A biological sample is then removed from the subject and the label detected to determine TTR or RBP availability. A biological sample includes, but is not limited to, plasma, blood, urine, feces, mucus, tissue, tears or saliva. Detection of the labeled reagents disclosed herein takes place using any of the conventional means, depending upon the nature of the label. Examples of monitoring devices for chemiluminescence, radiolabels and other labeling compounds are found in U.S. Pat. Nos. 4,618,485; 5,981,202, the relevant disclosures of which are herein incorporated by reference.

Hyperretinolemia

Retinol is a fat-soluble, antioxidant vitamin. At proper levels, retinol is important in vision and bone growth but can be problematic if they are present in excess. Hyperretinolemia is the presence of elevated or abnormal levels of retinol in the blood and is thought to be related to diseases and conditions such as Type I and Type II diabetes, hyperostosis, such as, diffuse idiopathic skeletal hyperostosis (DISH), and vitreoretinal diseases, such as macular degeneration. The methods, compounds, and compositions described herein, which reduce the level of retinol in the blood are used to treat such diseases and conditions. Also, the methods, compounds, and compositions, presented herein, are effective in reducing retinol availability in target organs and tissues such as the eye. By reducing retinol concentrations in the blood the availability of retinol in organs such as the liver may modulate the formation of the retinol-retinol-binding protein complex and/ or formation of the retinol-retinol-binding protein-transthyretin complex. In one embodiment, is a method of treating a patient with hyperretinolemia comprising administering a therapeutically effective amount of a compound of Formula (I) or (II) wherein the compound of Formula (I) or (II) reduces the serum levels or activity of retinol.

Metabolic Disorders

Metabolic disorders, including Type I and Type II diabetes mellitus (obese and/or non-obese), have also been associated with abnormal retinol levels.

Type I Diabetes (Insulin-Dependent Diabetes Mellitus)

Type I diabetes is a severe form of diabetes. If left untreated, type I diabetes results in ketosis of the patient and rapid degeneration. Approximately 10-20% of diabetic patients are classified as type I, comprising mainly young individuals. Non-obese adults also comprise type I diabetic patients, although at fewer numbers.

Type I diabetes is a catabolic disorder, where circulating levels of insulin are virtually absent and plasma glucagon levels elevated. Type I diabetes is believed to have auto-immune origins, possibly resulting from an infectious or toxic environmental insult to the pancreatic B cells in affected individuals. In support of the auto-immune theory, autoantibodies to insulin and islet cells have been detected in type I diabetes patients, as compared to non-diabetic individuals.

Lower levels of retinol, with observed decreases in retinol binding protein (RBP) levels and increased urinary excretion of RBP, has been correlated with type I diabetes in juveniles. See Basu, T K, et al. Am. J. Clin. Nutr. 50:329-331 (1989); Durbey, S W et al., Diabetes Care 20:84-89 (1997). The lower levels of retinol and RBP are accompanied by a concomitant decrease in zinc metabolism, a factor necessary for the synthesis of RBP in hepatic cells. See Cunningham, J J, et al. Metabolism 42:1558-1562 (1994). In contrast, tocopherol, or vitamin E levels, are unchanged in type I diabetic patients. See Basu, T K et al (1989).

The lower levels of retinol are observed despite elevated levels of vitamin A in hepatic storage cells. See Tuitoek P J, et al. Br. J. Nutr. 75: 615-622 (1996). Studies demonstrating the linkage between vitamin A status and insulin secretion show that only insulin treatment can relieve the suppressed levels of vitamin A in type I diabetic subjects. Tuitoek, P J et al., J. Clin. Biochem. Nutr. 19:165-169 (1996). In contrast, dietary supplementation of vitamin A does not normalize metabolic availability of vitamin A. Id.

These studies demonstrate the interconnection between vitamin A and insulin regulation of glucose transport into muscle and adipocyte cells. Further studies have strengthened this interconnection by demonstrating the requirement of vitamin A for normal insulin secretion. See Chertow, B S, et al., J. Clin. Invest. 79:163-169 (1987). Retinol was shown to be necessary for insulin release from vitamin A-deficient perfused islet cells. Id. In vivo experiments demonstrated that vitamin-A deficient rats had impaired glucose-induced acute insulin release, which only improved with vitamin A repletion. Id. Vitamin A may exert its effects on insulin secretion through activation of transglutaminase activity in islet and insulin-secreting cells, see Driscoll H K, et al., Pancreas 15:69-77 (1997), and is needed for fetal islet development and prevention of glucose intolerance in adults, see Matthews, K A et al., J. Nutr. 134:1958-1963 (2004), further strengthening the role of vitamin A and retinol in insulin release and regulation of blood glucose levels in diabetic patients. Presented herein are methods, compounds, and compositions, for the treatment of Type I diabetes using a compound of Formula (I) and (II) wherein the levels or activity of retinol and/or RBP are modulated.

Type II Diabetes (Non-Insulin Dependent Diabetes Mellitus)

Type II diabetes comprises a heterogeneous group of the milder forms of diabetes. Type II diabetes usually occurs in adults, but occasionally may have its onset in childhood.

Type II diabetics classically exhibit insulin insensitivity in response to elevated plasma glucose levels. Up to 85% of type II diabetics are obese, having an insensitivity to endogenous insulin that is positively correlated with the presence of an abdominal distribution of fat. Causes of insulin insensitivity are linked with post-receptor defect in insulin action. This is associated with over distended cellular storage depots (e.g. distended adipocytes and over nourished liver and muscle cells) and a reduced ability to clear nutrients from the circulation after meals. The subsequent hyperinsulinism can also result in a further down-regulation of cellular insulin receptors. Furthermore, glucose transporter proteins (e.g. GLUT4) are also down-regulated upon continuous activation, leading to an aggravation of hyperglycemic conditions in patients.

In contrast to type I diabetes, type II diabetic patients exhibit elevated levels of RBP selectively, with normal to increased levels of retinol observed. See Sasaki, H et al., "Am. J. Med. Sci. 310:177-82 (1995); Basualdo C G, et al. J. Am. Coll. Nutr. 16:39-45 (1997); Abahausain, M A et al., Eur. J. Clin. Nutr. 53: 630-635 (1999). Retinoic acid (all trans RA and 13-cis RA) levels were also decreased in patients with type II diabetes. Yamakoshi, Y et al., Biol. Pharm. Bull 25:1268-1271 (2002). Levels of other vitamins, including vitamin E (tocopherol) and carotenoids were unchanged in both diabetic and control groups, as well as levels of zinc, albumin and TTR, which influence vitamin A metabolism. Id.

This selective increase in RBP levels in type II diabetics, combined with the selective decrease of RBP in type I diabetics, supports the role of RBP and vitamin A in insulin control of blood glucose levels. The increased RBP levels have been attributed to the increased insulin levels (hyperinsulinemia) in diabetic patients. Basualdo et al. (1997). RBP levels have also been linked to the severity of hyperglycemia in patients. Id. Retinoids have previously been shown to increase insulin sensitivity in humans. See Hartmann, D. et al. Eur. J. Clin. Pharmacol. 42:523-8 (1992). The inverse correlation of RBP levels with insulin sensitivity in type I and type II diabetics indicates a therapeutic means of controlling insulin sensitivity in mammalian subjects.

Retinol Binding Protein 4 (RBP 4)

Retinol binding protein 4 (RBP4) is an adipocyte-secreted protein recognized for its role in the transport of vitamin A. Studies have shown that elevated levels of serum RBP4 can help indicate an early stage development of insulin resistance, a major cause of type II diabetes. See Kahn et al., 354 New Eng. J. Med. 2552-63 (2006). Experiments in mice also suggest that elevated RBP4 levels cause insulin resistance. Moreover, serum RBP4 levels correlate with the magnitude of insulin resistance in subjects with obesity impaired glucose tolerance, or type II diabetes and in non-obese, non-diabetic subjects with a strong family history of type II diabetes. Elevated serum RBP4 has been associated with components of the metabolic syndrome, including increased body-mass index, waist-to-hip ratio, serum triglyceride levels, and systolic blood pressure and decreased high-density lipoprotein cholesterol levels.

Research also suggests that the amount of RBP4 in the blood reflects the amount of fat surrounding the abdominal organs indicating that RBP4 might be used as a biomarker for cardiovascular risk. As levels of RBP4 increase so do the levels of "inter-abdominal fat" linked to an increased risk for heart diseases and type II diabetes, since increased "inter-abdominal fat" is associated with cardiovascular risk. Studies also show that the gene expression of RBP4 increases more in visceral adipose tissue—the adipose tissue surrounding the internal organs—than it is in the subcutaneous adipose tissue. Thus, levels of RPB4 are higher in humans who have a "visceral pattern" of obesity compared with people that have a subcutaneous pattern of obesity.

Presented herein are compounds of Formula (I) and (II) that reduce excess serum levels of RBP4. In one embodiment is a compound of Formula (I):

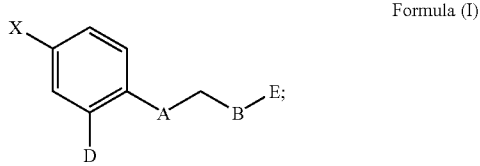

Formula (I)

wherein:
A is O, NH, or S;
B is a bond, —$(C_2$-$C_7)$alkyl, —$(C_2$-$C_7)$alkenyl, —$(C_3$-$C_8)$cycloalkyl, —$(C_2$-$C_7)$heteroalkyl, —$(C_3$-$C_8)$heterocycloalkyl, —$(C_3$-$C_8)$cycloalkenyl, —$(C_3$-$C_8)$heterocycloalkenyl;
D is isopropyl, isobutyl, sec-butyl, tert-butyl, cyclopropyl, cyclobutyl, cyclopentyl, methylenecyclopropyl, methylenecyclobutyl, methylenecyclopentyl;
E is (C=O)—OR, —O—(C=O)—R, —(C=O)—R, —OR, a carboxylic acid bioisostere, —(C=O)—$NR^1R$, $NR^1$—(C=O)—R, —$(C_1$-$C_7)$alkyl-(C=O)—OR, or —$(C_1$-$C_7)$alkyl-(C=O)—$NR^1R$;
R is H or

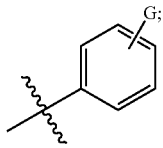

G is —$OR^1$, —$(C_1$-$C_6)$alkyl, —$(C_1$-$C_6)$alkyl-$OR^1$, halogen, —$CO_2R^1$, —$(C_1$-$C_6)$alkyl-$CO_2R^1$, $NHR^1$, —$(C_1$-$C_6)$alkyl-$NHR^1$, —(C=O)$NHR^1$, —$(C_1$-$C_6)$alkyl-(C=O)$NHR^1$, —$NHR^1$(C=O)$R^1$, —$(C_1$-$C_6)$alkyl-$NHR^1$(C=O)$R^1$;
$R^1$ is H or $(C_1$-$C_6)$alkyl;
X is a halogen;
or an active metabolite, or a pharmaceutically acceptable prodrug, salt, or solvate thereof,
wherein the compound of Formula (I) reduces the serum levels of RBP4.

In another embodiment is a compound of Formula (II):

Formula (II)

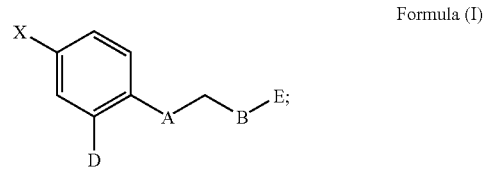

wherein:
A is O, NH, or S;
B is a bond, —$(C_2$-$C_7)$alkyl, —$(C_2$-$C_7)$alkenyl, —$(C_3$-$C_8)$cycloalkyl, —$(C_2$-$C_7)$heteroalkyl, —$(C_3$-$C_8)$heterocycloalkyl, —$(C_3$-$C_8)$cycloalkenyl, —$(C_3$-$C_8)$heterocycloalkenyl;
E is (C=O)—OR, —O—(C=O)—R, —(C=O)—R, —OR, a carboxylic acid bioisostere, —(C=O)—$NR^1R$, $NR^1$—(C=O)—R, —$(C_1$-$C_7)$alkyl-(C=O)—OR, or —$(C_1$-$C_7)$alkyl-(C=O)—$NR^1R$;
R is H or

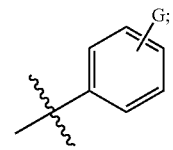

G is —$OR^1$, —$(C_1$-$C_6)$alkyl, —$(C_1$-$C_6)$alkyl-$OR^1$, halogen, —$CO_2R^1$, —$(C_1$-$C_6)$alkyl-$CO_2R^1$, $NHR^1$, —$(C_1$-$C_6)$alkyl-$NHR^1$, —(C=O)$NHR^1$, —$(C_1$-$C_6)$alkyl-(C=O)$NHR^1$, —$NHR^1$(C=O)$R^1$, —$(C_1$-$C_6)$alkyl-$NHR^1$(C=O)$R^1$;
$R^1$ is H or $(C_1$-$C_6)$alkyl;
or an active metabolite, or a pharmaceutically acceptable prodrug, salt, or solvate thereof,
wherein the compound of Formula (II) reduces the levels of serum RBP4.

In yet another embodiment is a method for treating diabetes in a patient comprising administering to the patient a therapeutically effective amount of a compound of Formula (II):

Formula (I)

wherein:
A is O, NH, or S;
B is a bond, —$(C_2$-$C_7)$alkyl, —$(C_2$-$C_7)$alkenyl, —$(C_3$-$C_8)$cycloalkyl, —$(C_2$-$C_7)$heteroalkyl, —$(C_3$-$C_8)$heterocycloalkyl, —$(C_3$-$C_8)$cycloalkenyl, —$(C_3$-$C_8)$heterocycloalkenyl;
D is isopropyl, isobutyl, sec-butyl, tert-butyl, cyclopropyl, cyclobutyl, cyclopentyl, methylenecyclopropyl, methylenecyclobutyl, methylenecyclopentyl;
E is (C=O)—OR, —O—(C=O)—R, —(C=O)—R, —OR, a carboxylic acid bioisostere, —(C=O)—$NR^1R$, $NR^1$—(C=O)—R, —$(C_1$-$C_7)$alkyl-(C=O)—OR, or —$(C_1$-$C_7)$alkyl-(C=O)—$NR^1R$;
R is H, an optionally substituted aryl, or an optionally substituted heteroaryl;
X is a halogen;
or an active metabolite, or a pharmaceutically acceptable prodrug, salt, or solvate thereof,
wherein administering a therapeutically effective amount of the compound of Formula (I) lowers the levels of RBP4. In yet another embodiment is a method for treating ophthalmic conditions in a patient, such as by way of example only, macular degeneration, comprising administering to the patient a therapeutically effective amount of a compound of Formula (I) or (II) wherein the level of RBP4 is reduced. In a further embodiment is a method for lowering RBP4 in serum comprising administering a compound of Formula (I) or (II). In yet a further embodiment is a method for lowering RBP4 in tissue, such as by way of example only, adipose tissue, comprising administering a compound of Formula (I) or (II).

In one embodiment is a method for treating type I or type II diabetes in a patient comprising administering to the patient a therapeutically effective amount of a compound of Formula (I) or (II) wherein the therapeutically effective amount of the compound of Formula (I) or (II) modulates RBP4 in adipose tissue. In a further embodiment is a method for treating type I or type II diabetes in a patient comprising administering to the patient a therapeutically effective amount of a compound of Formula (I) or (II) wherein levels of RBP4 are reduced such that reduction in RBP4 levels increases insulin sensitization. In another embodiment is a method for treating type I or type II diabetes in a patient comprising administering to the patient a therapeutically effective amount of a compound of Formula (II):

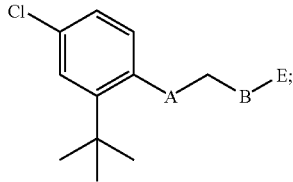

Formula (II)

wherein:

A is O, NH, or S;

B is a bond, —($C_2$-$C_7$)alkyl, —($C_2$-$C_7$)alkenyl, —($C_3$-$C_8$)cycloalkyl, —($C_2$-$C_7$)heteroalkyl, —($C_3$-$C_8$)heterocycloalkyl, —($C_3$-$C_8$)cycloalkenyl, —($C_3$-$C_8$)heterocycloalkenyl;

E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;

R is H, an optionally substituted aryl, or an optionally substituted heteroaryl;

or an active metabolite, or a pharmaceutically acceptable prodrug, salt, or solvate thereof, wherein levels of RBP4 are reduced such that reduction in RBP4 levels increases insulin sensitization.

Idiopathic Intracranial Hypertension (IIH)

IIH, also known as pseudotumor cerebri (PTC), is a condition of high pressure in the fluid around the brain without an identifiable causative agent. The condition exists mostly in women in their childbearing years. The symptoms often start or worsen during a period of weight gain. Typical symptoms include headaches, pulse synchronous tinnitus and visual problems (papilledema), which may lead to severe and permanent visual loss in untreated cases.

Although the etiology of IIH is unknown, excess vitamin A levels are a candidate because the symptoms and signs of hypervitaminosis A mimic those of IIH. Studies have shown that serum retinol levels are significantly higher in patients with IIH than in control groups, despite the showing of no significant differences in vitamin A ingestion or retinyl ester concentration in both groups. See Jacobson, D M et al., Neurology, 54:2192-3 (1999). Included herein, are methods, compounds, and compositions for the treatment of IIH using compounds of Formula (I) and (II).

Bone-Related Disorders

Hyperostosis is a condition where an excessive growth of bone occurs. This condition may lead to formation of a mass projecting from a normal bone, seen in numerous musculoskeletal disorders. Diffuse idiopathic skeletal hyperostosis (DISH) is a form of hyperostosis, characterized by flowing calcification and ossification of vertebral bodies. Radiographic abnormalities in DISH patients are observed most commonly in the thoracic spine, leading to the presence of a radiodense shield in front of the vertebral column. Ossification of the posterior longitudinal ligament (OPLL) is also associated with increased frequency in patients with DISH, in addition to cervical cord compromise as a result of hyperostosis or ossification of spinal ligaments. Other disorders accompanying hyperostosis or DISH patients includes acute fracture and pseudoarthrosis of the spine.

Although the pathogenesis of DISH and OPLL are presently unknown, both disorders have been associated with high levels of serum retinol and RBP. See Kodama, T et al., In vivo 12:339-344 (1998); Kilcoyne, R F, J. Am. Acad. Dermatol. 19:212-216 (1988), suggesting a possible role for vitamin A in the pathogenesis of DISH and OPLL. Other studies have shown the occurrence of congenital functional RBP deficiency with abnormal levels of retinol and RBP levels in a hyperostosis patient. De Bandt, M., et al., J. Rheumatol. 22:1395-8 (1995). Medical accounts also report the occurrence of hypervitaminosis A with degenerative joint disease in an elderly patient. See Romero, J B et al., Bull Hosp. Jt. Dis. 54:169-174 (1996). Thus, the methods, compounds, and compositions described herein are used to treat bone-related disorders, such as, by way of example only, hyperostosis, using compounds of Formula (I) or (II) wherein the level of serum retinol and RBP are modulated.

Protein Misfolding and Aggregation Diseases

Protein misfolding and aggregation has been linked to several diseases, generally known as the amyloidoses, including Alzeheimer's disease, Parkinson's disease and systemic amyloidosis. These diseases occur with misfolding of the secondary protein structure, in which a normally soluble protein forms insoluble extracellular fibril deposits of β-sheet-rich structures referred to as amyloid fibrils, which causes organ dysfunction. Twenty different fibril proteins, including transthyretin (TTR), have been described in human amyloidosis, each with a different clinical picture.

Wild-type TTR proteins are involved in the development of senile systemic amyloidosis, a sporadic disorder resulting from the deposition of TTR fibrils in cardiac tissues. Mutant TTR proteins, in contrast, are associated with familial amyloidotic polyneuropathy and cardiomyopathy, which deposits primarily affect the peripheral and autonomic nervous system, and heart. The mechanisms responsible for tissue selectivity deposition are currently unknown. In amyloidosis formation, TTR associates with fibril formation in its monomer form. Compounds which promote stabilization of TTR tetramers, such as the small molecules resveratrol and biarylamine, inhibit amyloid fibril formation in vitro. See Reixach, N. et al., PNAS 101:2817-2822 (2004).

Transthyretin is also implicated in Alzheimer's disease, but in contrast to the formation of amyloid fibrils in amyloidosis, TTR inhibits amyloid beta protein formation both in vitro and in vivo. See Schwartzman, A L et al., Amyloid. 11: 1-9 (2004); Stein, T D and Johnson, J A, J. Neurosci. 22:7380-7388 (2002). Vitamin A also has been shown to exhibit anti-amyloidogenic and amyloid-beta fibril destabilizing effects in vitro. See Ono, K., et al., Exp. Neurol. 189:380-392 (2004).

Cystic Fibrosis

Cystic fibrosis is a lethal hereditary disease wherein the primary cause of mortality is due to excessive lung inflammation associated with recurrent bacterial infections by *Pseudomonas aeruginosa*. Cystic fibrosis is caused by a mutation in the cystic fibrosis transmembrane conductance regulator gene (CFTR). The product of this gene is a chloride ion channel important in creating sweat, digestive juices, and mucus. The CFTR gene is located at the q31.2 locus of chromosome 7 and creates a protein which is 1,480 amino acids long. A common mutation, ΔF508, is the deletion of three nucleotides that results in a loss of the amino acid phenylalanine at the 508 position of the protein. Subsequently, ΔF508 creates a protein which does not fold normally and is degraded by the cell. Also, the protein created by the CFTR gene acts as a chloride channel connecting the cytoplasm to the surrounding fluid. Mutation of the CFTR protein traps chloride ions outside the cell. Exclusion of chloride ions into the cytoplasm attracts sodium ions and this combination forms a salt which is lost in high amounts in the sweat of individuals with cystic fibrosis. Some studies suggest that the CFTR protein failure leads to an increase in sodium and chloride uptake which increases water reabsorption, thereby causing dehydration and thick mucus.

Treatment of cystic fibrosis is concentrated on the treatment of lung damage caused by thick mucus and infection. Antibiotics such as vancomycin and tobramycin are used when there has been a decline in lung function. Nasal steroids such as fluticasone have been employed to decrease nasal inflammation. In other cases, sinus surgery is used to alleviate nasal obstruction and limit further infections.

The regulation of ceramide levels appears to be important for efficient clearance of bacteria from infected lungs. Presented herein are methods for treating cystic fibrosis comprising administering a compound of Formula (I) or Formula (II) wherein the compound aids in the clearance of bacterial burden through the mediation of ceramide production. In some embodiments are methods for treating bacterial infections related to cystic fibrosis comprising administering compounds of Formula (I) or Formula (II) wherein the compound of Formula (I) or Formula (II) assists in the clearance of bacteria from infected lungs. In other embodiments, the bacteria is a gram-negative bacteria. In further embodiments the gram-negative bacteria is *pseudomonas aeruginosa*. In another embodiment is a method for treating cystic fibrosis comprising administering a compound of Formula (I) or Formula (II) wherein the compound of Formula (I) or (II) corrects the ceramide deficiency in cystic fibrosis related organs. In yet other embodiments, the cystic fibrosis related organ is the lungs.

Alström-Hallgren Syndrome

Alström-Hallgren syndrome (also known as Alström syndrome) is a rare autosomal recessive disorder affecting children at a very early age. Symptoms include blindness or severe vision impairment in infancy associated with cone-rod dystrophy, deafness, obesity onset during the first year, development of type II diabetes mellitus and severe insulin resistance, acanthosis nigricans (development of dark patches of skin) hypergonadotrophic hypogonadism and thyroid deficiencies.

Mutations linked to Alström syndrome were localized to a 14.9 cM region on chromosome 2p. Collin, G B et al., Hum. Mol. Gen. 6:213-219 (1997). Other than treating individual symptomatic manifestations of the disease, there are currently no therapeutic treatments available for Alström syndrome patients. In some embodiments are methods, compounds, and compositions used in the treatment of Alström-Hallgren syndrome using compounds having the structure of Formula (I) and (II).

Definitions

An "alkoxy" group refers to an (alkyl)O— group, where alkyl is as defined herein.

An "alkyl" group refers to an aliphatic hydrocarbon group. The alkyl moiety includes a "saturated alkyl" group, which means that it does not contain any alkene or alkyne moieties. The alkyl moiety includes an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, includes branched, straight chain, or cyclic.

The "alkyl" moiety includes moieties with 1 to 10 carbon atoms (whenever it appears herein, a numerical range such as "1 to 10" refers to each integer in the given range; e.g., "1 to 10 carbon atoms" means that the alkyl group consists of 1 carbon atom, 2 carbon atoms, 3 carbon atoms, etc., up to and including 10 carbon atoms, although the present definition also covers the occurrence of the term "alkyl" where no numerical range is designated). The alkyl group could also be a "lower alkyl" having 1 to 5 carbon atoms. The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

The term "alkenyl" refers to a type of alkyl group in which the first two atoms of the alkyl group form a double bond that is not part of an aromatic group. That is, an alkenyl group begins with the atoms —C(R)═C—R, wherein R refers to the remaining portions of the alkenyl group, which is either the same or different. Non-limiting examples of an alkenyl group include —CH═CH, —C(CH$_3$)═CH, —CH═CCH$_3$ and —C(CH$_3$)═CCH$_3$. The alkenyl moiety includes branched, straight chain, or cyclic (in which case, it is also known as a "cycloalkenyl" group).

An "amide" is a chemical moiety with formula —C(O)NHR or —NHC(O)R, where R is selected from the group consisting of alkyl, cycloalkyl, aryl, heteroaryl (bonded through a ring carbon) and heteroalicyclic (bonded through a ring carbon). An amide includes an amino acid or a peptide molecule attached to a compound of Formula (I), thereby forming a prodrug. Any amine, hydroxy, or carboxyl side chain on the compounds described herein can be amidified. The procedures and specific groups to make such amides are found in reference sources such as Greene and Wuts, Protective Groups in Organic Synthesis, 3$^{rd}$ Ed., John Wiley & Sons, New York, N.Y., 1999, which is incorporated herein by reference.

The term "aromatic" or "aryl" refers to an aromatic group which has at least one ring having a conjugated pi electron system and includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon.

The term "cycloalkyl" refers to a monocyclic or polycyclic radical that contains only carbon and hydrogen, and includes saturated, partially unsaturated, or fully unsaturated. Cycloalkyl groups include groups having from 3 to 10 ring atoms. Illustrative examples of cycloalkyl groups include the following moieties:

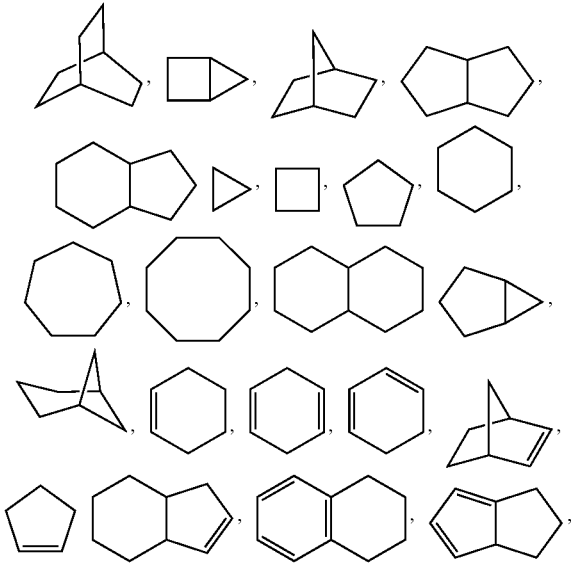

and the like.

The term "halo" or, alternatively, "halogen" means fluoro, chloro, bromo or iodo. Preferred halo groups are fluoro, chloro and bromo.

The terms "heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. The polycyclic heteroaryl group includes fused or non-fused. Illustrative examples of heteroaryl groups include the following moieties:

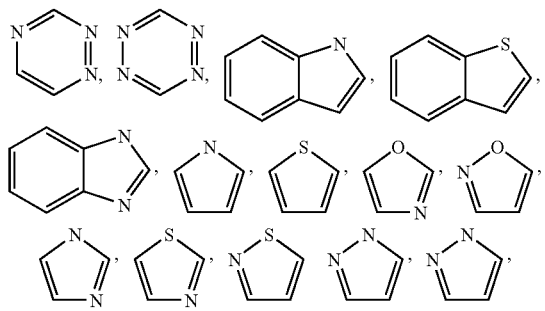

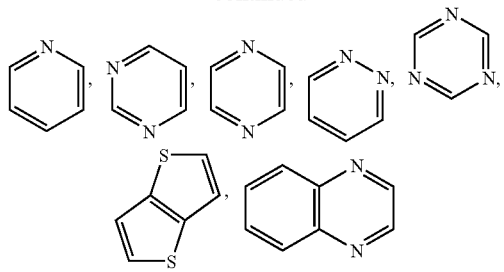

and the like.

The term "moiety" refers to a specific segment or functional group of a molecule. Chemical moieties are often recognized chemical entities embedded in or appended to a molecule.

The term "bond" or "single bond" refers to a chemical bond between two atoms, or two moieties when the atoms joined by the bond are considered to be part of larger substructure.

The term "carboxylic acid bioisostere" means a moiety that can replace a carboxylic acid group. The bioisostere contains an exchange of an atom or groups of atoms with another, broadly similar, atom or groups of atoms and maintains similar biological activity by mimicking the spatial arrangement, electronic properties, or some other physicochemical property of the carboxylic acid group. Thus, for example, tetrazole, sulfonic acid, and sulfonamide are carboxylic acid bioisosteres.

The term "optionally substituted" means that the referenced group includes substituted with one or more additional group(s) individually and independently selected from alkyl, cycloalkyl, aryl, heteroaryl, heteroalicyclic, hydroxy, alkoxy, aryloxy, mercapto, alkylthio, arylthio, cyano, halo, carbonyl, thiocarbonyl, isocyanato, thiocyanato, isothiocyanato, nitro, perhaloalkyl, perfluoroalkyl, silyl, and amino, including mono- and di-substituted amino groups, and the protected derivatives thereof. Examples of protecting groups are found in references such as Greene and Wuts, above.

In some embodiments, the compounds presented herein possess one or more chiral centers and each center in the R or S configuration. The compounds presented herein include all diastereomeric, enantiomeric, and epimeric forms as well as the appropriate mixtures thereof. Stereoisomers are obtained, if desired, for example, by the separation of stereoisomers by chiral chromatographic columns.

The methods and formulations described herein include the use of N-oxides, crystalline forms (also known as polymorphs), or pharmaceutically acceptable salts of compounds having the structure of Formula (I), as well as active metabolites of these compounds having the same type of activity. In some situations, compounds exist as tautomers. All tautomers are included within the scope of the compounds presented herein. In addition, the compounds described herein exist in unsolvated as well as solvated forms with pharmaceutically acceptable solvents such as water, ethanol, and the like. The solvated forms of the compounds presented herein are also considered to be disclosed herein.

Pharmaceutical Compositions

Another aspect are pharmaceutical compositions comprising a compound of Formula (I) or (II) and a pharmaceutically acceptable diluent, excipient, or carrier.

The term "pharmaceutical composition" refers to a mixture of a compound of Formula (I) with other chemical components, such as carriers, stabilizers, diluents, dispersing agents, suspending agents, thickening agents, and/or excipients. The pharmaceutical composition facilitates administration of the compound to an organism. Techniques of administering a compound include: intravenous, oral, aerosol, parenteral, ophthalmic, pulmonary and topical administration.

The term "carrier" refers to relatively nontoxic chemical compounds or agents that facilitate the incorporation of a compound into cells or tissues.

The term "diluent" refers to chemical compounds that are used to dilute the compound of interest prior to delivery. Diluents are also used to stabilize compounds because they provide a more stable environment. Salts dissolved in buffered solutions (which also provide pH control or maintenance) are utilized as diluents, including, but not limited to a phosphate buffered saline solution.

The term "physiologically acceptable" refers to a material, such as a carrier or diluent, which does not abrogate the biological activity or properties of the compound, and is nontoxic.

The term "pharmaceutically acceptable salt" refers to a formulation of a compound that does not cause significant irritation to an organism to which it is administered and does not abrogate the biological activity and properties of the compound. In one example, pharmaceutically acceptable salts are obtained by reacting a compound of Formula (I) with acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts are also obtained by reacting a compound of Formula (I) with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

A "metabolite" of a compound disclosed herein is a derivative of that compound that is formed when the compound is metabolized. The term "active metabolite" refers to a biologically active derivative of a compound that is formed when the compound is metabolized. The term "metabolized" refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism is obtained from The Pharmacological Basis of Therapeutics, 9th Edition, McGraw-Hill (1996).

In some embodiments, metabolites of the compounds disclosed herein are identified either by administration of compounds to a host and analysis of tissue samples from the host, or by incubation of compounds with hepatic cells in vitro and analysis of the resulting compounds.

A "prodrug" refers to an agent that is converted into the parent drug in vivo. Prodrugs are often useful because, in some situations, they are easier to administer than the parent drug. In some examples, they are, for instance, bioavailable by oral administration whereas the parent is not. For example, the prodrug also has improved solubility in pharmaceutical compositions over the parent drug. An example, without limitation, of a prodrug is a compound of Formula (I) which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug is a short peptide (polyaminoacid) bonded to an acid group where the peptide is metabolized to reveal the active moiety.

In some embodiments, the compounds described herein are administered to a human patient per se, or in pharmaceutical compositions where they are mixed with other active ingredients, as in combination therapy, or suitable carrier(s) or excipient(s). Techniques for formulation and administration of the compounds of the instant application are found in "Remington: The Science and Practice of Pharmacy," 20th ed. (2000).

Routes of Administration

Suitable routes of administration are, for example, include oral, rectal, vaginal, transmucosal, transdermal, pulmonary, or intestinal administration; parenteral delivery, including intramuscular, subcutaneous, intravenous, intramedullary injections, as well as intrathecal, direct intraventricular, intraperitoneal, or intranasal injections.

Alternately, one administers the compound in a local rather than systemic manner, for example, via injection of the compound directly into an organ, often in a depot or sustained release formulation. The liposomes will be targeted to and taken up selectively by the organ. In addition, for example, the drug is provided in the form of a rapid release formulation, in the form of an extended release formulation, or in the form of an intermediate release formulation.

Composition/Formulation

For example, pharmaceutical compositions comprising a compound of Formula (I) or (II) are manufactured by means of mixing, dissolving, granulating, dragee-making, levigating, emulsifying, encapsulating, entrapping or compression processes.

For example, pharmaceutical compositions are formulated in conventional manner using one or more physiologically acceptable carriers comprising excipients and auxiliaries which facilitate processing of the active compounds into preparations which are used pharmaceutically. Proper formulation is dependent upon the route of administration chosen.

In some embodiments, the compounds of Formula (I) or (II) are administered in a variety of ways, including systemically, such as orally or intravenously.

Useful compositions also include solubilizing agents to aid in the solubility of a compound of Formula (I) or (II). The term "solubilizing agent" generally includes agents that result in formation of a micellar solution or a true solution of the agent. In some embodiments, certain acceptable nonionic surfactants, for example polysorbate 80, are useful as solubilizing agents, similarly, acceptable glycols, polyglycols, e.g., polyethylene glycol 400, and glycol ethers.

Useful compositions also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Useful compositions also include one or more acceptable salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful compositions also include one or more acceptable preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, aqueous suspension compositions are packaged in single-dose non-reclosable containers. Alternatively, multiple-dose reclosable containers are used, in which case it is typical to include a preservative in the composition.

A pharmaceutical carrier for the hydrophobic compounds of Formula (I) or (II) is a cosolvent system comprising benzyl alcohol, a nonpolar surfactant, a water-miscible organic polymer, and an aqueous phase. The cosolvent system includes a 10% ethanol, 10% polyethylene glycol 300, 10% polyethylene glycol 40 castor oil (PEG-40 castor oil) with 70% aqueous solution. This cosolvent system dissolves hydrophobic compounds well, and itself produces low toxicity upon systemic administration. For example, the proportions of a cosolvent system are varied considerably without destroying its solubility and toxicity characteristics. Furthermore, for example, the identity of the cosolvent components are varied: for example, other low-toxicity nonpolar surfactants are used instead of PEG-40 castor oil, the fraction size of polyethylene glycol 300 is varied; in some embodiments, other biocompatible polymers replace polyethylene glycol, e.g., polyvinyl pyrrolidone; and other sugars or polysaccharides may be included in the aqueous solution.

Alternatively, other delivery systems for hydrophobic pharmaceutical compounds are employed. Liposomes and emulsions are examples of delivery vehicles or carriers for hydrophobic drugs. In some embodiments, certain organic solvents such as N-methylpyrrolidone also are employed, although usually at the cost of greater toxicity. Additionally, the compounds for example, are delivered using a sustained-release system, such as semipermeable matrices of solid hydrophobic polymers containing the therapeutic agent. Sustained-release capsules, depending on their chemical nature, release the compounds for a few weeks up to over 100 days. Depending on the chemical nature and the biological stability of the therapeutic reagent, additional strategies for protein stabilization are employed.

All of the formulations described herein benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, compounds of Formula (I) or (II) are provided as salts with pharmaceutically compatible counterions. In some embodiments, pharmaceutically compatible salts are formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Oral Administration

In some embodiments, the pharmaceutical compositions provided herein are provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), in some embodiments, the pharmaceutical compositions contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. In some embodiments, the binder or filler are present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, impart properties to some compressed tablets that permit disintegration in the mouth by chewing. In some embodiments, such compressed tablets are used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation. In some embodiments, the pharmaceutical compositions provided herein contain from about 0.5 to about 15% or from about 1 to about 5% by weight of a disintegrant.

Suitable lubricants include, but are not limited to, calcium stearate; magnesium stearate; mineral oil; light mineral oil;

glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; *lycopodium*; silica or silica gels, such as AEROSIL® 200 (W.R. Grace Co., Baltimore, Md.) and CAB-O-SIL® (Cabot Co. of Boston, Mass.); and mixtures thereof. In some embodiments, the pharmaceutical compositions provided herein contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic acid, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

In some embodiments, pharmaceutical preparations which are used orally include push-fit capsules made of gelatin, including by way of example only, soft, sealed capsules made of gelatin and a plasticizer, such as glycerol or sorbitol; or hard-gel capsules or tablets. In some embodiments, the push-fit capsules contain the active ingredients in admixture with filler such as lactose, binders such as starches, and/or lubricants such as talc or magnesium stearate and, optionally, stabilizers. In some embodiments, soft capsules, the active compounds are dissolved or suspended in suitable liquids, such as fatty oils, liquid paraffin, or liquid polyethylene glycols. In addition, in some embodiments, stabilizers are added. All formulations for oral administration should be in dosages suitable for such administration.

For buccal or sublingual administration, in some embodiments, the compositions take the form of tablets, lozenges, or gels formulated in conventional manner.

It should be understood that in some embodiments, many carriers and excipients serve several functions, even within the same formulation.

In some embodiments, the pharmaceutical compositions provided herein are provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which beneficial in some embodiments, in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

In some embodiments, the tablet dosage forms are prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

In some embodiments, the pharmaceutical compositions provided herein are provided as soft or hard capsules, which are made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. In some embodiments, the soft gelatin shells contain a preservative to prevent the growth of microorganisms. Suitable preservatives are those as described herein, including methyl- and propyl-parabens, and sorbic acid. In some embodiments, the liquid, semisolid, and solid dosage forms provided herein are encapsulated in a capsule. Suitable liquid and semisolid dosage forms include solutions and suspensions in propylene carbonate, vegetable oils, or triglycerides. Capsules containing such solutions are prepared, for example, as described in U.S. Pat. Nos. 4,328,245; 4,409,239; and 4,410,545. In some embodiments, the capsules are coated in order to modify or sustain dissolution of the active ingredient.

In some embodiments, the pharmaceutical compositions provided herein are provided in liquid and semisolid dosage forms, including emulsions, solutions, suspensions, elixirs, and syrups. An emulsion is a two-phase system, in which one liquid is dispersed in the form of small globules throughout another liquid, which includes oil-in-water or water-in-oil. Emulsions include a pharmaceutically acceptable non-aqueous liquids or solvent, emulsifying agent, and preservative. Suspensions include a pharmaceutically acceptable suspending agent and preservative. Aqueous alcoholic solutions include a pharmaceutically acceptable acetal, such as a di(lower alkyl)acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and also contain a preservative. For a liquid dosage form, for example, a solution in a polyethylene glycol is diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations in some embodiments, further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

In some embodiments, the pharmaceutical compositions provided herein for oral administration are also provided in the forms of liposomes, micelles, microspheres, or nanosystems. In some embodiments, micellar dosage forms are prepared as described in U.S. Pat. No. 6,350,458.

In some embodiments, the pharmaceutical compositions provided herein are provided as non-effervescent or effervescent, granules and powders, to be reconstituted into a liquid dosage form. In some embodiments, pharmaceutically acceptable carriers and excipients used in the non-effervescent granules or powders include diluents, sweeteners, and wetting agents. In some embodiments, pharmaceutically acceptable carriers and excipients used in the effervescent granules or powders include organic acids and a source of carbon dioxide.

In some embodiments, coloring and flavoring agents are used in all of the above dosage forms.

In some embodiments, the pharmaceutical compositions provided herein are formulated as immediate or modified release dosage forms, including delayed-, sustained, pulsed-, controlled, targeted-, and programmed-release forms.

Parenteral Administration

In some embodiments, the pharmaceutical compositions provided herein are administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

In some embodiments, the pharmaceutical compositions provided herein are formulated in any dosage forms that are suitable for parenteral administration, including solutions, suspensions, emulsions, micelles, liposomes, microspheres, nanosystems, and solid forms suitable for solutions or suspensions in liquid prior to injection. In some embodiments, such dosage forms are prepared according to conventional methods (see, e.g., *Remington: The Science and Practice of Pharmacy*).

In some embodiments, the pharmaceutical compositions intended for parenteral administration include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including $\alpha$-cyclodextrin, $\beta$-cyclodextrin, hydroxypropyl-$\beta$-cyclodextrin, sulfobutylether-$\beta$-cyclodextrin, and sulfobutylether 7-$\beta$-cyclodextrin (CAPTISOL®, CyDex, Lenexa, Kans.).

In some embodiments, the pharmaceutical compositions provided herein are formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

In some embodiments, the pharmaceutical compositions provided herein are formulated as immediate or modified release dosage forms, including delayed-, sustained, pulsed-, controlled, targeted-, and programmed-release forms.

In some embodiments, the pharmaceutical compositions are formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In some embodiments, for intravenous injections, compounds of Formula (I) or (II) are formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations in some embodiments, include aqueous or nonaqueous solutions, preferably with physiologically compatible buffers or excipients.

The compounds in some embodiments, are formulated for parenteral administration by injection, e.g., by bolus injection or continuous infusion. Formulations for injection in some embodiments, are presented in unit dosage form, e.g., in ampoules or in multi-dose containers, with an added preservative. The compositions in some embodiments, take such forms as suspensions, solutions or emulsions in oily or aqueous vehicles, and contain formulatory agents such as suspending, stabilizing and/or dispersing agents.

Pharmaceutical formulations for parenteral administration include aqueous solutions of the active compounds in water-soluble form. Additionally, suspensions of the active compounds in some embodiments, are prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions, in some embodiments, contain substances which increase the viscosity of the suspension, such as sodium carboxymethyl cellulose, sorbitol, or dextran. Optionally, the suspension also contains suitable stabilizers or agents which increase the solubility of the compounds to allow for the preparation of highly concentrated solutions.

Alternatively, the active ingredient is in powder form for constitution with a suitable vehicle, e.g., sterile pyrogen-free water, before use.

The compounds in some embodiments, are formulated in rectal compositions such as rectal gels, rectal foam, rectal aerosols, suppositories or retention enemas, e.g., containing conventional suppository bases such as cocoa butter or other glycerides.

In addition to the formulations described previously, the compounds, in some embodiments, are formulated as a depot preparation. Such long acting formulations in some embodiments, are administered by implantation (for example subcutaneously or intramuscularly) or by intramuscular injection. Thus, for example, the compounds are formulated with suitable polymeric or hydrophobic materials (for example as an emulsion in an acceptable oil) or ion exchange resins, or as sparingly soluble derivatives, for example, as a sparingly soluble salt.

Injectable depot forms in some embodiments, are made by forming microencapsulated matrices (also known as microencapsule matrices) of the compound of Formula (I) or (II) in biodegradable polymers. Depending upon the ratio of drug to polymer and the nature of the particular polymer employed, the rate of drug release is controlled. Depot injectable formulations in some embodiments, are prepared by entrapping the drug in liposomes or microemulsions. By way of example only, posterior juxtascleral depots are used as a mode of administration for compounds having the structure of Formula (I) or (II). The sclera is a thin avascular layer, comprised of highly ordered collagen network surrounding most of vertebrate eye. Since the sclera is avascular it can be utilized as a natural storage depot from which injected material cannot rapidly removed or cleared from the eye. In some embodiments, the formulation used for administration of the compound into the scleral layer of the eye is any form suitable for application into the sclera by injection through a cannula with small diameter suitable for injection into the scleral layer. Examples for injectable application forms are solutions, suspensions or colloidal suspensions.

Topical Administration

The pharmaceutical compositions provided herein in some embodiments, are administered topically to the skin, orifices, or mucosa. The topical administration, as used herein, include (intra)dermal, conjunctival, intracorneal, intraocular, ophthalmic, auricular, transdermal, nasal, vaginal, uretheral, respiratory, and rectal administration.

The pharmaceutical compositions provided herein in some embodiments, are formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein in some embodiments, also comprise liposomes, micelles, microspheres, nanospheres or nanoparticles, and mixtures thereof.

Another useful formulation for administration of compounds having the structure of Formula (I) or (TI) employs transdermal delivery devices ("patches"). Such transdermal patches in some embodiments, are used to provide continuous or discontinuous infusion of the compounds of the presented herein in controlled amounts. An example of the construction and use of transdermal patches for the delivery of pharmaceutical agents is found in U.S. Pat. No. 5,023,252. Such patches in some embodiments, are constructed for continuous, pulsatile, or on demand delivery of pharmaceutical agents. Still further, in some embodiments, transdermal delivery of the compounds of Formula (I) or (II) is accomplished by means of iontophoretic patches and the like. Transdermal patches provide controlled delivery of the compounds. In some embodiments, the rate of absorption is slowed by using rate-controlling membranes or by trapping the compound within a polymer matrix or gel. Conversely, in some embodiments, absorption enhancers are used to increase absorption. In some embodiments, formulations suitable for transdermal administration are presented as discrete patches and are lipophilic emulsions or buffered, aqueous solutions, dissolved and/or dispersed in a polymer or an adhesive.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryopretectants, lyoprotectants, thickening agents, and inert gases.

In some embodiments, the pharmaceutical compositions are administered topically by electroporation, iontophoresis, phonophoresis, sonophoresis and microneedle or needle-free injection, such as POWDERJECT™ (Chiron Corp., Emeryville, Calif.), and BIOJECT™ (Bioject Medical Technologies Inc., Tualatin, Oreg.).

In some embodiments, the pharmaceutical compositions provided herein are provided in the forms of ointments, creams, and gels. Suitable ointment vehicles include oleaginous or hydrocarbon vehicles, including such as lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

In some embodiments, suitable cream base are oil-in-water or water-in-oil. In some embodiments, cream vehicles are water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation includes a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In some embodiments, in order to prepare a uniform gel, dispersing agents such as alcohol or glycerin are added, or the gelling agent dispersed by trituration, mechanical mixing, and/or stirring.

In some embodiments, the pharmaceutical compositions provided herein are administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas.

In some embodiments, these dosage forms are manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles in some embodiments, are used. Rectal and vaginal suppositories in some embodiments, are prepared by the compressed method or molding. The typical weight of a rectal and vaginal suppository is about 2 to about 3 g.

In some embodiments, the pharmaceutical compositions provided herein are administered ophthalmically in the forms of solutions, suspensions, ointments, emulsions, gel-forming solutions, powders for solutions, gels, ocular inserts, and implants.

In some embodiments, the pharmaceutical compositions provided herein are administered intranasally or by inhalation to the respiratory tract. The pharmaceutical compositions in some embodiments, are provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions in some embodiments, are provided as a dry powder for insufflation, alone or in combination with an inert carrier such as lactose or phospholipids; and nasal drops. For intranasal use, the powder in some embodiments, comprises a bioadhesive agent, including chitosan or cyclodextrin.

In some embodiments, solutions or suspensions for use in a pressurized container, pump, spray, atomizer, or nebulizer are formulated to contain ethanol, aqueous ethanol, or a suitable alternative agent for dispersing, solubilizing, or extending release of the active ingredient provided herein, a propellant as solvent; and/or an surfactant, such as sorbitan trioleate, oleic acid, or an oligolactic acid.

In some embodiments, the pharmaceutical compositions provided herein are micronized to a size suitable for delivery by inhalation, such as about 50 micrometers or less, or about 10 micrometers or less. Particles of such sizes in some embodiments, are prepared using a comminuting method, such as spiral jet milling, fluid bed jet milling, supercritical fluid processing to form nanoparticles, high pressure homogenization, or spray drying.

In some embodiments, capsules, blisters and cartridges for use in an inhaler or insufflator are formulated to contain a powder mix of the pharmaceutical compositions provided herein; a suitable powder base, such as lactose or starch; and a performance modifier, such as l-leucine, mannitol, or magnesium stearate. The lactose includes an anhydrous form or the form of the monohydrate. Other suitable excipients or carriers include dextran, glucose, maltose, sorbitol, xylitol, fructose, sucrose, and trehalose. In some embodiments, the pharmaceutical compositions provided herein for inhaled/intranasal administration further comprise a suitable flavor, such as menthol and levomenthol, or sweeteners, such as saccharin or saccharin sodium.

In some embodiments, the pharmaceutical compositions provided herein for topical administration are formulated to be immediate release or modified release, including delayed-, sustained-, pulsed-, controlled-, targeted, and programmed release.

Modified Release

The pharmaceutical compositions provided herein in some embodiments, are formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms are prepared using a variety of modified release devices and methods, including, but not limited to, matrix controlled release devices, osmotic controlled release devices, multiparticulate controlled release devices, ion-exchange resins, enteric coatings, multilayered coatings, microspheres, liposomes, and combinations thereof. In some embodiments, the release rate of the active ingredient(s) are modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form in some embodiments, are fabricated using a matrix controlled release device (see, e.g., Takada et al in "Encyclopedia of Controlled Drug Delivery," Vol. 2, Mathiowitz ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate, and fatty compounds, such as carnauba wax, microcrystalline wax, and triglycerides.

In a matrix controlled release system, the desired release kinetics is controllable, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form in some embodiments, are prepared by methods, including direct compression, dry or wet granulation followed by compression, melt-granulation followed by compression.

2. Osmotic Controlled Release Devices

The pharmaceutical compositions provided herein in a modified release dosage form in some embodiments, are fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly (acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents are osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol, organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates in some embodiments, are employed to influence how rapidly the active ingredient(s) is initially delivered from the dosage form. For example, amorphous sugars, such as Mannogeme EZ (SPI Pharma, Lewes, Del.) are used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core in some embodiments, also includes a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane in some embodiments, is a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane in some embodiments, is formed post-coating by mechanical or laser drilling. Delivery port(s) in some embodiments, is formed in situ by erosion of a plug of water-soluble material or by rupture of a thinner portion of the membrane over an indentation in the core. In addition, delivery ports are formed during coating process, as in the case of asymmetric membrane coatings of the type disclosed in U.S. Pat. Nos. 5,612, 059 and 5,698,220.

The total amount of the active ingredient(s) released and the release rate are substantially modulated, in some embodiments, via the thickness and porosity of the semipermeable membrane, the composition of the core, and the number, size, and position of the delivery ports.

The pharmaceutical compositions in an osmotic controlled-release dosage form in some embodiments, further comprise additional conventional excipients or carriers as described herein to promote performance or processing of the formulation.

In some embodiments, the osmotic controlled-release dosage forms are prepared according to conventional methods and techniques (see, e.g., *Remington: The Science and Practice of Pharmacy*; Santus and Baker, J. Controlled Release 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. In some embodiments, the AMT controlled-release dosage forms are prepared using methods such as direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form in some embodiments, are fabricated a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates in some embodiments, are made by the processes such as wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

For administration by inhalation, the compounds of Formula (I) or (II) are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit in some embodiments, is determined by providing a valve to deliver a metered amount. Capsules and cartridges of, e.g., gelatin for use in an inhaler or insufflator are formulated containing a powder mix of the compound and a suitable powder base such as lactose or starch.

Methods of Treatment, Dosages and Combination Therapies

The term "mammal" means all mammals including humans. Mammals include, by way of example only, humans, non-human primates, cows, dogs, cats, goats, sheep, pigs, lagomorphs, rats, mice and rabbits.

The term "effective amount" as used herein refers to that amount of the compound being administered which will relieve to some extent one or more of the symptoms of the disease, condition or disorder being treated.

The term "indirectly modulates" as used herein refers to an agent that reduces serum retinol levels in a mammal, resulting in a reduction of retinol levels in the eye of the mammal. Such a reduction in ocular retinol levels leads to a modulation of the activity of visual cycle proteins. This form of modulation (arises via a decrease in ocular serum retinol levels) is referred to herein as indirect modulation.

In some embodiments, the compositions containing the compound(s) described herein are administered for prophylactic and/or therapeutic treatments. The term "treating" is used to refer to either prophylactic and/or therapeutic treatments. In therapeutic applications, the compositions are administered to a patient already suffering from a disease, condition or disorder, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds is administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds is given continuously or temporarily suspended for a certain length of time (i.e., a "drug holiday").

Once improvement of the patient's conditions has occurred, a maintenance dose is administered if necessary. Subsequently, in some embodiments, the dosage or the frequency of administration, or both, are reduced, as a function of the symptoms, to a level at which the improved disease, disorder or condition is retained. In some embodiments, patients require intermittent treatment on a long-term basis upon any recurrence of symptoms.

The amount of a given agent that will correspond to such an amount will vary depending upon factors such as the particular compound, disease condition and its severity, the identity (e.g., weight) of the subject or host in need of treatment, but is determined according to the particular circumstances surrounding the case, including, e.g., the specific agent being administered, the route of administration, the condition being treated, and the subject or host being treated. In general, however, doses employed for adult human treatment will typically be in the range of about 0.02 to about 5000 mg per day. In other embodiments, the doses employed for adult human treatment is in the range of about 1 to about 1500 mg per day. The desired dose is conveniently presented in some embodiments, in a single dose or as divided doses administered simultaneously (or over a short period of time) or at appropriate intervals, for example as two, three, four or more sub-doses per day.

In certain instances, it is appropriate to administer at least one of the compounds described herein (or a pharmaceutically acceptable salt, ester, amide, prodrug, or solvate) in combination with another therapeutic agent. By way of example only, if one of the side effects experienced by a patient upon receiving one of the compounds herein is inflammation, then it is appropriate to administer an anti-inflammatory agent in combination with the initial therapeutic agent. Or, by way of example only, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, by way of example only, the benefit of experienced by a patient is increased by administering one of the compounds described herein with another therapeutic agent (which also includes a therapeutic regimen) that also has therapeutic benefit. By way of example only, in a treatment for macular degeneration involving administration of one of the compounds described herein, increased therapeutic benefit results by also providing the patient with other therapeutic agents or therapies for macular degeneration. In any case, regardless of the disease, disorder or condition being treated, the overall benefit experienced by the patient is simply additive of the two therapeutic agents or the patient experiences a synergistic benefit.

Also presented herein are combination therapies which include the use of a compound of Formula (I) or (II) with modulators of serum retinol levels or activity. In one embodiment the combination comprises a compound of Formula (I) or (II) and a compound of Formula (III):

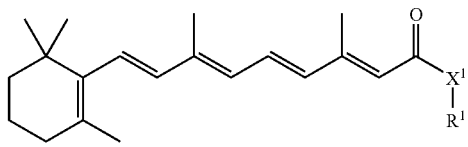

Formula (III)

wherein $X^1$ is selected from the group consisting of $NR^2$, O, S, $CHR^2$; $R^1$ is $(CHR^2)_x$-$L^1$-$R^3$, wherein x is 0, 1, 2, or 3; $L^1$ is a single bond or —C(O)—; $R^2$ is a moiety selected from the group consisting of H, $(C_1$-$C_4)$alkyl, F, $(C_1$-$C_4)$fluoroalkyl, $(C_1$-$C_4)$alkoxy, —C(O)OH, —C(O)—$NH_2$, —$(C_1$-$C_4)$alkylamine, —C(O)—$(C_1$-$C_4)$alkyl, —C(O)—$(C_1$-$C_4)$fluoroalkyl, —C(O)—$(C_1$-$C_4)$alkylamine, and —C(O)—$(C_1$-$C_4)$alkoxy; and $R^3$ is H or a moiety, optionally substituted with 1-3 independently selected substituents, selected from the group consisting of $(C_2$-$C_7)$alkenyl, $(C_2$-$C_7)$alkynyl, aryl, $(C_3$-$C_7)$cycloalkyl, $(C_5$-$C_7)$cycloalkenyl, and a heterocycle; or an active metabolite, or a pharmaceutically acceptable prodrug or solvate thereof. In another embodiment, the combination comprises a compound of Formula (I) or (II) and a compound of Formula (III) wherein the combination modulates serum retinol levels or activity. In a further embodiment is a combination comprising a compound of Formula (I) or (II) and a compound of Formula (III) wherein $X^1$ is $NR^2$ and R is H or $(C_1$-$C_4)$alkyl. In yet a further embodiment is a combination comprising a compound of Formula (I) or (II) and a compound of Formula (III) wherein x is 0. In another embodiment is a combination comprising a compound of Formula (I) or (II) and a compound of Formula (III) wherein x is 1 and $L^1$ is —C(O)—. In yet another embodiment is a combination comprising a compound of Formula (I) or (II) and a compound of Formula (III) wherein $R^3$ is an optionally substituted heteroaryl. In a further embodiment is a combination comprising a compound of Formula (I) or (II) and a compound of Formula (III) wherein the compound of Formula (III) is

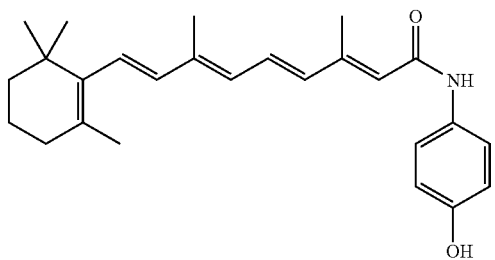

or an active metabolite, or a pharmaceutically acceptable prodrug or solvate thereof. In one embodiment is a combination comprising a compound of Formula (I) or (II) and a compound of Formula (III) wherein the compound of Formula (III) is 4-hydroxyphenylretinamide.

Specific, non-limiting examples of combination therapies include use of at least one compound of Formula (I) or (II) with nitric oxide (NO) inducers, statins, negatively charged phospholipids, anti-oxidants, minerals, anti-inflammatory agents, anti-angiogenic agents, matrix metalloproteinase inhibitors, and carotenoids. In several instances, suitable combination agents fall within multiple categories (by way of example only, lutein is an anti-oxidant and a carotenoid). Further, the compounds of Formula (I) or (II) in some embodiments, are administered with additional agents that may provide benefit to the patient, including by way of example only cyclosporin A.

In addition, the compounds of Formula (I) and (II) in some embodiments, are used in combination with procedures that provides additional or synergistic benefit to the patient, including, by way of example only, the use of extracorporeal rheopheresis (also known as membrane differential filtration), the use of implantable miniature telescopes, laser photocoagulation of drusen, and microstimulation therapy.

The use of anti-oxidants has been shown to benefit patients with macular degenerations and dystrophies. See, e.g., *Arch. Opthalmol*, 119: 1417-36 (2001); Sparrow, et al., *J. Biol. Chem.*, 278:18207-13 (2003). Examples of suitable anti-oxidants that could be used in combination with at least one compound having the structure of Formula (I) or (II) include vitamin C, vitamin E, beta-carotene and other carotenoids, coenzyme Q, 4-hydroxy-2,2,6,6-tetramethylpiperidine-N-oxyl (also known as Tempol), lutein, butylated hydroxytoluene, resveratrol, a trolox analogue (PNU-83836-E), and bilberry extract.

The use of certain minerals has also been shown to benefit patients with macular degenerations and dystrophies. See, e.g., *Arch. Opthalmol*, 119: 1417-36 (2001). Examples of suitable minerals that could be used in combination with at least one compound having the structure of Formula (I) or (II) include copper-containing minerals, such as cupric oxide (by way of example only); zinc-containing minerals, such as zinc oxide (by way of example only); and selenium-containing compounds.

The use of certain negatively-charged phospholipids has also been shown to benefit patients with macular degenerations and dystrophies. See, e.g., Shaban & Richter, *Biol. Chem.*, 383:537-45 (2002); Shaban, et al., *Exp. Eye Res.*, 75:99-108 (2002). Examples of suitable negatively charged phospholipids that could be used in combination with at least one compound having the structure of Formula (I) or (II) include cardiolipin and phosphatidylglycerol. Positively-charged and/or neutral phospholipids in some embodiments, also provide benefit for patients with macular degenerations and dystrophies when used in combination with compounds having the structure of Formula (I) or (II).

The use of certain carotenoids has been correlated with the maintenance of photoprotection necessary in photoreceptor cells. Carotenoids are naturally-occurring yellow to red pigments of the terpenoid group that can be found in plants, algae, bacteria, and certain animals, such as birds and shellfish. Carotenoids are a large class of molecules in which more than 600 naturally occurring carotenoids have been identified. Carotenoids include hydrocarbons (carotenes) and their oxygenated, alcoholic derivatives (xanthophylls). They include actinioerythrol, astaxanthin, canthaxanthin, capsanthin, capsorubin, β-8'-apo-carotenal (apo-carotenal), β-12'-apo-carotenal, α-carotene, β-carotene, "carotene" (a mixture of α- and β-carotenes), γ-carotenes, β-cyrptoxanthin, lutein, lycopene, violerythrin, zeaxanthin, and esters of hydroxyl- or carboxyl-containing members thereof. Many of the carotenoids occur in nature as cis- and trans-isomeric forms, while synthetic compounds are frequently racemic mixtures.

In humans, the retina selectively accumulates mainly two carotenoids: zeaxanthin and lutein. These two carotenoids are thought to aid in protecting the retina because they are powerful antioxidants and absorb blue light. Studies with quails establish that groups raised on carotenoid-deficient diets had retinas with low concentrations of zeaxanthin and suffered severe light damage, as evidenced by a very high number of apoptotic photoreceptor cells, while the group with high zeaxanthin concentrations had minimal damage. Examples of suitable carotenoids for in combination with at least one compound having the structure of Formula (I) include lutein and zeaxanthin, as well as any of the aforementioned carotenoids.

Suitable nitric oxide inducers include compounds that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L- arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid) and the substrates for nitric oxide synthase, cytokines, adenosine, bradykinin, calreticulin, bisacodyl, and phenolphthalein. EDRF is a vascular relaxing factor secreted by the endothelium, and has been identified as nitric oxide or a closely related derivative thereof (Palmer et al, *Nature,* 327: 524-526 (1987); Ignarro et al, *Proc. Natl. Acad. Sci. USA,* 84:9265-9269 (1987)).

Statins serve as lipid-lowering agents and/or suitable nitric oxide inducers. In addition, a relationship has been demonstrated between statin use and delayed onset or development of macular degeneration. G. McGwin, et al, *British Journal of Opthalmology,* 87:1121-25 (2003). Statins can thus provide benefit to a patient suffering from an ophthalmic condition (such as the macular degenerations and dystrophies, and the retinal dystrophies) when administered in combination with compounds of Formula (I) or (II). Suitable statins include, by way of example only, rosuvastatin, pitivastatin, simvastatin, pravastatin, cerivastatin, mevastatin, velostatin, fluvastatin, compactin, lovastatin, dalvastatin, fluindostatin, atorvastatin, atorvastatin calcium (which is the hemicalcium salt of atorvastatin), and dihydrocompactin.

Suitable anti-inflammatory agents with which the Compounds of Formula (I) or (II) in some embodiments, are used include, by way of example only, aspirin and other salicylates, cromolyn, nedocromil, theophylline, zileuton, zafirlukast, montelukast, pranlukast, indomethacin, and lipoxygenase inhibitors; non-steroidal antiinflammatory drugs (NSAIDs) (such as ibuprofen and naproxin); prednisone, dexamethasone, cyclooxygenase inhibitors (i.e., COX-1 and/or COX-2 inhibitors such as Naproxen™, or Celebrex™); statins (by way of example only, rosuvastatin, pitivastatin, simvastatin, pravastatin, cerivastatin, mevastatin, velostatin, fluvastatin, compactin, lovastatin, dalvastatin, fluindostatin, atorvastatin, atorvastatin calcium (which is the hemicalcium salt of atorvastatin), and dihydrocompactin); and disassociated steroids.

Suitable matrix metalloproteinases (MMPs) inhibitors in some embodiments, are administered in combination with compounds of Formula (I) or (II) in order to treat ophthalmic conditions or symptoms associated with macular or retinal degenerations. MMPs hydrolyze most components of the extracellular matrix. These proteinases play a central role in many biological processes such as normal tissue remodeling, embryogenesis, wound healing and angiogenesis. However, excessive expression of MMP has been observed in many disease states, including macular degeneration. Many MMPs have been identified, most of which are multidomain zinc endopeptidases. A number of metalloproteinase inhibitors are known (see for example the review of MMP inhibitors by Whittaker M. et al, *Chemical Reviews* 99(9):2735-2776 (1999)). Representative examples of MMP Inhibitors include Tissue Inhibitors of Metalloproteinases (TIMPs) (e.g., TIMP-1, TIMP-2, TIMP-3, or TIMP-4), $\alpha_2$-macroglobulin, tetracyclines (e.g., tetracycline, minocycline, and doxycycline), hydroxamates (e.g., BATIMASTAT, MARIMISTAT and TROCADE), chelators (e.g., EDTA, cysteine, acetylcysteine, D-penicillamine, and gold salts), synthetic MMP fragments, succinyl mercaptopurines, phosphonamidates, and hydroxaminic acids. Examples of MMP inhibitors that are used in combination with compounds of Formula (I) or (II) include, by way of example only, any of the aforementioned inhibitors.

The use of antiangiogenic or anti-VEGF drugs has also been shown to provide benefit for patients with macular degenerations and dystrophies. Examples of suitable antiangiogenic or anti-VEGF drugs that could be used in combination with at least one compound having the structure of Formula (I) include Rhufab V2 (Lucentis™), Tryptophanyl-tRNA synthetase (TrpRS), Eye001 (Anti-VEGF Pegylated Aptamer), squalamine, Retaane™ 15 mg (anecortave acetate for depot suspension; Alcon, Inc.), Combretastatin A4 Prodrug (CA4P), Macugen™, Mifeprex™ (mifepristone-ru486), subtenon triamcinolone acetonide, intravitreal crystalline triamcinolone acetonide, Prinomastat (AG3340-synthetic matrix metalloproteinase inhibitor, Pfizer), fluocinolone acetonide (including fluocinolone intraocular implant, Bausch & Lomb/Control Delivery Systems), VEGFR inhibitors (Sugen), and VEGF-Trap (Regeneron/Aventis). Resveratrol, which can be extracted from walnuts or the skins of red grapes, has demonstrated anti-angiogenic activity and in some embodiments, is used as the second or additional agent for the combination therapies described herein. Furthermore, other trans-stilbene compounds are expected to exhibit similar activity.

In some embodiments, other pharmaceutical therapies that have been used to relieve visual impairment are used in combination with at least one compound of Formula (I) or (II). Such treatments include but are not limited to agents such as Visudyne™ with use of a non-thermal laser, PKC 412, Endovion euroSearch A/S), neurotrophic factors, including by way of example Glial Derived Neurotrophic Factor and Ciliary Neurotrophic Factor, diatazem, dorzolamide, Phototrop, 9-cis-retinal, eye medication (including Echo Therapy) including phospholine iodide or echothiophate or carbonic anhydrase inhibitors, AE-941 (AEterna Laboratories, Inc.), Sirna-027 (Sirna Therapeutics, Inc.), pegaptanib (NeXstar Pharmaceuticals/Gilead Sciences), neurotrophins (including, by way of example only, NT-4/5, Genentech), C and 5 (Acuity Pharmaceuticals), ranibizumab (Genentech), INS-37217 (Inspire Pharmaceuticals), integrin antagonists (including those from Jerini AG and Abbott Laboratories), EG-3306 (Ark Therapeutics Ltd.), BDM-E (BioDiem Ltd.), thalidomide (as used, for example, by EntreMed, Inc.), cardiotrophin-1 (Genentech), 2-methoxyestradiol (Allergan/Oculex), DL-8234 (Toray Industries), NTC-200 (Neurotech), tetrathiomolybdate (University of Michigan), LYN-002 (Lynkeus Biotech), microalgal compound (Aquasearch/Albany, Mera Pharmaceuticals), D-9120 (Celltech Group plc), ATX-S10 (Hamamatsu Photonics), TGF-beta 2 (Genzyme/Celtrix), tyrosine kinase inhibitors (Allergan, SUGEN, Pfizer), NX-278-L (eXstar Pharmaceuticals/Gilead Sciences), Opt-24 (OPTIS France SA), retinal cell ganglion neuroprotectants (Cogent Neurosciences), N-nitropyrazole derivatives (Texas A&M University System), KP-102 (Krenitsky Pharmaceuticals), and cyclosporin A. See U.S. Patent Application Publication No. 20040092435.

In any case, the multiple therapeutic agents (one of which is one of the compounds described herein) in some embodiments, are administered in any order or even simultaneously. If simultaneously, the multiple therapeutic agents in some embodiments, is provided in a single, unified form, or in multiple forms (by way of example only, either as a single pill or as two separate pills). One of the therapeutic agents in some embodiments, is given in multiple doses, or both may be given as multiple doses. If not simultaneous, the timing between the multiple doses varies from more than zero weeks to less than four weeks. In addition, the combination methods, compositions and formulations are not to be limited to the use of only two agents; we envision the use of multiple therapeutic combinations. By way of example only, a compound having the structure of Formula (I) or (II) is provided with at least one antioxidant and at least one negatively charged phospholipid; or a compound having the structure of Formula (I) or (II) is provided with at least one antioxidant and at least one inducer of nitric oxide production; or a compound having the structure of Formula (I) or (II) is provided with at least one inducer of nitric oxide productions and at least one negatively charged phospholipid; and so forth.

In addition, the compounds of Formula (I) or (II) in some embodiments, are used in combination with procedures that provide additional or synergistic benefit to the patient. Procedures to relieve visual impairment include but are not limited to 'limited retinal translocation', photodynamic therapy (including, by way of example only, receptor-targeted PDT, Bristol-Myers Squibb, Co.; porfimer sodium for injection with PDT; verteporfin, QLT Inc.; rostaporfin with PDT, Miravent Medical Technologies; talaporfin sodium with PDT, Nippon Petroleum; motexafin lutetium, Pharmacyclics, Inc.), antisense oligonucleotides (including, by way of example, products tested by Novagali Pharma SA and ISIS-13650, Isis Pharmaceuticals), laser photocoagulation, drusen lasering, macular hole surgery, macular translocation surgery, implantable miniature telescopes, Phi-Motion Angiography (also known as Micro-Laser Therapy and Feeder Vessel Treatment), Proton Beam Therapy, microstimulation therapy, Retinal Detachment and Vitreous Surgery, Scleral Buckle, Submacular Surgery, Transpupillary Thermotherapy, Photosystem I therapy, use of RNA interference (RNAi), extracorporeal rheopheresis (also known as membrane differential filtration and Rheotherapy), microchip implantation, stem cell therapy, gene replacement therapy, ribozyme gene therapy (including gene therapy for hypoxia response element, Oxford Biomedica; Lentipak, Genetix; PDEF gene therapy, GenVec), photoreceptor/retinal cells transplantation (including transplantable retinal epithelial cells, Diacrin, Inc.; retinal cell transplant, Cell Genesys, Inc.), and acupuncture.

Further combinations that are used to benefit an individual include using genetic testing to determine whether that individual is a carrier of a mutant gene that is correlated with certain ophthalmic conditions. By way of example only, defects in the human ABCA4 gene are thought to be associated with five distinct retinal phenotypes including Stargardt disease, cone-rod dystrophy, age-related macular degeneration and retinitis pigmentosa. See e.g., Allikmets et al., *Science*, 277:1805-07 (1997); Lewis et al., *Am. J. Hum. Genet.*, 64:422-34 (1999); Stone et al., *Nature Genetics*, 20:328-29 (1998); Allikmets, *Am. J. Hum. Gen.*, 67:793-799 (2000); Klevering, et al, *Opthalmology*, 111:546-553 (2004). In addition, an autosomal dominant form of Stargardt Disease is caused by mutations in the ELOV4 gene. See Karan, et al., *Proc. Natl. Acad. Sci*. (2005). Patients possessing any of these mutations are expected to find therapeutic and/or prophylactic benefit in the methods described herein.

In addition, in some embodiments, compounds of Formula (I) or (II) or other agents that result in the reduction of serum retinol levels are administered with (meaning before, during or after) agents that treat or alleviate side effects arising from serum retinol reduction. Such side effects include dry skin and dry eye. Accordingly, agents that alleviate or treat either dry skin or dry eye are administered in some embodiments, with compounds of Formula (I) or (II) or other agents that reduce serum retinol levels.

EXAMPLES

The following examples provide illustrative methods for the synthesis of compounds of Formula (I) or (II). These examples are provided for illustrative purposes only and not to limit the scope of the claims provided herein.

Analytical LC/MS Methods:
Method A:
Instrument: Waters HPLC/MS with UV detector (220 nM) and MS detector (ESI).
HPLC column: Waters Acquity BEH C18 1.7 μm 2.1 mm×50 mm.
HPLC Gradient: 0.6 mL/min, from 95:5 20 mM ammonium formate buffer (brought to pH 7.4 with ammonium hydroxide):acetonitrile to 20:80 ammonium formate buffer:acetonitrile in 1.5 min, maintaining for 1.3 min.
Method B:
Instrument: Waters LC/MS with DAD detector (220 and 254 nM) and MS detector (ESI).
HPLC column: Merck LiChroCART 30-4 Purospher STAR RP-18, endcapped, 3 μm 4.6 mm×50 mm.
HPLC Gradient: 1.5 mL/min, from 95:5 20 mM ammonium formate buffer (brought to pH 7.4 with ammonium hydroxide):acetonitrile to 5:95 ammonium formate buffer:acetonitrile in 2.5 min, maintaining for 1.8 min.
Method C:
Instrument: Waters Alliance with UV detector (220 nM) and MS detector (ESI).
HPLC column: Waters XTerra MS C18, 5 μm, 4.6 mm×50 mm.
HPLC Gradient: 2 mL/min, from 95:5 water+5% formic acid:acetonitrile+5% formic acid for 0.5 min. then to 5:95 aqueous:organic in 5 min, maintaining for 0.5 min.

Example 1

Synthesis of
5-(2-tert-Butyl-4-chlorophenoxy)pentanoic Acid

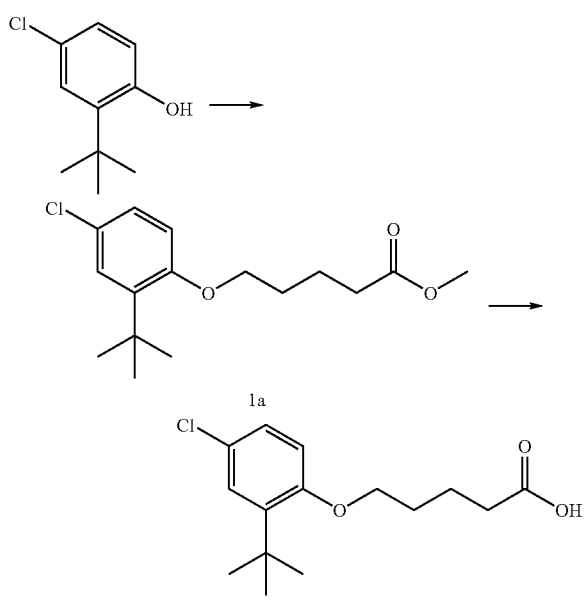

Methyl 5-bromovalerate (1.52 mL, 2.09 g, 10.7 mmol), 2-tert-butyl-4-chloro-phenol (2.4 g, 13 mmol) and potassium carbonate (1.4 g, 10.1 mmol) were suspended in dry DMF (10 mL) and stirred for 2 h at 120° C. To the resulting mixture water was added (80 mL) and extracted with ethyl acetate (3×20 mL). The organic layers were washed two times with 10% sodium hydroxide (2×20 mL), water (1×20 mL), dried over sodium sulfate and evaporated in vacuo. To afford 3.46 g (quant) crude 1a that was used in the next step without further purification. $^1$H NMR (400 MHz, CDCl$_3$) δ ppm 7.21 (d, J=2.6 Hz, 1H), 7.10 (dd, J=8.6, 2.6 Hz, 1H), 6.75 (d, J=8.6 Hz, 1H), 3.97 (t, J=5.8 Hz, 2H), 2.46 (t, J=6.9 Hz, 2H), 1.84-1.94 (m, 4H), 1.36 (s, 9H).

A mixture of 1a (3.46 g), 10% sodium hydroxide (10 mL) in dioxane (50 mL) was stirred overnight at room temperature. The dioxane was removed in vacuo, the remaining mixture was diluted with water and extracted with ethyl acetate (2×20 mL). The pH of the aqueous layer was adjusted to 4 with concentrated hydrochloric acid, and extracted with chloroform (1×20 mL). The combined organic layers were dried over sodium sulfate and evaporated in vacuo. The product was triturated with hexane to yield 1.87 g (61% calculated from methyl 5-bromovalerate) white crystalline 1-1. mp. 95.4-96.4° C., $^1$H NMR (400 MHz, CDCl$_3$) δ ppm 7.21 (d, J=2.6 Hz, 1H), 7.10 (dd, J=8.6, 2.6 Hz, 1H), 6.75 (d, J=8.6 Hz, 1H), 3.97 (t, J=5.8 Hz, 2H), 2.46 (t, J=6.9 Hz, 2H), 1.84-1.94 (m, 4H), 1.36 (s, 9H).

The following compounds were made by the above procedure using 2-tert-butyl-4-chlorophenol and the appropriate methanesulfonyl ester.

| No. | | NMR |
|---|---|---|
| 1-2 | [structure] | $^1$H NMR (400 MHz, CDCl$_3$) δ ppm 7.23 (d, J = 2.6 Hz, 1H), 7.12 (dd, J = 2.6, 8.7 Hz, 1H), 6.76 (d, 8.7 Hz, 1H), 3.81 (d, J = 5.9 Hz, 1H), 2.39-2.50 (m, 1H), 2.23 (m, 1H), 2.10 (m, 1H), 1.89-1.98 (m, 3H), 1.41-1.45 (m, 1H), 1.38 (s, 9H), 1.26-1.34 (m, 1H), 1.08-1.18 (m, 1H). |
| 1-3 | [structure] | $^1$H NMR (400 MHz, CDCl$_3$) δ ppm 7.23 (d, J = 2.6 Hz, 1H), 7.12 (dd, J = 2.6, 8.7 Hz, 1H), 6.76 (d, J = 8.7 Hz, 1H), 3.85-3.92 (m, 2H), 2.88-2.98 (m, 1H), 2.47-2.68 (m, 1H), 2.19-2.35 (m, 1H), 1.92-2.14 (m, 3H), 1.50-1.84 (m, 2H), 1.38 (s, 9H) |

The following compounds were made by the above procedure using 2-tert-butyl-4-chlorophenol, the appropriate bromoester and cesium carbonate as the base in the first step and lithium hydroxide in the second step.

| No. | | NMR |
|---|---|---|
| 1-4 | [structure] | $^1$H NMR (300 MHz, CDCl$_3$) δ ppm 7.21 (d, J = 3 Hz, 1H), 7.10 (dd, J = 3, 9 Hz, 1H), 6.75 (d, 9 Hz, 1H), 4.01 (t, J = 6 Hz, 2H), 2.63 (t, J = 6 Hz, 2H), 2.18 (quint, J = 6 Hz, 2H), 1.32 (s, 9H). |
| 1-5 | [structure] | $^1$H NMR (300 MHz, CDCl$_3$) δ ppm 7.21 (d, J = 3 Hz, 1H), 7.10 (dd, J = 3, 9 Hz, 1H), 6.75 (d, 9 Hz, 1H), 3.94 (t, J = 6 Hz, 2H), 2.37 (t, J = 6 Hz, 2H), 1.86 (quint, J = 6 Hz, 2H), 1.68 (quint, J = 6 Hz, 2H), 1.4-1.6 (m, 4H), 1.32 (s, 9H). |

Example 2

Synthesis of 5-(2-tert-Butyl-4-chlorophenoxy)-N-(4-hydroxyphenyl)pentanamide

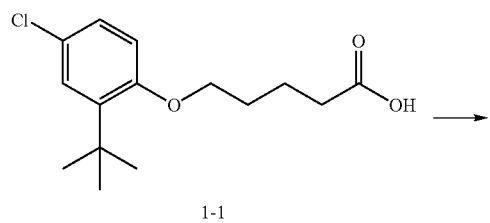

1-1

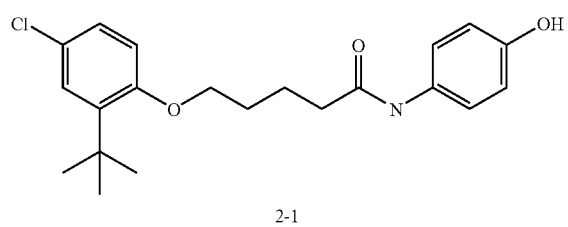

2-1

A mixture of 1-1 (0.3 g, 1.05 mmol) and carbonyl diimidazole (0.18 g, 1.11 mmol) was stirred in dichloroethane (2.5 mL) for 30 minutes, then 4-aminophenol (0.136 g, 1.25 mmol) and N,N-diisopropylethylamine (220 μL, 1.25 mmol) was added. The resulting solution was stirred for additional 4 h. The solvent was evaporated, the remaining mixture was diluted with 20 mL ether and washed with 1M hydrochloric acid (1×20 mL), the organic layer was dried over sodium sulfate and the solvent evaporated. The product was triturated with diisopropyl ether to give 2-1 (6 mg, 25%).

Example 3

Synthesis of Methyl 4-(5-(2-tert-butyl-4-chlorophenoxy)pentanamido)benzoate

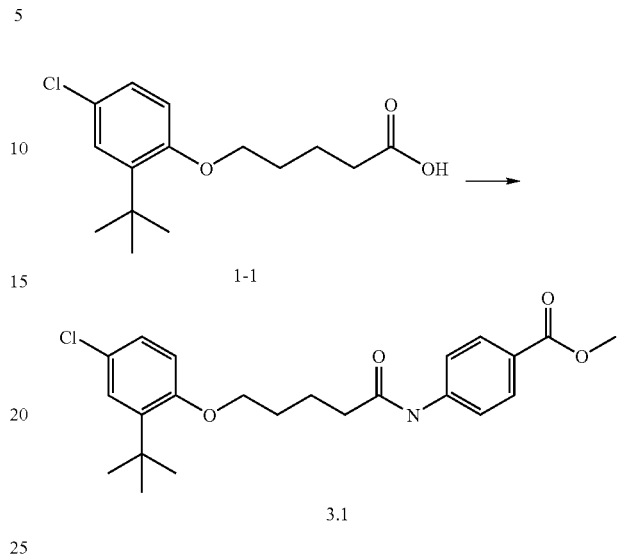

A mixture of 1-1 (0.25 g, 0.88 mmol) and oxalyl chloride (0.12 g, 0.95 mmol) in dichloroethane (5 mL) was stirred for 48 h at room temperature. The solvent was removed in vacuo and the residue was dissolved in dichloroethane. To this solution methyl 4-aminobenzoate (0.146 g, 0.96 mmol) and N,N-diisopropylethylamine (350 μL, 2.0 mmol) were added and stirred overnight at room temperature. The mixture was washed with 20 mL 10% hydrochloric acid, the organic layer was dried over sodium sulfate and the solvent was removed in vacuo to give 0.25 g (69%) 3-1. LCMS: method A, Rt: 1.85 min, M+H=418.

The following compounds were made by the above procedure using either oxalyl chloride or thionyl chloride.

| No. | | MW | MH+ | Rt | LCMS Method |
|---|---|---|---|---|---|
| 3-2 | ![structure] | 418 | 418 | 1.85 | A |
| 3-3 | ![structure] | 390 | 390 | 1.64 | A |
| 3-4 | ![structure] | 424 | 424 | 3.63 | B |

| No. | | MW | MH+ | Rt | LCMS Method |
|---|---|---|---|---|---|
| 3-5 | Cl-C6H3(tBu)-O-CH2-cyclopentyl-C(O)NH-C6H4-COOMe | 424 | 424 | 2.84 | B |
| 3-6 | Cl-C6H3(tBu)-O-CH2-cyclopentyl-C(O)NH-C6H4-CH2OH | 444 | 444 | 2.12 | A |
| 3-7 | Cl-C6H3(tBu)-O-CH2-cyclopentyl-C(O)NH-cyclohexyl-COOMe | 416 | 416 | 1.84 | A |
| 3-8 | Cl-C6H3(tBu)-O-CH2-cyclohexyl-C(O)NH-C6H4-OH | 450 | 450 | 1.98 | A |
| 3-9 | Cl-C6H3(tBu)-O-CH2-cyclohexyl-C(O)NH-C6H4-COOMe | 416 | 416 | 1.85 | A |
| 3-10 | Cl-C6H3(tBu)-O-CH2-cyclohexyl-C(O)NH-C6H4-CH2OH | 458 | 458 | 2.14 | A |

Example 4

Synthesis of Methyl 3-(3-((2-tert-butyl-4-chlorophenoxy)methyl)cyclopentane-carboxamido)cyclohexanecarboxylate

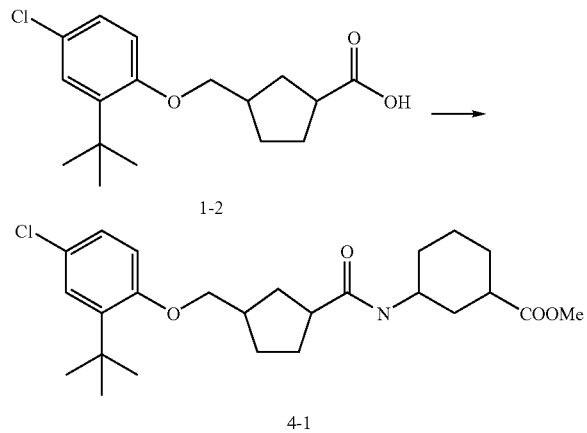

A solution of 1-2 (0.109 g, 0.354 mmol), N-hydroxybenzotriazole (0.053 g, 0.35 mmol) and EDC HCl (0.067 g, 0.35 mmol) in dry DMF was stirred for 40 minutes at room temperature, then methyl 3-aminocyclohexanecarboxylate hydrochloride (0.075 g, 0.385 mmol) and triethylamine (54 µL, 0.385 mmol) was added and stirring was continued for 4 h. The reaction mixture was diluted with 5% sodium bicarbonate (20 mL) and extracted with dichloromethane (3×20 mL). The combined organic layers were washed with 10% hydrochloric acid (1×20 mL), brine (2×20 mL) and dried over sodium sulfate. The solvent was removed in vacuo, the oily residue was purified by flash chromatography on Kieselgel 60H using chloroform as an eluent to yield 0.1 g (63%) 4-1 as a pale yellow oil. LCMS: method A, Rt: 1.98 min, M+H=450).

The following compounds were made by the above procedure using the appropriate amine.

Example 5

Synthesis of 4-(5-(2-tert-Butyl-4-chlorophenoxy)pentanamido)benzoic acid

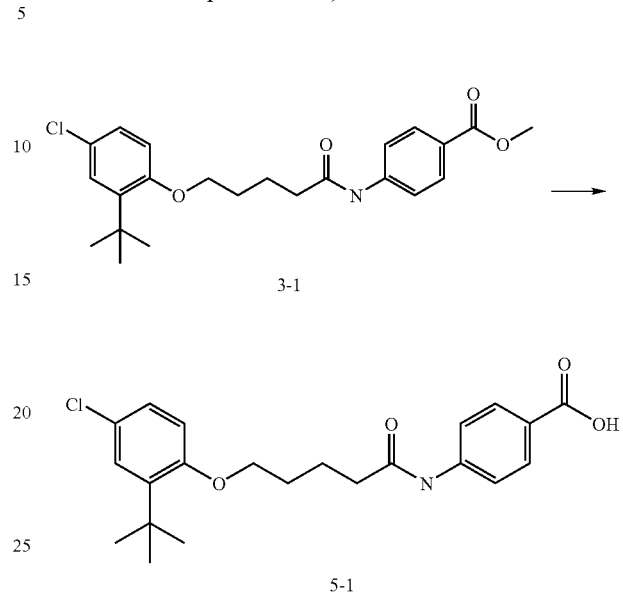

A mixture of 3-1 (0.25 g, 0.59 mmol) and sodium hydroxide (1M, 3 mL) in dioxane (4 mL) was stirred overnight at room temperature. The pH was adjusted to 4 with 1 M hydrochloric acid and the solution was extracted with 20 mL dichloromethane. The organic layer was dried over sodium sulfate, and the solvent was removed in vacuo to yield 5-1 (0.2 g, 83%). LCMS: method B, Rt: 2.08 min, M+H$_2$O=421.

| No. | | MW | MH+ | Rt | LCMS Method |
|---|---|---|---|---|---|
| 4-2 | | 402 | 402 | 5 | C |
| 4-3 | | 464 | 464 | 1.99 | A |
| 4-4 | | 464 | 464 | 2.02 | A |

The following compounds were made by the above procedure from the appropriate ester.
| No. | | MW | MH+ | Rt | LCMS Method |
|---|---|---|---|---|---|
| 5-2 | 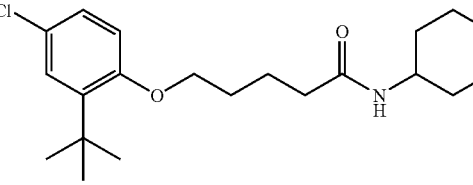 | 410 | 410 | 1.94 | B |
| 5-3 | 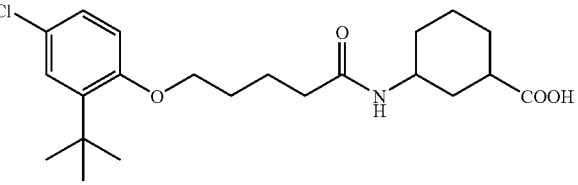 | 410 | 410 | 4.41 | A |
| 5-4 | 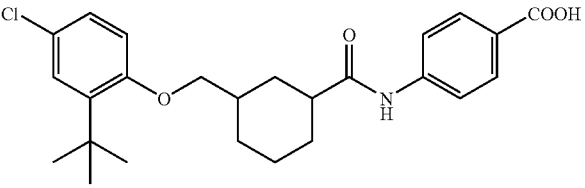 | 444 | 444 | 1.67 | A |
| 5-5 | 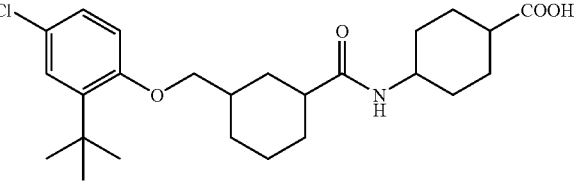 | 450 | 450 | 1.61 | A |
The following compounds were made by the above procedure from the appropriate ester, heating at 50° C. during the hydrolysis step.
| No. | | MW | MH+ | Rt | LCMS Method |
|---|---|---|---|---|---|
| 5-6 | 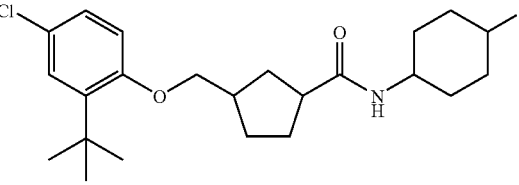 | 436 | 436 | 1.62 | A |
| 5-7 | 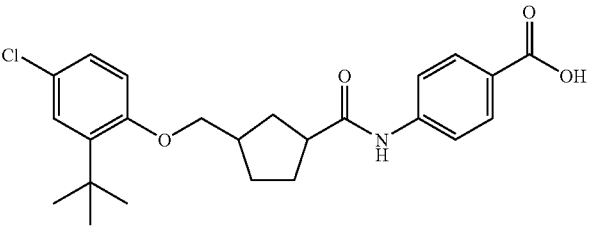 | 430 | 430 | 1.62 | A |

| No. | | MW | MH+ | Rt | LCMS Method |
|---|---|---|---|---|---|
| 5-8 | 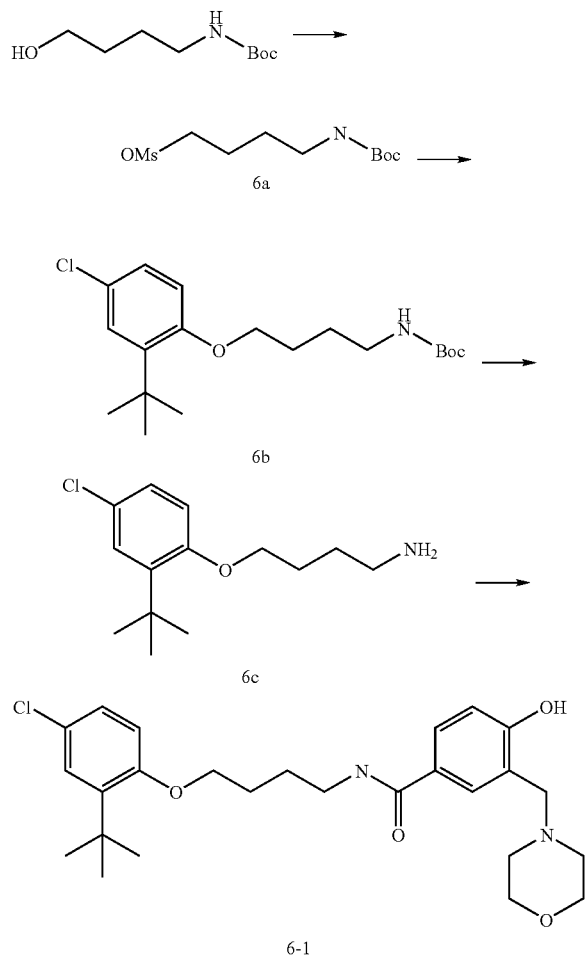 | 436 | 436 | 1.6 | A |
| 5-9 | | 450 | 450 | 1.63 | A |

Example 6

Synthesis of N-(4-(2-tert-Butyl-4-chlorophenoxy)butyl)-4-hydroxy-3-(morpholinomethyl)-benzamide To a solution of Boc-4-aminobutanol (5.07 g, 26.8 mmol) and triethylamine (7.5 mL, 53.6 mol) in dichloroethane (60 mL) was added methanesulfonyl chloride (2.3 mL, 29.5 mmol) at 0° C. After the addition was completed, the mixture was stirred for additional 10 minutes. The reaction mixture was washed with 30 mL cold saturated sodium bicarbonate and the organic layer was dried over magnesium sulfate. The solvent was evaporated to give 9.9 g crude 6a as yellow oil. This crude product was used in the next step.

To a mixture of 2-tert-butyl-4-chlorophenol (4.0 g, 21.7 mmol) and potassium carbonate (6.0 g, 43.4 mol) in dry DMF (40 mL) was added a solution of 24a (9.9 g, mmol) in dry DMF (40 mL) dropwise at 60° C. The resulting mixture was stirred overnight at 60° C. The mixture was poured into water, extracted with 20 mL ethyl acetate, the organic layer was dried over sodium sulfate, and the solvent was removed in vacuo. The crude product (8.3 g) was purified by column chromatography using a gradient elution with hexane/dichloromethane (1:1) then dichloromethane to give 2.41 g (31%) 6b.

A mixture of 6b (2.41 g, 6.8 mmol) and HCl in dioxane (15 mL, 6.5M) in ethyl acetate was stirred overnight. The mixture was evaporated and the residue was recrystallized from a mixture of diethyl ether and ethyl acetate to yield 1.41 g (81%) 6c.

A mixture of 4-(2-tert-butyl-4-chloro-phenoxy)-butylamine hydrochloride (0.102 g, 0.35 mmol), 4-hydroxy-3-morpholin-4-ylmethyl-benzoic acid (0.091 g, 0.385 mmol), triethylamine (54 µL, 0.385 mmol), N-hydroxybenzotriazole (0.059 g, 0.385 mmol), EDC HCl (0.074 g, 0.385 mmol) in dry DMF was stirred for 3 h at room temperature. 20 mL of a 5% sodium bicarbonate solution was added, and the reaction was extracted with dichloromethane (3×20 mL). The combined organic layers were washed with 10% hydrochloric acid (1×20 mL), brine (2×20 mL) and dried over sodium sulfate. The solvent was removed in vacuo, the residue was triturated with a mixture of diethyl ether and ethyl acetate. The crude product was purified by flash chromatography (Kieselgel 60H) using chloroform:methanol (10:3) as an eluent. Yield: 0.070 g (42%) 6-1. LCMS: method A, Rt: 1.80 min, M+H=475).

The following compounds were made by the above procedure, using the appropriate acid.

| No. | Structure | MW | MH+ | Rt | LCMS Method |
|---|---|---|---|---|---|
| 6-2 | | 489 | 489 | 1.88 | A |
| 6-3 | | 394 | 394 | 1.72 | A |
| 6-4 | | 408 | 408 | 1.84 | A |
| 6-5 | | 444 | 444 | 1.81 | A |
| 6-6 | | 458 | 458 | 1.88 | A |

Example 7

Synthesis of 4-(4-(2-tert-Butyl-4-chlorophenoxy)butylcarbamoyl)benzoic Acid

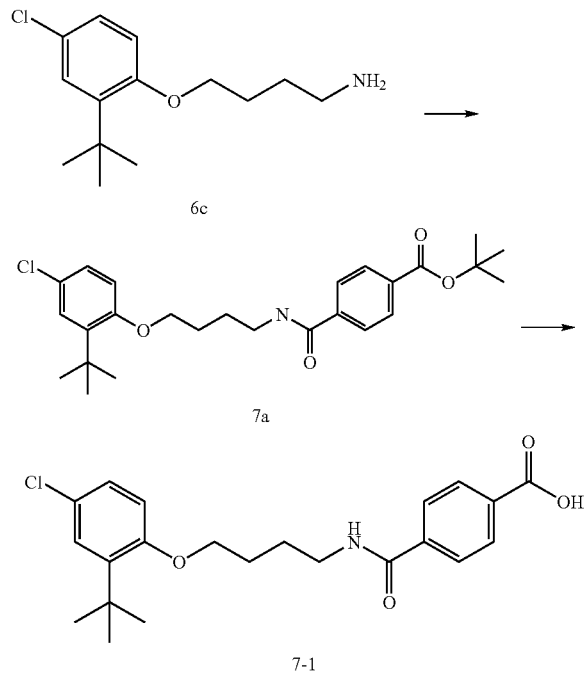

A mixture of 6c (0.117 g, 0.40 mmol), terephthalic acid mono-tert-butyl ester (0.098 g, 0.44 mmol), triethylamine (62 µL, 0.44 mmol), N-hydroxybenzotriazole (0.067 g, 0.44 mmol) and EDC HCl (0.084 g, 0.44 mmol) in dry DMF (5 mL) was stirred for 1 h at room temperature. 5% Sodium bicarbonate solution was added (20 mL), and the mixture was extracted with dichloromethane (3×20 mL). The combined organic layers were washed with 10% hydrochloric acid (1×20 mL), brine (2×20 mL) and dried over sodium sulfate. The solvent was removed in vacuo to give 0.246 g crude 7a.

The ester 7a was dissolved in 5 mL dioxane, 4 mL of 6.5 M hydrogen chloride in dioxane was added and the mixture was stirred at room temperature for 24 h. The reaction mixture was poured into water and extracted with dichloromethane (2×20 mL). The combined organic layers were washed with water (1×20 mL), dried over sodium sulfate, and the solvent was evaporated. The product 7-1 was crystallized from ether/hexane, filtered and washed several times with ether/hexane to give 0.127 (59%) white crystalline 25-1. LCMS: method A, Rt: 1.36 min, M+H=404.

The following compound was made by the above procedure.

| No. | | MW | MH+ | Rt | LCMS Method |
|---|---|---|---|---|---|
| 7-2 | ![structure] | 418 | 418 | 1.39 | A |

Example 8

The following compounds are made by the procedures described herein.

| No. | | MW |
|---|---|---|
| 8-1 | ![structure] | 310 |
| 8-2 | ![structure] | 294 |

| No. | | MW |
|---|---|---|
| 8-3 | 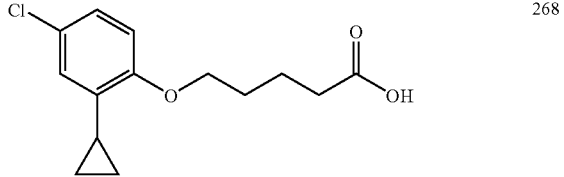 | 268 |
| 8-4 | 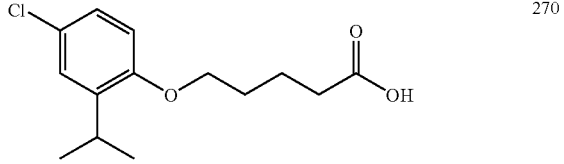 | 270 |
| 8-5 | 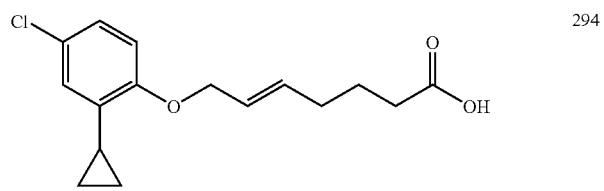 | 294 |
| 8-6 | 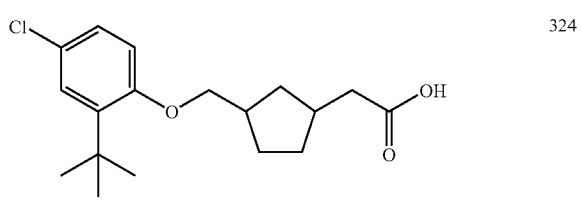 | 324 |
| 8-7 | 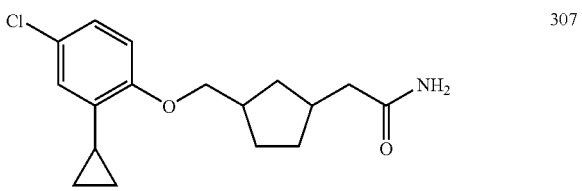 | 307 |
| 8-8 | 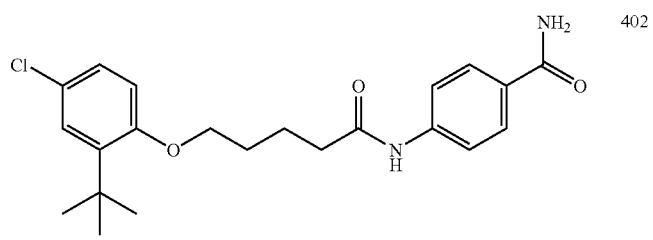 | 402 |
| 8-9 | 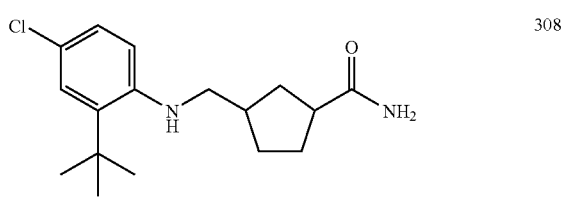 | 308 |

-continued
| No. | | MW |
|---|---|---|
| 8-10 | 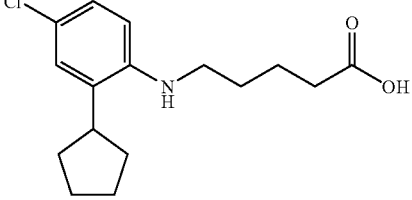 | 295 |
| 8-11 | 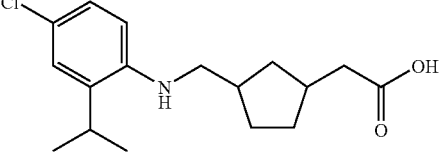 | 309 |
| 8-12 | 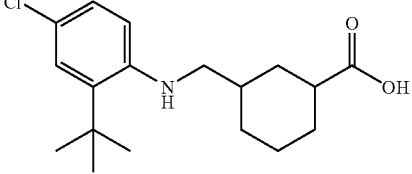 | 323 |
| 8-13 | 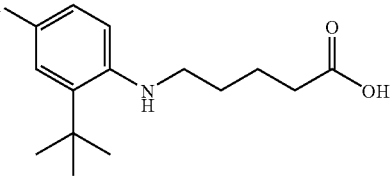 | 283 |
| 8-14 | 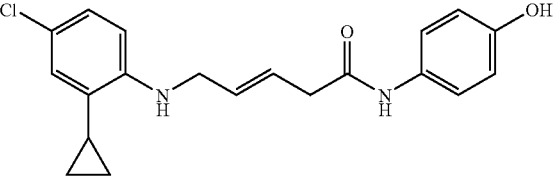 | 356 |
| 8-15 | 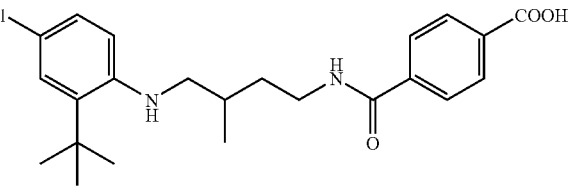 | 416 |
| 8-16 | 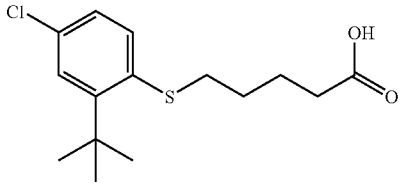 | 300 |
| 8-17 | 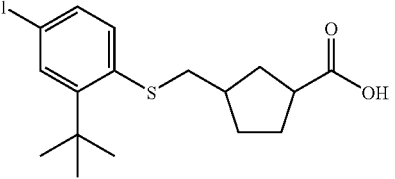 | 326 |

| No. | | MW |
|---|---|---|
| 8-18 | [4-Cl-2-isopropyl-phenyl-S-CH2-cyclopentyl-CH2-COOH] | 326 |
| 8-19 | [4-Cl-2-tert-butyl-phenyl-S-CH2-(tetrahydrofuran-2,5-diyl)-CH2-COOH] | 342 |
| 8-20 | [4-Cl-2-cyclopropyl-phenyl-S-CH2-CH=CH-CH2-CH2-COOH] | 310 |
| 8-21 | [4-Cl-2-isopropyl-phenyl-S-(CH2)4-C(O)-NH-C6H4-COOH] | 405 |
| 8-22 | [4-Cl-2-tert-butyl-phenyl-S-CH2-CH(CH3)-CH2-NH-C(O)-C6H4-COOH] | 433 |
| 8-23 | [4-Cl-2-tert-butyl-phenyl-O-CH2-cycloheptyl-COOH] | 338 |

The following examples provide illustrative methods for testing the effectiveness and safety of the compounds of Formula (I) or (II). These examples are provided for illustrative purposes only and not to limit the scope of the claims provided herein.

Mice and Rat Studies

The optimal dose of compounds of Formula (I) or (II) to block formation of A2E in abca4-1 mice is determined using a standard dose escalation study. In order to determine the range of doses which will be employed, a high throughput, in vitro assay which detects modulators that inhibit RBP-TTR interaction has been developed. Drug concentrations which cause a 50% inhibition of RBP-TTR interaction (the $IC_{50}$ values) are calculated from the data. In these experiments, fenretinide is employed as a positive control as it is known to be a potent inhibitor of RBP-TTR interaction. Representative data from a typical dose-response experiment is shown in FIG. 1. An illustrative in vivo approach, utilizing a compound having the structure of Formula (I) or (II) is presented below.

The effects of compounds of Formula (I) or (II) on all-trans-retinal in retinas from light-adapted mice is determined at doses that bracket the human therapeutic dose. The method includes treating mice with a single morning intraperitoneal dose. An increased frequency of injections in some embodiments, is required to maintain reduced levels of all-trans-retinal in the retina throughout the day.

ABCA4 Knockout Mice. ABCA4 encodes rim protein (RmP), an ATP-binding cassette (ABC) transporter in the outer-segment discs of rod and cone photoreceptors. The transported substrate for RmP is unknown. Mice generated with a knockout mutation in the abca4 gene, see Weng et al., *Cell*, 98:13-23 (1999), are useful for the study of RmP function as well as for an in vivo screening of the effectiveness for candidate substances. These animals manifest the complex ocular phenotype: (i) slow photoreceptor degeneration, (ii) delayed recovery of rod sensitivity following light exposure, (iii) elevated atRAL and reduced atROL in photoreceptor outer-segments following a photobleach, (iv) constitutively elevated phosphatidylethanolamine (PE) in outer-segments, and (v) accumulation of lipofuscin in RPE cells. See Weng et al., *Cell*, 98:13-23 (1999).

Rates of photoreceptor degeneration are monitored in treated and untreated wild-type and abca4−/− mice by two techniques. One is the study of mice at different times by ERG analysis and is adopted from a clinical diagnostic procedure. See Weng et al., *Cell*, 98:13-23 (1999). An electrode is placed on the corneal surface of an anesthetized mouse and the electrical response to a light flash is recorded from the retina. Amplitude of the α-wave, which results from light-induced hyperpolarization of photoreceptors, is a sensitive indicator of photoreceptor degeneration. See Kedzierski et al., *Invest. Opthalmol. Vis. Sci.*, 38:498-509 (1997). ERGs are done on live animals. In some embodiments, the same mouse is analyzed repeatedly during a time-course study. The definitive technique for quantitating photoreceptor degeneration is histological analysis of retinal sections. The number of photoreceptors remaining in the retina at each time point will be determined by counting the rows of photoreceptor nuclei in the outer nuclear layer.

Tissue Extraction. Eye samples are thawed on ice in 1 ml of PBS, pH 7.2 and homogenized by hand using a Duall glass-glass homogenizer. The sample is further homogenized following the addition of 1 ml chloroform/methanol (2:1, v/v). The sample is transferred to a borosilicate tube and lipids are extracted into 4 mls of chloroform. The organic extract is washed with 3 mls water and the samples are then centrifuged at 3,000×g, 10 min. The chloroform phase is decanted and the aqueous phase is re-extracted with another 4 mls of chloroform. Following centrifugation, the chloroform phases are combined and the samples were taken to dryness under nitrogen gas. Samples residues are resuspended in 200 1p 2-propanol and analyzed by HPLC as described below.

HPLC Analysis. Chromatographic separations are achieved on an Agilent Zorbax Rx-Sil Column (5 μm, 4.6× 250 mm) using an Agilent 1100 series liquid chromatograph equipped with fluorescence and diode array detectors. The mobile phase is delivered at a desired rate of a determined volume per min. Sample peak identification is made by comparison to retention time and absorbance spectra of authentic standards. Data is reported as peak fluorescence (L.U.) obtained from the fluorescence detector.

Administration of a compound of Formula (I) or (II) to an experimental group of mice and administration of DMSO alone to a control group of mice is performed and assayed for accumulation of A2E. The experimental group is given about 2.5 to about 20 mg/kg of a compound of Formula (I) or (II) per day in about 10 to about 25 μl of DMSO. Higher dosages are tested if no effect is seen with the highest dose of about 50 mg/kg. The control group is given 10 to 25 μl injections of DMSO alone. Mice are given either experimental or control substances by intraperitoneal (i.p.) injection administered during chronic dosing regimes.

To assay for the accumulation of A2E in abca4−/− mice RPE, 2.5 to 20 mg/kg of a compound of Formula (I) or (II) is provided by i.p. injection per day to 2-month old abca4−/− mice. After a predetermined period, both experimental and control mice are killed and the levels of A2E in the RPE are measured by HPLC.

Example 9

Effect of Test Compounds on Rod Cell Death or Rod Functional Impairment

Administration of a compound of Formula (I) or (II) to an experimental group of mice and administration of DMSO alone to a control group of mice is performed and assayed for the effects of the test compound on rod cell death or rod functional impairment. The experimental group is given about 2.5 to about 20 mg/kg of a compound of Formula (I) or (II) per day in about 10 to about 25 μl of DMSO. Higher dosages are tested if no effect is seen with the highest dose of about 50 mg/kg. The control group is given about 10 to about 25 μL injections of DMSO alone. Mice are administered either experimental or control substances by i.p. injection for various experimental time periods. Alternatively, mice are implanted with a pump which delivers either experimental or control substances at a rate of about 0.25 μl/hr for various experimental time periods.

Mice that are treated to about 2.5 to about 20 mg/kg of a compound of Formula (I) or (II) per day for approximately 8 weeks are assayed for the effects of a compound of Formula (I) or (II) on rod cell death or rod functional impairment by monitoring ERG recordings and performing retinal histology.

Example 10

Testing for Protection from Light Damage

The following study is adapted from Sieving, P. A., et al, *Proc. Natl. Acad. Sci.*, 98:1835-40 (2001). For chronic light-exposure studies, Sprague-Dawley male 7-wk-old albino rats are housed in 12:12 h light/dark cycle of 5 lux fluorescent white light. Injections of about 20 to about 50 mg/kg a compound of Formula (I) or (II) by i.p. injection in 0.18 ml DMSO are given three times daily to chronic rats for 8 wk. Controls receive 0.18 ml DMSO by i.p. injection. Rats are killed 2 d after final injections. Higher dosages are tested if no effect is seen with the highest dose of about 50 mg/kg.

For acute light-exposure studies, rats are dark-adapted overnight and given a single i.p. injection of the test compound about 20 to about 50 mg/kg in 0.18 ml DMSO under dim red light and kept in darkness for 1 h before being exposed to the bleaching light before ERG measurements. Rats exposed to 2,000 lux white fluorescent light for 48 h. ERGs are recorded 7 d later, and histology is performed immediately.

Rats are euthanized and eyes are removed. Column cell counts of outer nuclear layer thickness and rod outer segment (ROS) length are measured every 200 μm across both hemispheres, and the numbers are averaged to obtain a measure of cellular changes across the entire retina. ERGs are recorded from chronic rats at 4 and 8 wks of treatment. In acute rodents, rod recovery from bleaching light is tracked by dark-adapted ERGs by using stimuli that elicit no cone contribution. Cone recovery is tracked with photopic ERGs. Prior to ERGs, animals are prepared in dim red light and anaesthetized. Pupils are dilated and ERGs are recorded from both eyes simultaneously by using gold-wire corneal loops.

Example 11

Combination Therapy Involving Fenretinide

Mice and/or rats are tested in the manner described in Examples 8 and 9, but with an additional two arms. In one of the additional arms, groups of mice and/or rats are treated with increasing doses of Fenretinide, from about 5 mg/kg per day to about 50 mg/kg per day. In the second additional arm, groups of mice and/or rats are treated with a combination of about 20 mg/kg per day of the test compound and increasing doses of Fenretinide, from about 5 mg/kg per day to about 50 mg/kg per day. The benefits of the combination therapy are assayed as described in Examples 8 and 9.

Example 12

Efficacy of Test Compounds on the Accumulation of Lipofuscin (and/or A2E) in abca4 Null Mutant Mice: Phase I—Dose Response and Effect on Serum Retinol The effect of a compound of Formula (I) or (II) on reducing serum retinol in animals and human subjects led us to explore the possibility that reductions in lipofuscin and the toxic bis-retinoid conjugate, A2E, is realized. The rationale for this approach is based upon two independent lines of scientific evidence: 1) reduction in ocular vitamin A concentration via inhibition of a known visual cycle enzyme (11-cis retinol dehydrogenase) results in profound reductions in lipofuscin and A2E; 2) animals maintained on a vitamin A deficient diet demonstrate dramatic reductions in lipofuscin accumulation. Thus, the objective for this example is to examine the effect of a compound of Formula (I) or (II) in an animal model which demonstrates massive accumulation of lipofuscin and A2E in ocular tissue, the abca4 null mutant mouse.

Figure 3:
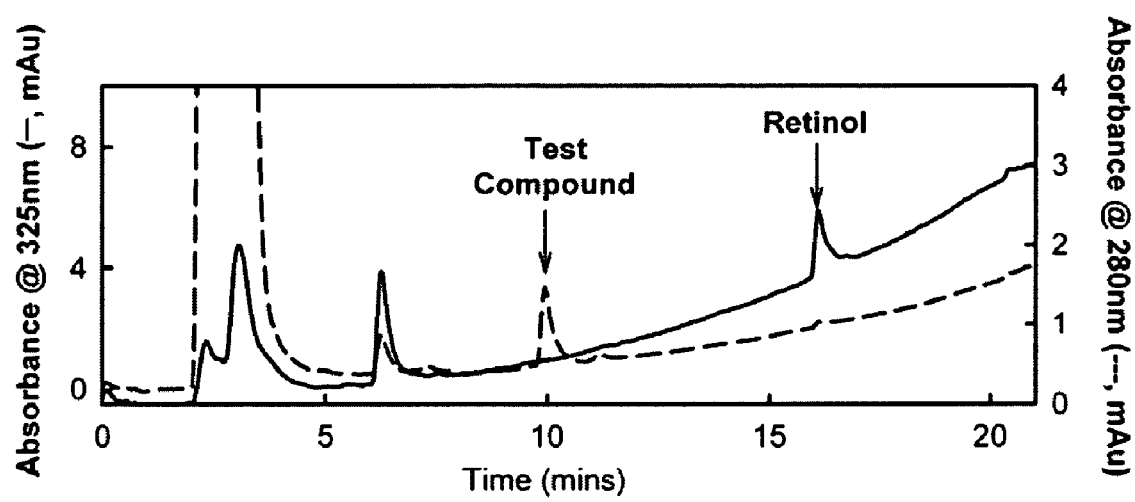
FIG. 3. Steady state serum concentrations of retinol and the test compound. Mice were administered daily doses of a test compound having the structure of Formula I (20 mg/kg/day, i.p. in DMSO). Following 28 days of treatment, blood samples were drawn and serum was prepared for analysis by HPLC. A representative chromatogram which shows the presence of the test compound (detected at 280 nm, dashed trace) and retinol (detected at 325 nm, solid trace) is provided.
Figure 4:
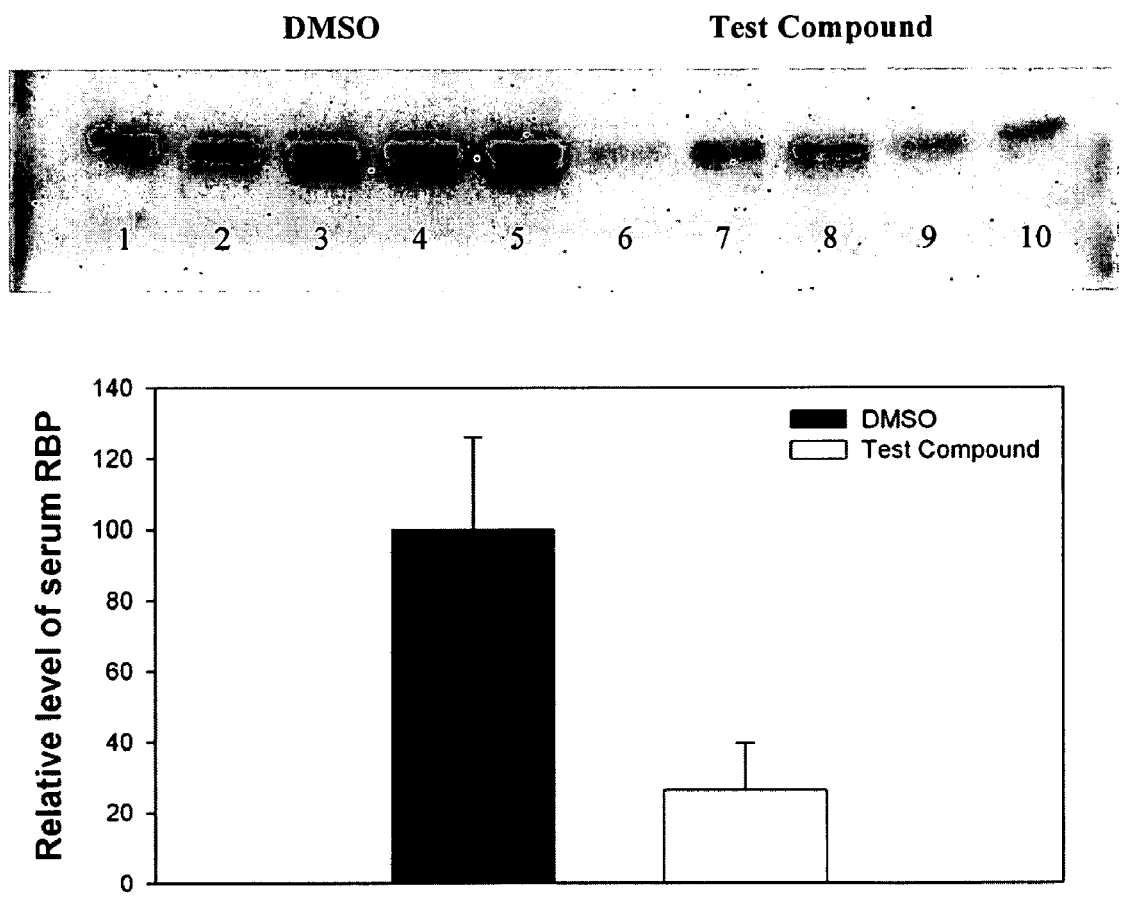
FIG. 4. Immunoblot detection and densitometric quantitation of RBP4. Western blot detection of RBP4 in serum of mice treated with either DMSO (upper panel, lanes 1-5) or a test compound having a structure consistent with Formula I (panel A, lanes 6-10). Pixel density of the bands shown lanes 1-5 of panel A were determined and the mean pixel density was taken as 100%. The relative level of RBP4 in mice treated with the test compound was also determined by pixel densitometry. These data are shown in the histogram.
Figure 9:
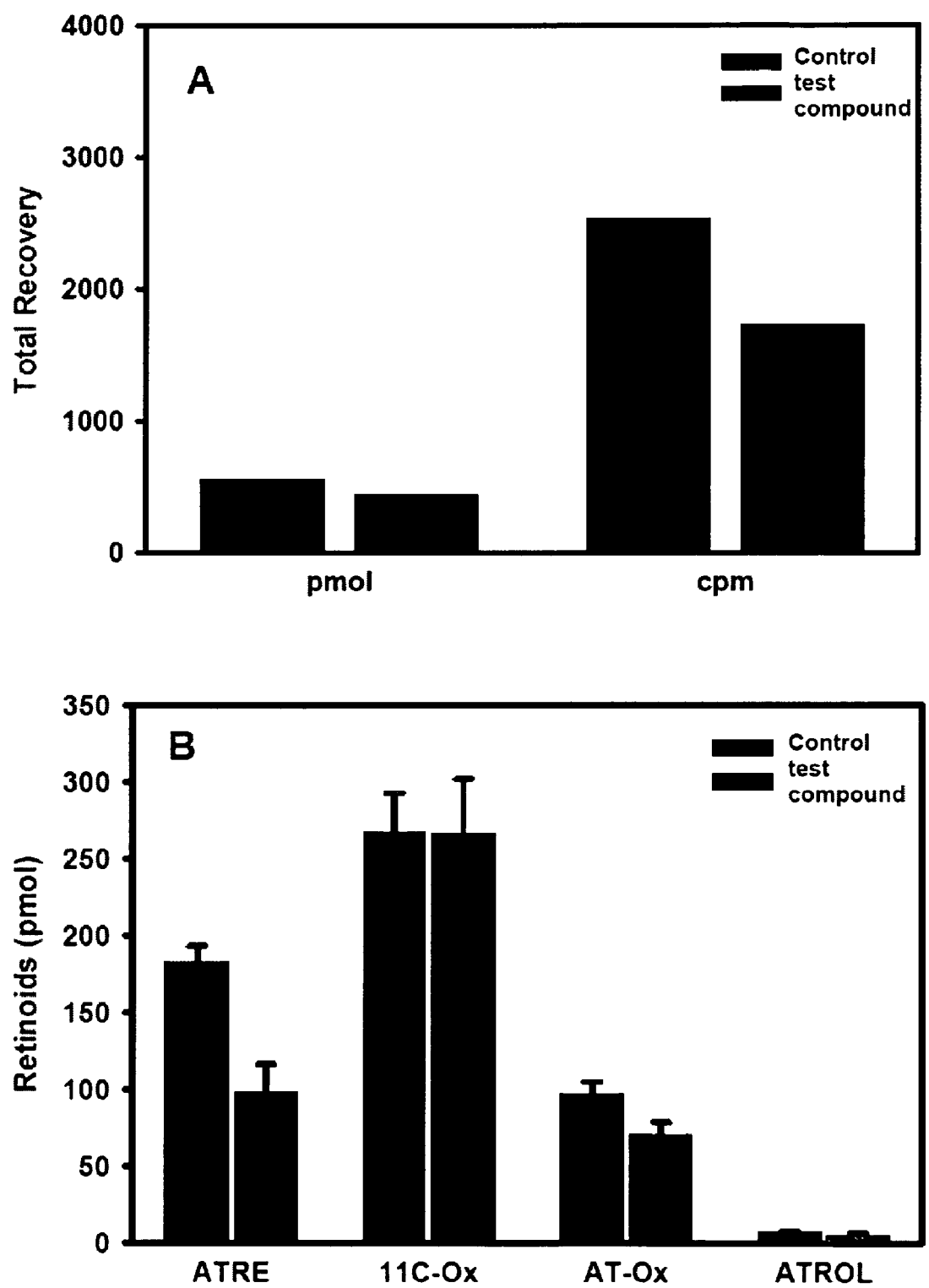
FIG. 9. Quantitation of ocular retinoids following treatment with test compound. ABCA4-1-mice were administered either ATRP (Control) or ATRP+SIR-1047 daily for 20 days (n=3 mice/group). On the final day of dosing, a trace amount of [$^3$H]ATROL (0.32 μmol, 8 μCi) in 100 μl corn oil was administered to all animals. Eyes were enucleated 5 hours later. One eye from each animal was used for retinoid analysis and the other eye was used for analysis of A2E and related fluorophores as described in the methods. The data show a marked reduction in uptake of [$^3$H]ATROL in the animals treated with test compound. Analysis of each retinoid species showed that the precursor substrate for visual chromophore biosynthesis (ATRE) and the immediate precursor for A2E biosynthesis (AT-Ox) are significantly reduced.

Initial studies begin by examining the effect of a compound of Formula (I) or (II) on serum retinol. Animals are divided into groups and given either DMSO, about 20 mg/kg of a compound of Formula (I) or (II) for at least 14 days. At the end of the study period, blood is collected from the animals, sera are prepared and an acetonitrile extract of the serum is analyzed by reverse phase LC/MS. UV-visible spectral and mass/charge analyses are performed to confirm the identity of the eluted peaks. Representative chromatographic data which show serum retinol levels in mice treated with either DMSO or a compound having the structure of Formula I are provided in FIG. 9. The steady state serum concentrations of the test compound (structure consistent with Formula I) are also determined by HPLC (see FIG. 3). Additionally, levels of RBP4 in serum are quantified by immunoblot (see FIG. 4).

Administration of an agent or agents that lower the levels of serum retinol in a patient without modulating at least one enzyme in the visual cycle is expected to provide a treatment for macular and/or retinal dystrophies and degenerations or the symptoms associated thereof. Assays, such as those described herein, are used in some embodiments, to select further agents possessing this action, including agents selected from compounds having the structure of Formula (I) or (II).

Example 13

Figure 5:
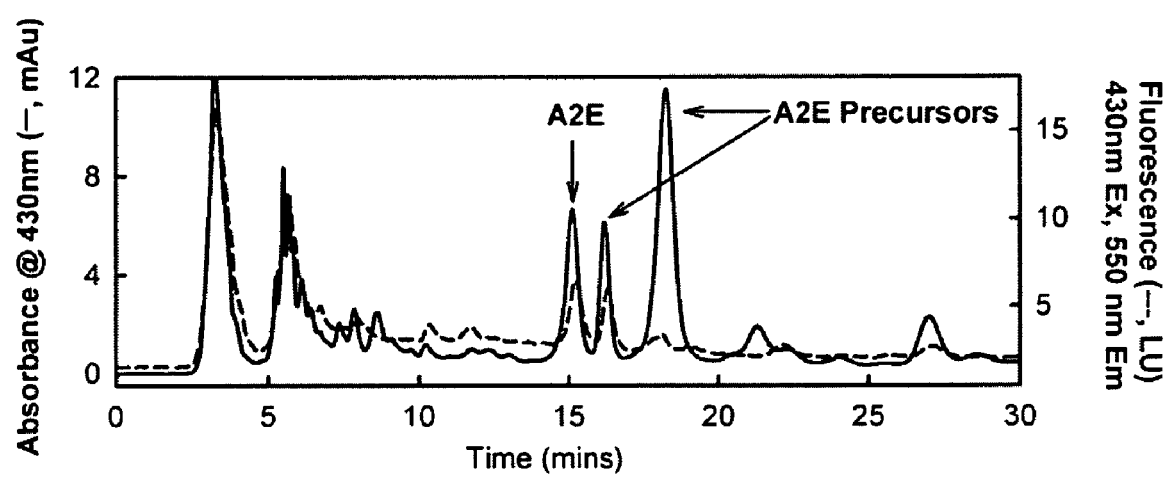
FIG. 5. Chromatographic separation and identification of toxic retinal fluorophores. Lipid soluble components were extracted from the eyecups of an abca4 null mutant mouse (BL6/129, aged 6 months). The eyecup extract was analyzed by HPLC with on-line absorbance (solid trace) and fluorescence (dashed trace) detection. The indicated fluorophores (A2E precursors and A2E) are not present in age-matched wild-type mice.

Efficacy of Test Compounds on the Accumulation of Lipofuscin (and/or A2E) in abca4 Null Mutant Mice: Phase II—Chronic Treatment of abca4 Null Mutant Mice Studies are performed to evaluate the effects of a compound of Formula (I) or (II) on reduction of A2E and A2E precursors in abca4 null mutant mice. A compound of Formula (I) or (II) is administered in DMSO (about 20 mg/kg, ip) to abca4 null mutant mice (BL6/129, aged 2 months) daily for a period of at least 28 days. Control age/strain matched mice receive only the DMSO vehicle. Mice are sampled at 0, 14, and 28 days (n=3 per group), the eyes are enucleated and chloroform-soluble constituents (lipids, retinoids and lipid-retinoid conjugates) are extracted. Mice are sacrificed by cervical dislocation, the eyes are enucleated and individually snap frozen in cryo vials. The sample extracts are then analyzed by HPLC with on-line fluorescence detection. A representative chromatographic tracing obtained from an eyecup extract of an abca4 null mutant mouse in shown in FIG. 5. A similar study is undertaken to ascertain effects of treatment with a compound of Formula (I) or (II) on the electroretinographic and morphological phenotypes.

Example 14

Combination Therapy Involving Test Compound and a Statin

Mice and/or rats are tested in the manner described in Examples 8 and 9, but with an additional two arms. In one of the additional arms, groups of mice and/or rats are treated with a suitable statin such as: Lipitor® (Atorvastatin), Mevacor® (Lovastatin), Pravachol® (Pravastatin sodium), Zocor™ (Simvastatin), Leschol (fluvastatin sodium) and the like with optimal dosage based on weight. In the second additional arm, groups of mice and/or rats are treated with a combination of about 20 mg/kg per day of a compound of Formula (I) or (II) and increasing doses of the statin used in the previous step. Suggested human dosages of such statins are for example: Lipitor® (Atorvastatin) about 10 to about 80 mg/day, Mevacor® (Lovastatin) about 10 to about 80 mg/day, Pravachol® (Pravastatin sodium) about 10 to about 40 mg/day, Zocor™ (Simvastatin) about 5 to about 80 mg/day, Leschol (fluvastatin sodium) about 20 to about 80 mg/day. Dosage of statins for mice and/or rat subjects should be calculated based on weight. The benefits of the combination therapy are assayed as described in Examples 8 and 9.

Example 15

Combination Therapy Involving Test Compound, Vitamins and Minerals

Mice and/or rats are tested in the manner described in Example 13, but with selected vitamins and minerals. Administration of a compound of Formula (I) or (II) in combination with vitamins and minerals is either orally or parenterally administered at amounts effective to inhibit the development or reoccurrence of macular degeneration. Test dosages are initially in the range of about 20 mg/kg per day of a compound of Formula (I) or (II) with about 100 to about 1000 mg vitamin C, about 100 to about 600 mg vitamin E, about 10,000 to about 40,000 IU vitamin A, about 50 to about 200 mg zinc and about 1 to about 5 mg copper for 15 to 20 weeks. The benefits of the combination therapy are assayed as described in Examples 8 and 9.

Example 16

Figure 2:
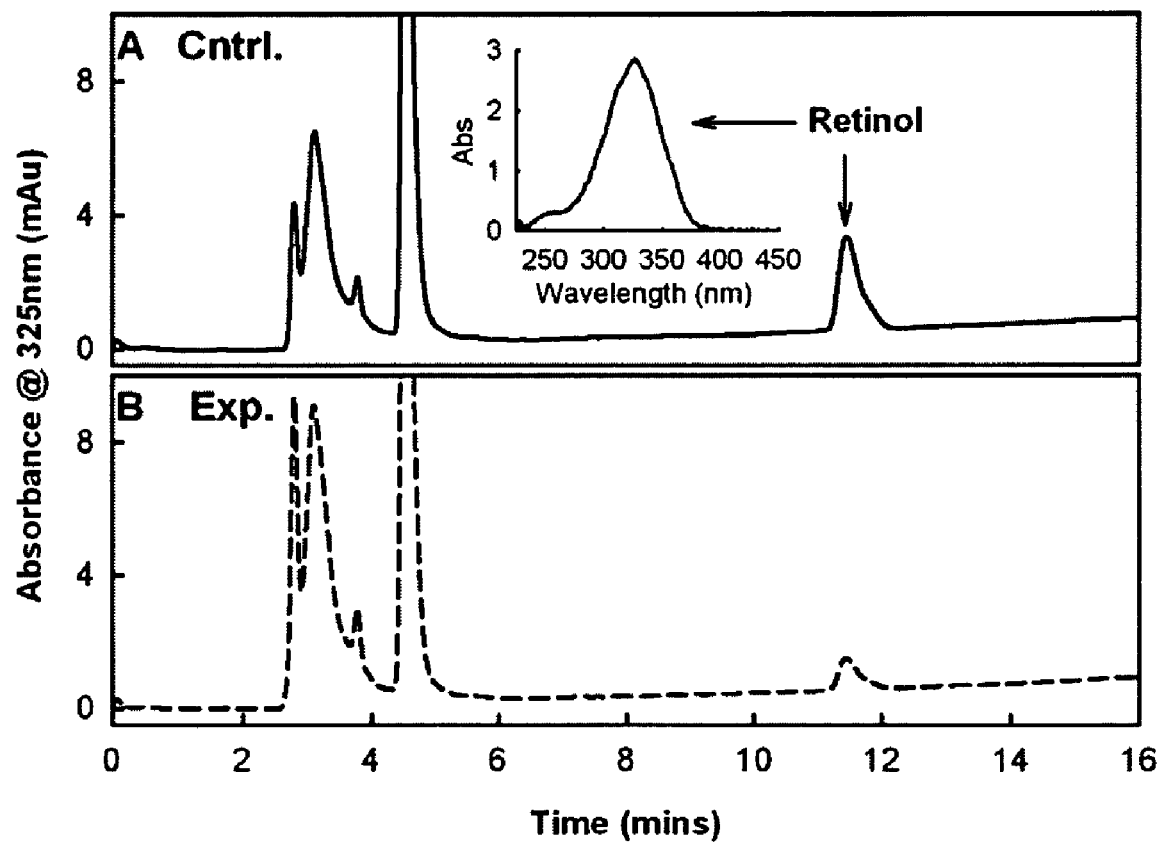
FIG. 2. HPLC analysis of serum retinol. Mice were treated with either DMSO or a compound having the structure of Formula I. Whole blood was collected from tails veins and serum was prepared. Serum samples were analyzed by HPLC. Representative chromatographic tracings are shown for a mouse receiving DMSO (panel A) and a mouse receiving the test compound (panel B). The retinol peak and its absorbance spectra are indicated in the plot.

Analysis of Serum Retinol as a Function of the Concentration of Test Compound ABCA4 null mutant mice are given the indicated dose of a compound of Formula (I) or (II) in DMSO (i.p.) daily for 28 days (n=4 mice per dosage group). At the end of the study period, blood samples are taken and serum is prepared. Following acetonitrile precipitation of serum proteins, the concentrations of retinol and of a compound of Formula (I) or (II) are determined from the soluble phase by LC/MS. Identification of the eluted compounds is confirmed by UV-vis absorption spectroscopy and co-elution of sample peaks with authentic standards (see FIG. 2).

Example 17

Identification of Compounds that Bind to TTR and/or Inhibit Gene Expression of TTR Purified TTR polypeptides comprising a glutathione-5-transferase protein and adsorbed onto glutathione-derivatized wells of 96-well microtiter plates are contacted with test compounds from a small molecule library at pH 7.0 in a physiological buffer solution. Purified TTR polypeptides have been described in the art. See U.S. Patent App. No. 20020160394, herein incorporated by reference. The test compounds in some embodiments, comprise a fluorescent tag. The samples are incubated for 5 minutes to one hour. Control samples are incubated in the absence of a test compound.

The buffer solution containing the test compounds is washed from the wells. Binding of a test compound to a TTR polypeptide is detected by fluorescence measurements of the contents of the wells. A test compound that increases the fluorescence in a well by at least 15% relative to fluorescence of a well in which a test compound is not incubated is identified as a compound which binds to a TTR polypeptide.

The identified test compound in some embodiments, are administered to a culture of human cells transfected with a TTR expression construct and incubated at 37° C. for 10 to 45 minutes. A culture of the same type of cells that have not been transfected is incubated for the same time without the test compound to provide a negative control.

RNA is then isolated from the two cultures as described in Chirgwin et al., Biochem. 18, 5294-99, 1979). Northern blots are prepared using 20 to 30 µg total RNA and hybridized with a $^{32}$P-labeled TTR-specific probe. Probes for detecting TTR mRNA transcripts have been described previously. A test compound that decreases the TTR-specific signal relative to the signal obtained in the absence of the test compound is identified as an inhibitor of TTR gene expression.

Example 18

Identification of Compounds that Bind to RBP and/or Inhibit Gene Expression of RBP Purified apo RBP are contacted with test compounds from a small molecule library at pH 7.0 in a physiological buffer solution. Purified apo RBP have been described in the art. See U.S. Patent App. No. 20030119715, herein incorporated by reference. The test compounds in some embodiments, comprise a fluorescent tag. The samples are incubated for 5 minutes to one hour. Control samples are incubated in the absence of a test compound. In some embodiments, competition assays in the presence of holo RBP (RBP complexed with retinol) are also performed.

The buffer solution containing the test compounds is washed from the wells. Binding of a test compound to apo RBP is detected by fluorescence measurements of the contents of the wells. A test compound that increases the fluorescence in a well by at least 15% relative to fluorescence of a well in which a test compound is not incubated is identified as a compound which binds to apo RBP.

The identified test compound are administered to a culture of human cells transfected with an RBP expression construct and incubated at 37° C. for 10 to 45 minutes. A culture of the same type of cells that have not been transfected is incubated for the same time without the test compound to provide a negative control.

RNA is then isolated from the two cultures as described in Chirgwin et al., Biochem. 18, 5294-99, 1979). Northern blots are prepared using about 20 to about 30 µg total RNA and hybridized with a $^{32}$P-labeled RBP-specific probe. A test compound that decreases the RBP-specific signal relative to the signal obtained in the absence of the test compound is identified as an inhibitor of RBP gene expression.

Example 19

Further Analysis of the Effect of Test Compound on Serum Retinol, Eyecup Retinoids, and A2E Levels Compound of Formula (I) or (II) Treatments. A compound of Formula (I) or (II) is administered daily (about 1.5 to about 15 µg/µl in 25 µl DMSO, i.p.) to ABCA4−/− mice for 28 days. Mice 1-2 months of age at study onset and are either pigmented (129/SV) or albino (BALB/c) strains. Mice are raised under 12-hr cyclic light/dark (30-50 lux) during the treatment period and are anesthetized by i.p. injection of ketamine (about 200 mg/kg) plus xylazine (about 10 mg/kg) before death by cervical dislocation.

Analysis of serum Retinol. Whole blood is collected from tail veins of test compound-treated mice 18 hrs. following the final test compound dose (i.e., at day 28). Serum is obtained from whole blood following centrifugation at 1,500×g, 10 min. Serum proteins are precipitated with the addition of an equivolume of ice-cold acetonitrile and centrifugation (10, 000×g, 10 min). An aliquot is removed from the soluble phase and analyzed by HPLC using an Agilent 1100 series capillary liquid chromatograph equipped with a diode-array detector. Chromatography is performed as described above.

Extraction and Analysis of Retinoids and A2E. Steady-state levels of retinoids and A2E in eyecups of ABCA4−/− mice are determined following daily administration (28 days) of a compound of Formula (I) or (II). Mice are sacrificed, the eyes enucleated, and the posterior portion of each eye is used for extraction of retinoids or A2E. Methodologies used for extraction of retinoids and A2E from eye tissue and HPLC analysis techniques have been described. See, e.g., Mata N L, Weng J, Travis G H. Biosynthesis of a major lipofuscin fluorophore in mice and humans with ABCR-mediated retinal and macular degeneration. *Proc Natl Acad Sci USA*. 2000; 97:7154-7159; Weng J, et al.; *Cell*. 1999; 98:13-23; Mata N L, et al.; *Invest. Opthalmol. Visual Sci*. 2001; 42:1685-1690. All samples are analyzed by HPLC using absorbance and fluorescence detection. In these analyses, a column thermostat is employed to maintain the solvent and column temperature at 40° C. Identity of the indicated compounds is confirmed by on-line spectral analysis and by co-elution with authentic standards.

Correlation between Serum Retinol, Ocular Retinoids, and A2E. Data collected demonstrates a direct correlation between reduction in serum retinol and a reduction in the level of retinoids and the level of A2E in the eyecups of mammals. Notably serum retinol reduction tracks, in a dose-dependent manner, both ocular retinoid levels and ocular A2E levels. For example, a compound of Formula (I) or (II) lower serum retinol levels in mammals, showing that a reduction of serum retinol effects the level of materials (e.g., A2E) associated with retinopathy and macular degenerations/dystrophies. Accordingly, agents, such as those described herein, that cause serum retinol reductions also are used, in some embodiments, to reduce A2E and retinoid levels in the eye, and further, be used to treat lipofuscin-based retinal diseases, e.g., retinopathies and macular degenerations/dystrophies, in the mammal.

Example 20

Validation of RBP as a Therapeutic Target for Arresting Accumulation of A2E

Figure 6:
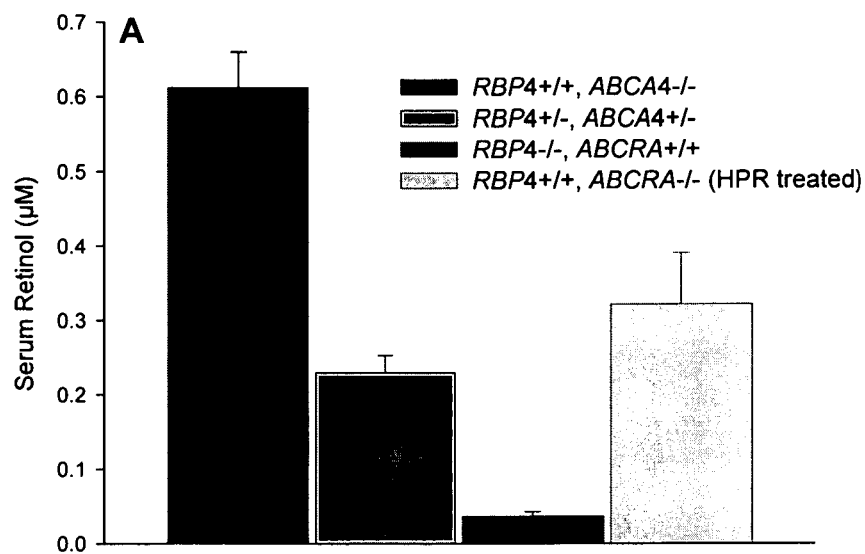
FIG. 6. Genetic modulation of RBP4 in abca4 mutant mice: effects on serum retinol, RBP4 and toxic retinal fluorophores. A line of mice which expresses heterozygous mutations in RBP4 and ABCA4 (RBP4+/−, ABCA4+/−) was generated in order to determine if genetic reduction of RBP4 would be sufficient to reduce serum levels of retinol, RBP4 and toxic retinal fluorophores within the RPE. Serum retinol concentrations in RBP4+/−, ABCA4+/− mice were reduced by greater than 50% compared to mice with the normal complement of RBP (RBP4+/+, ABCA4−/−). This degree of retinol reduction is comparable to that observed in HPR-treated RBP4+/+, ABCA4−/− mice (panel A). Reductions in serum retinol correlated directly with reductions in RBP4, as determined by immunoblot analysis. Western blot identification of RBP4 in the various mouse lines is shown in panel B. Histological analysis were also performed. Tissue sections from RBP4+/+, ABCA4+/− mice (panel C), RBP4+/−, ABCA4+/− (panel D) and RBP4+/+, ABCA4+/+ (panel E) were analyzed by fluorescence microscopy. It is clear from this analysis that lipofuscin fluorophores (indicated by white arrows) are significantly reduced in mice with lower steady-state levels of RBP4 and retinol.
Figure 6:
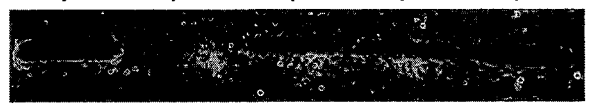
Figure 6:
Figure 6:
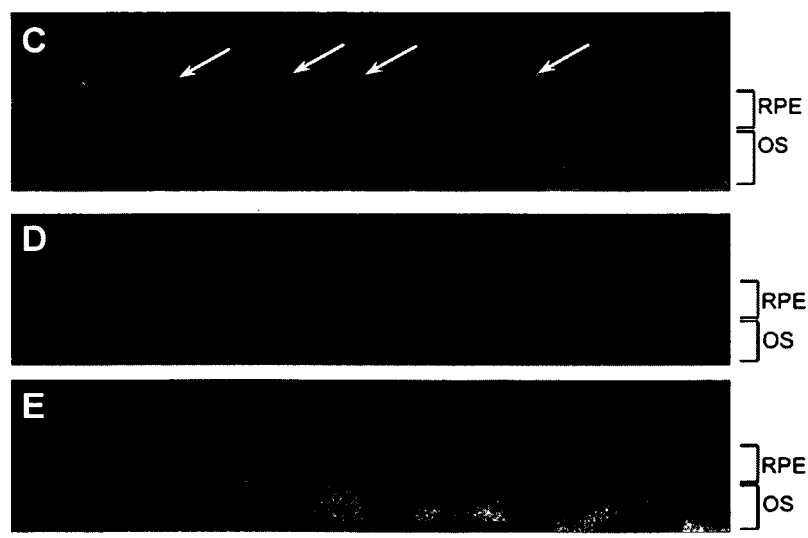
Figure 7:
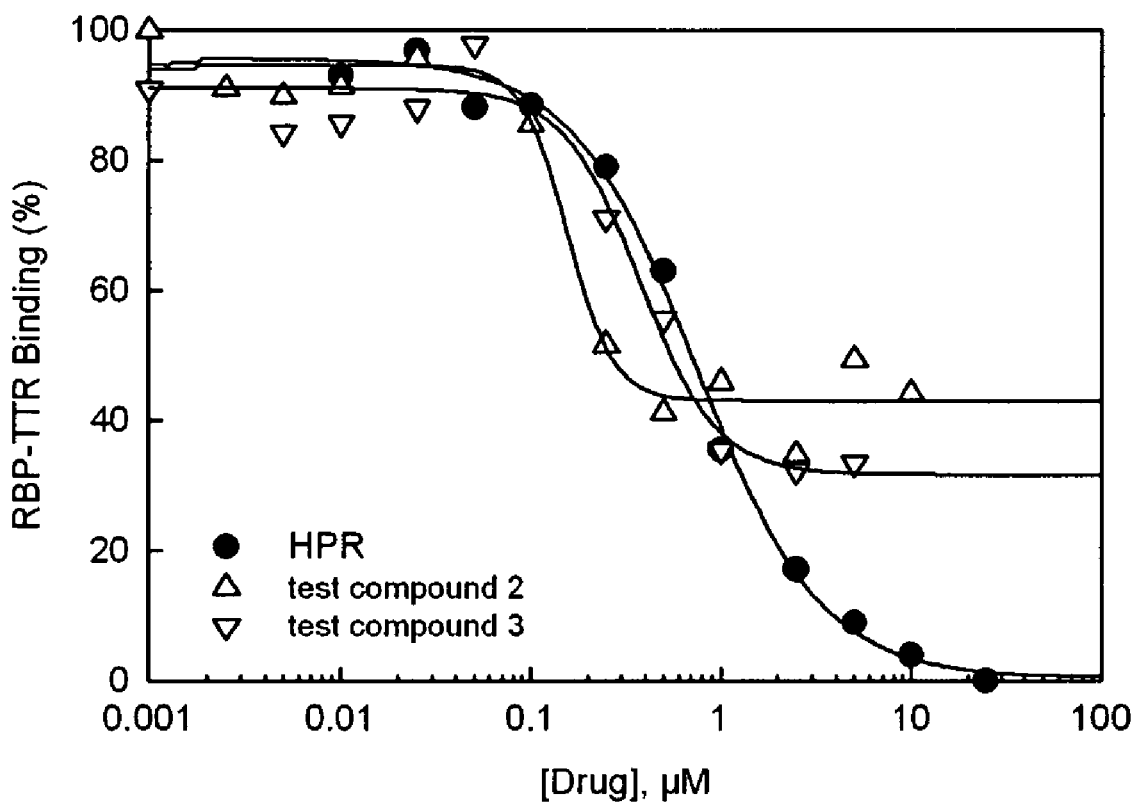
FIG. 7. Dose-response relationship of test compounds relative to fenretinide (HPR). The data show that the test compounds (test compound 2 having the chemical name 3-((2-tert-butyl-4-chlorophenoxy)methyl)cyclohexanecarboxylic acid and test compound 3 having the chemical name 3-((2-tert-butyl-4-chlorophenoxy)methyl)cyclopentanecarboxylic acid) are effective at disrupting RBP4-TTR interaction (IC$_{50}$=0.25-0.70 μM).
Figure 8:
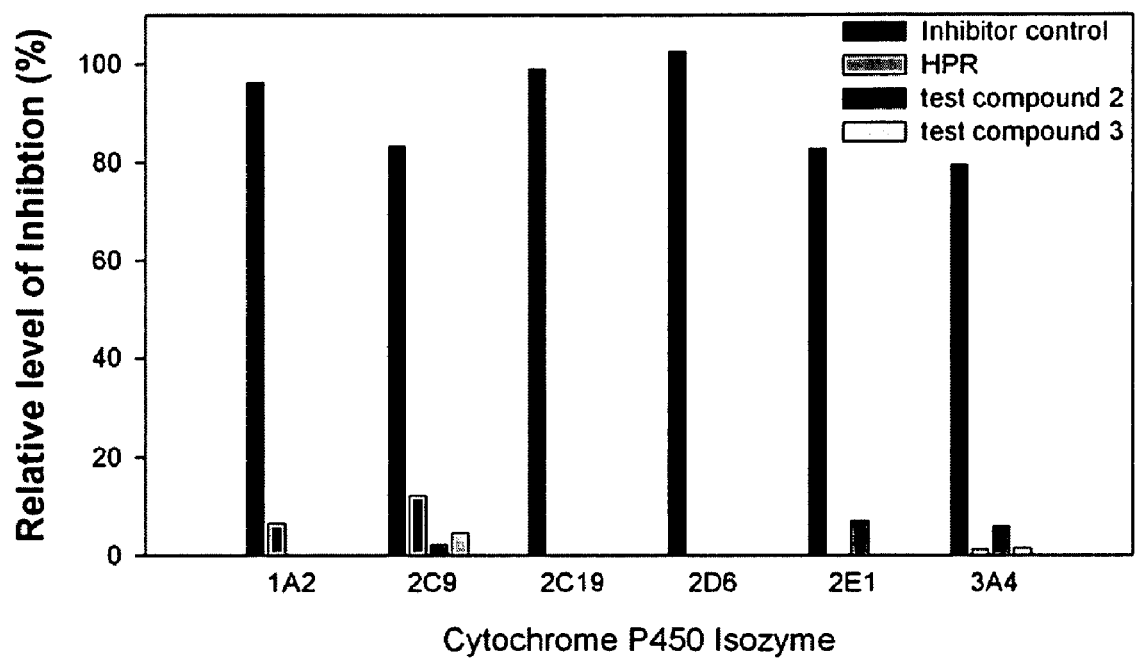
FIG. 8. Cytochrome P450 inhibition profile for test compounds and fenretinide (HPR). A panel of six cytochrome P450 isozymes were screened to explore potential toxicity associated with the test compounds (test compound 2 having the chemical name 3-((2-tert-butyl-4-chlorophenoxy)methyl)cyclohexanecarboxylic acid and test compound 3 having the chemical name 3-((2-tert-butyl-4-chlorophenoxy)methyl)cyclopentanecarboxylic acid) and HPR (present at 2 μM in the assays). The data show very little inhibition of the cytochrome P450 isozymes by the test compounds.

Exploration of a non-pharmacological means of reducing lipofuscin fluorophores in order to validate our therapeutic approach based upon reduction of RBP levels in a patient will be performed. In this study, RBP protein levels will be reduced through genetic manipulation. Two new lines of mice expressing heterozygous mutations in retinol binding protein (RBP4) are generated. The first line carries a heterozygous mutation only at the RBP locus (RBP+/−); the second line carries heterozygous mutations at both ABCA4 and RBP4 loci (RBP4+/−, ABCA4+/−). The RBP+/− mice will be wild type at the ABCA4 locus and, therefore, will not accumulate excessive amounts of A2E fluorophores. However, ABCA4+/− mice will accumulate A2E fluorophores at levels which are approximately 50% of that observed in ABCA4−/− (null homozygous) mice. At issue is whether the reduced expression of RBP in the RBP4+/−, ABCA4+/− mice will have an effect on the accumulation of toxic retinal fluorophores (e.g., A2E). FIG. 6 (panel A) illustrates a dramatic reduction (>50%) in serum retinol in RBP4+/−, ABCA4+/− mice compared to RBP4+/+, ABCA4−/− mice. The degree of retinol reduction in the RBP4+/−, ABCA4+/− mice is comparable to that observed in RBP4+/+, ABCA4−/− mice which have been administered HPR for a 28-day period. Immunoblot analysis of RBP4 levels in the sera of these mice is consistent with the retinol data (FIG. 6, panel B).

The levels of A2E and precursor fluorophores (A2PE and A2PE-$H_2$) in mice with genetically reduced expression of RBP4 (RBP4+/−, ABCA4+/−) are monitored monthly over a three month period and compared to the fluorophore levels in RBP4+/+, ABCA4+/− mice. Overall, the RBP4+/−, ABCA4+/− mice demonstrate a ~70% reduction in total fluorophore level relative to the levels present in ABCA4+/− mice (panels D and C, respectively). In fact, the measured fluorophore levels in the RBP4+/−, ABCA4+/− mice approach that observed in wild-type mice (compare panels D and E). These data validate RBP as a therapeutic target for reducing fluorophore levels in the eye. Further, these data will demonstrate that agents or methods that inhibit the transcription or translation of RBP in a patient also (a) reduce serum retinol levels in that patient, and (b) provide a therapeutic benefit in the retinol-related diseases described herein. Further, agents or methods that enhance the clearance of RBP in a patient will also produce such effects and benefits.

Example 21

Quantitation of Ocular Retinoids

ABCA4−/− mice were administered either ATRP (Control) or ATRP+ test compound daily for 20 days (n=3 mice/group). On the final day of dosing, a trace amount of [$^3$H]ATROL (0.32 µmol, 8 µCi) in 100 µl corn oil was administered to all animals. Eyes were enucleated 5 hours later. One eye from each animal was used for retinoid analysis and the other eye was used for analysis of A2E and related fluorophores as described in the methods. The data show a marked reduction in uptake of [$^3$H]ATROL in the animals treated with test compound [FIG. 9]. Analysis of each retinoid species showed that the precursor substrate for visual chromophore biosynthesis (ATRE) and the immediate precursor for A2E biosynthesis (AT-Ox) are significantly reduced.

Example 22

Effect of Test Compound in Reducing Total Fluorophore Levels

Figure 10:
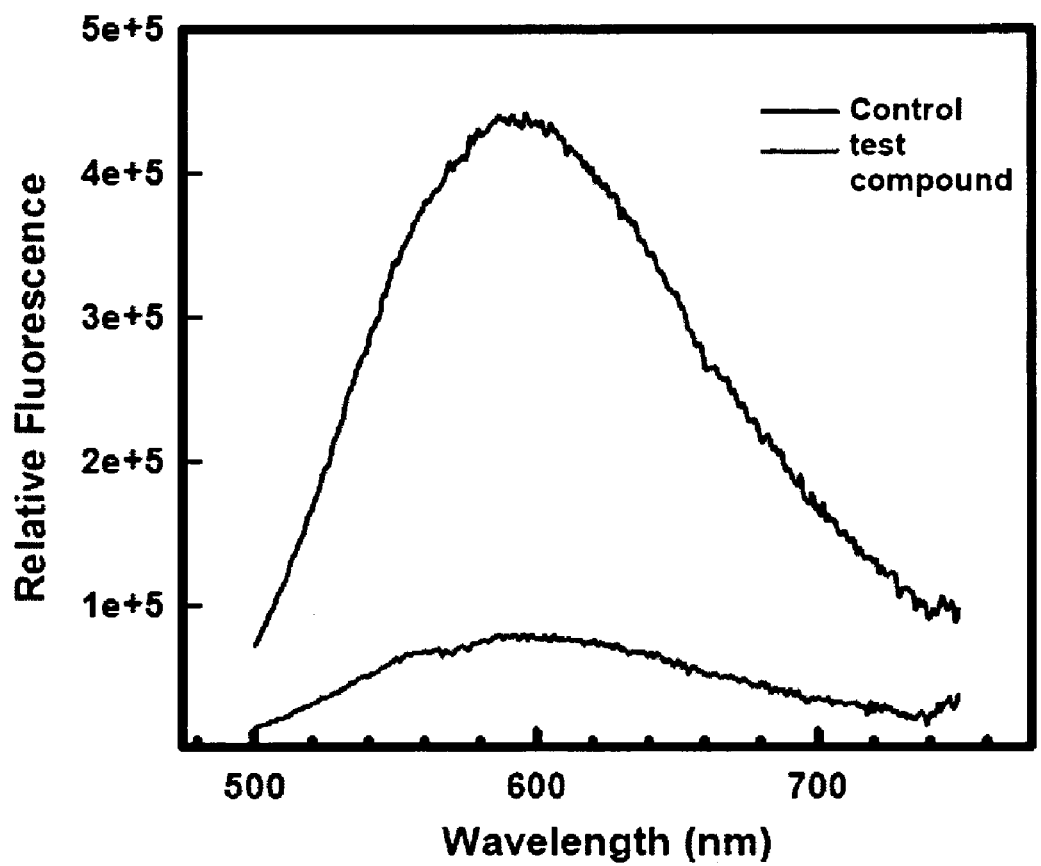
FIG. 10. Effect of test compound on reducing total fluorophore levels in ABCA4−/− mice. Mice were treated as described in FIG. 1 (above). At the end of the study, one eye from each animal was used to measure total fluorophore levels. Briefly, one whole eye was homogenized in 1 ml phosphate buffer saline (50 mM $Na_2HPO_4$, 150 mM NaCl, pH 7.8). Following homogenization, 1 ml methanol was added and the samples were mixed thoroughly. The mixtures were incubated at room temperature for 5 min and extracted twice with 2 ml hexane. The extracts were concentrated to ~400 µl for fluorescence measurements. Corrected fluorescence spectra were obtained using a Spex Fluorolog-3 spectrofluorimeter (Jobin Yvon Horiba, Edison, N.J.) operated in ratio mode. The samples were excited at 488 nm and emissions at 500-700 m were monitored. The data show a profound reduction on total fluorophore levels in mice treated with the test compound.

Effect of test compound on reducing total fluorophore levels in ABCA4−/− mice. Mice were treated as described in Example 13 above. At the end of the study, one eye from each animal was used to measure total fluorophore levels. Briefly, one whole eye was homogenized in 1 ml phosphate buffer saline (50 mM $Na_2HPO_4$, 150 mM NaCl, pH 7.8). Following homogenization, 1 ml methanol was added and the samples were mixed thoroughly. The mixtures were incubated at room temperature for 5 min and extracted twice with 2 ml hexane. The extracts were concentrated to ~400 µl for fluorescence measurements. Corrected fluorescence spectra were obtained using a Spex Fluorolog-3 spectrofluorimeter (Jobin Yvon Horiba, Edison, N.J.) operated in ratio mode. The samples were excited at 488 nm and emissions at 500-700 m were monitored. The data show a profound reduction on total fluorophore levels in mice treated with the test compound [FIG. 10].

Example 23

Effect of Test Compound on Reducing A2E and A2E Precursor

Figure 11:
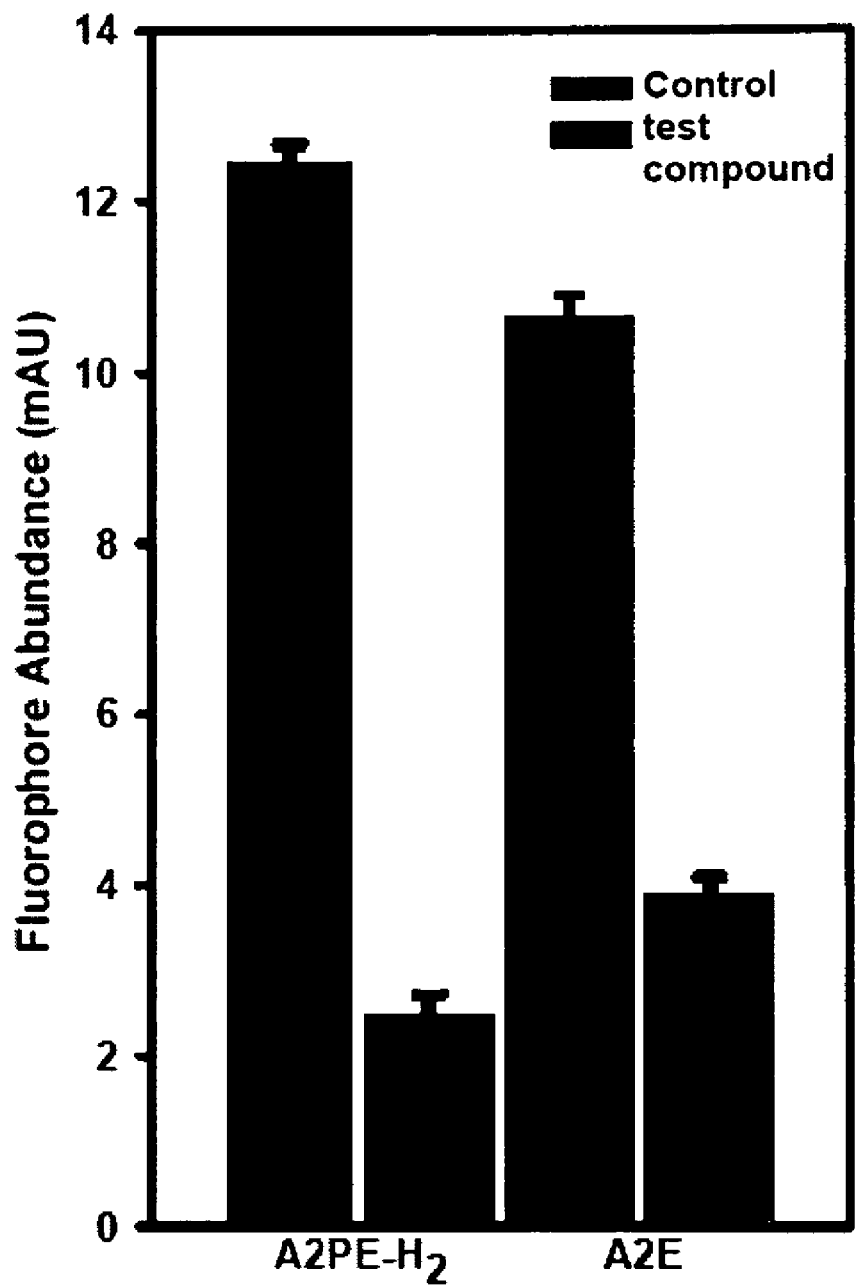
FIG. 11. Effect of test compound on reducing A2E and the A2E precursor, A2PE-H2 in ABCA4−/− mice. Mice were treated as described in FIG. 1 (above). At the end of the study, one eye from each animal was used to measure A2E and A2PE-H2. Briefly, one whole eye was homogenized in 1 ml phosphate buffer saline (50 mM $Na_2HPO_4$, 150 mM NaCl, pH 7.8). Following homogenization, 1 ml methanol was added and the samples were mixed thoroughly. The mixtures were incubated at room temperature for 5 min and extracted twice with 2 ml hexane. The solvent was evaporated under a stream of nitrogen and the sample residues were reconstituted in 200 µl isopropanol (IPA) for analysis by HPLC. Fluorophores were separated on a Zorbax RX-Sil 5-µm column (250×4.6-mm) equilibrated with a phospholipid moble phase (hexane:IPA:ethanol:25 mM phosphate buffer:acetic acid 485:376:100:37.5:0.275 v:v) at a flow rate of 1 ml/min. The data show a dramatic reduction in both A2E and its precursor in mice treated with test compound compared to vehicle-treated mice.

Mice were treated as described in Example 13 above. At the end of the study, one eye from each animal was used to measure A2E and A2PE-H2. Briefly, one whole eye was homogenized in 1 ml phosphate buffer saline (50 mM $Na_2HPO_4$, 150 mM NaCl, pH 7.8). Following homogenization, 1 ml methanol was added and the samples were mixed thoroughly. The mixtures were incubated at room temperature for 5 min and extracted twice with 2 ml hexane. The solvent was evaporated under a stream of nitrogen and the sample residues were reconstituted in 200 µl isopropanol (IPA) for analysis by HPLC. Fluorophores were separated on a Zorbax RX-Sil 5-µm column (250×4.6-mm) equilibrated with a phospholipid moble phase (hexane:IPA:ethanol:25 mM phosphate buffer:acetic acid 485:376:100:37.5:0.275 v:v) at a flow rate of 1 ml min. The data show a dramatic reduction in both A2E and its precursor in mice treated with test compound compared to vehicle-treated mice [FIG. 11].

Human Studies

Detection of Macular or Retinal Degeneration. Identification of abnormal blood vessels in the eye is done, for example with an angiogram. This identification helps determine which patients are candidates for the use of a candidate substance or other treatment method to hinder or prevent further vision loss. Angiograms are useful for follow-up of treatment as well as for future evaluation of any new vessel growth.

A fluorescein angiogram (fluorescein angiography, fluorescein angioscopy) is a technique for the visualization of choroidal and retinal circulation at the back of the eye. Fluorescein dye is injected intravenously followed by multiframe photography (angiography), opthalmoscopic evaluation (angioscopy), or by a Heidelberg retina angiograph (a confocal scanning laser system). Additionally, the retina is examined by OCT, a non-invasive way to obtain high-resolution cross-sectional images of the retina. Fluorescein angiograms are used in the evaluation of a wide range of retinal and choroidal diseases through the analysis of leakage or possible damage to the blood vessels that feed the retina. It has also been used to evaluate abnormalities of the optic nerve and iris by Berkow et al., *Am. J. Opthalmol.* 97:143-7 (1984).

Similarly, angiograms using indocyanine green are used for the visualization circulation at the back of the eye. Wherein fluorescein is more efficient for studying retinal circulation, indocyanine is better for observing the deeper choroidal blood vessel layer. The use of indocyanine angiography is helpful when neovascularization is not observed with fluorescein dye alone.

Appropriate human doses for compounds having the structure of Formula (I) will be determined using a standard dose escalation study.

Example 24

Clinical Trials for Testing the Efficacy of Test Compounds to Treat Macular Degeneration For pre-testing, all human patients will undergo a routine opthalmologic examination including fluorescein angiography, measurement of visual acuity, electrophysiologic parameters and biochemical and rheologic parameters. Inclusion criteria are as follows: visual acuity between 20/160 and 20/32 in at least one eye and signs of AMD such as drusen, areolar atrophy, pigment clumping, pigment epithelium detachment, or subretinal neovascularization. Patients that are pregnant or actively breast-feeding children are excluded from the study. Other exclusion criteria include previous vitrectomy or other AMD surgical intervention, severe scarring or severe concurrent ocular disease (uncontrolled glaucoma).

A group of patients diagnosed with macular degeneration, or who have progressive formations of A2E, lipofuscin, or drusen in their eyes are divided into a control group and an experimental group. A compound of Formula (I) or (II) is administered to the experimental group on a daily basis. A placebo is administered to the control group in the same regime as the test compound is administered to the experimental group.

A compound of Formula (I) or (II) or placebo is administered to a patient either orally or parenterally at amounts effective to inhibit the development or reoccurrence of macular degeneration. Effective dosage amounts are in the range of from about 1 to about 4000 mg/m² up to three times a day.

One method for measuring progression of macular degeneration in both control and experimental groups is the best corrected visual acuity as measured by Early Treatment Diabetic Retinopathy Study (ETDRS) charts (Lighthouse, Long Island, N.Y.) using line assessment and the forced choice method (Ferris et al *Am J Opthalmol,* 94:97-98 (1982)). Visual acuity is recorded in logMAR. The change of one line on the ETDRS chart is equivalent to 0.1 logMAR. Further typical methods for measuring progression of macular degeneration in both control and experimental groups include use of visual field examinations, including but not limited to a Humphrey visual field examination, microperimetry (using, e.g., Micro Perimeter MP-1 from NIDEK) and measuring/monitoring of autofluorescence of certain compounds in the eye of the patient.

Additional methods for measuring progression of macular degeneration in both control and experimental groups include taking fundus photographs, observing changes in autofluorescence over time using a Heidelberg retina angiograph (or alternatively, techniques described in M. Hammer, et al. *Opthalmologe* 2004 Apr. 7 [Epub ahead of patent]), and taking fluorescein angiograms at baseline, three, six, nine and twelve months at follow-up visits. Documentation of morphologic changes include changes in (a) drusen size, character, and distribution; (b) development and progression of choroidal neovascularization; (c) other interval fundus changes or abnormalities; (d) reading speed and/or reading acuity; (e) scotoma size; or (f) the size and number of the geographic atrophy lesions. In addition, Amsler Grid Test and color testing are optionally administered.

To assess statistically visual improvement during drug administration, examiners use the ETDRS (LogMAR) chart and a standardized refraction and visual acuity protocol. Evaluation of the mean ETDRS (LogMAR) best corrected visual acuity (BCVA) from baseline through the available post-treatment interval visits aids in determining statistical visual improvement.

To assess the ANOVA (analysis of variance between groups) between the control and experimental group, the mean changes in ETDRS (LogMAR) visual acuity from baseline through the available post-treatment interval visits are compared using two-group ANOVA with repeated measures analysis with unstructured covariance using SAS/STAT Software (SAS Institutes Inc, Cary, N.C.).

The serum retinol levels are assessed as follows: after acetonitrile precipitation of serum proteins, the concentrations of retinol are determined from the soluble phase by LC/MS. Alternatively, the serum retinol levels are assessed as described in Driskell et al., *J Chromatogr,* 1982, 231, 439-444 or Futterman et al, *Invest. Opthalmol Vis Sci,* 1975, 14, 125.

Toxicity evaluation after the commencement of the study includes check ups every three months during the subsequent year, every four months the year after and subsequently every six months. Plasma levels of the test compound and its metabolite, serum retinol and/or RBP are also assessed during these visits. The toxicity evaluation includes patients using a compound of Formula (I) or (II) as well as the patients in the control group.

Example 25

Activity of Non-retinoid Modulators on RBP-TTR and $CYP_{450}$

TABLE 1

| Compound of Formula (I) | Apparent $IC_{50}$ | CYP Inhibition |
|---|---|---|
| 5-(2-tert-butyl-4-chlorophenoxy)-N-(4-hydroxyphenyl)pentanamide, | 1 µM | ~50% |
| 7-(2-tert-butyl-4-chlorophenoxy)-N-(4-hydroxyphenyl)heptanamide | 1 µM | ~40% |
| 2-(4-(5-(2-tert-butyl-4-chlorophenoxy)pentanamido)phenyl)acetic acid | 1 µM | <10% |
| 3-((2-tert-butyl-4-chlorophenoxy)methyl)-N-(4-hydroxyphenyl)cyclopentanecarboxamide | 5 µM | <10% |

TABLE 1-continued

| Compound of Formula (I) | Apparent IC$_{50}$ | CYP Inhibition |
|---|---|---|
| 4-(5-(2-tert-butyl-4-chlorophenoxy)pentanamido)benzoic acid | 5 μM | <10% |
| 4-(3-((2-tert-butyl-4-chlorophenoxy)methyl)cyclopentanamido)benzoic acid | 5 μM | <10% |
| 5-(2-tert-butyl-4-chlorophenoxy)pentanoic acid | 0.1 μM | ≦10% |
| 4-(2-tert-butyl-4-chlorophenoxy)butanoic acid | 1 μM | ~15% |
| 2-(3-((2-tert-butyl-4-chlorophenoxy)methyl)cyclopentyl)acetic acid | NT | NT |
| 7-(2-tert-butyl-4-chlorophenoxy)heptanoic acid | 0.5 μM | ~15% |
| 4-(5-(2-tert-butyl-4-chlorophenoxy)pentanamido)benzamide | NT | NT |
| 3-((2-tert-butyl-4-chlorophenoxy)methyl)cyclohexanecarboxylic acid | 0.16 μM | <10% |
| 3-((2-tert-butyl-4-chlorophenoxy)methyl)cyclopentanecarboxylic acid | 0.4 μM | <10% |
| 3-((2-tert-butyl-4-chlorophenylamino)methyl)cyclopentanamide | NT | NT |
| 5-(2-tert-butyl-4-chlorophenylthio)pentanoic acid | NT | NT |

NT: Not Tested

Table 1 shows IC$_{50}$ values and cytochrome P$_{450}$ inhibition profiles of representative compounds having the structure of Formula (I) and (II).

Example 26

Testing for the Efficacy of Compounds of Formula (I) or (II) to Reduce A2E Production The same protocol design, including pre-testing, administration, dosing and toxicity evaluation protocols, that are described in Example 24 are also used to test for the efficacy of compounds of Formula (I) or (II) in reducing or otherwise limiting the production of A2E in the eye of a patient.

Methods for measuring or monitoring formation of A2E include the measuring/monitoring of autofluorescence of certain compounds in the eye of the patient, the use of visual acuity and visual field examinations (including, by way of example, microperimetry), reading speed and/or reading acuity examinations, measurements on the size and number of scotoma and/or geographic atrophic lesions, as described in Example 23. The statistical analyses described in Example 23 is employed.

Example 27

Testing for the Efficacy of Compounds of Formula (I) or (II) to Reduce Lipofuscin Production The same protocol design, including pre-testing, administration, dosing and toxicity evaluation protocols, that are described in Example 24 are also used to test for the efficacy of compounds of Formula (I) or (II) in reducing or otherwise limiting the production of lipofuscin in the eye of a patient. The statistical analyses described in Example 24 are employed.

Tests that are used as surrogate markers for the efficacy of a particular treatment include the use of visual acuity and visual field examinations (including, by way of example, microperimetry), reading speed and/or reading acuity examinations, measurements on the size and number of scotoma and/or geographic atrophic lesions, and the measuring/monitoring of autofluorescence of certain compounds in the eye of the patient, as described in Example 24.

Example 28

Testing for the Efficacy of Compounds of Formula (I) or (II) to Reduce Drusen Production The same protocol design, including pre-testing, administration, dosing and toxicity evaluation protocols, that are described in Example 24 are also used to test for the efficacy of compounds of Formula (I) or (II) in reducing or otherwise limiting the production or formation of drusen in the eye of a patient. The statistical analyses described in Example 24 are employed.

Methods for measuring progressive formations of drusen in both control and experimental groups include taking fundus photographs and fluorescein angiograms at baseline, three, six, nine and twelve months at follow-up visits. Documentation of morphologic changes include changes in (a) drusen size, character, and distribution (b) development and progression of choroidal neovascularization and (c) other interval fundus changes or abnormalities. Other tests that are used as surrogate markers for the efficacy of a particular treatment include the use of visual acuity and visual field examinations (including, by way of example, microperimetry), reading speed and/or reading acuity examinations, measurements on the size and number of scotoma and/or geographic atrophic lesions, and the measuring/monitoring of autofluorescence of certain compounds in the eye of the patient, as described in Example 23.

Example 29

Genetic Testing for Macular Dystrophies

Defects in the human ABCA4 gene are thought to be associated with five distinct retinal phenotypes including Stargardt Disease, cone-rod dystrophy, age-related macular degeneration (both dry form and wet form) and retinitis pigmentosa. See e.g., Allikmets et al., Science, 277:1805-07 (1997); Lewis et al., Am. J. Hum. Genet., 64:422-34 (1999); Stone et al., Nature Genetics, 20:328-29 (1998); Allikmets, Am. J. Hum. Gen., 67:793-799 (2000); Klevering, et al, Opthalmology, 111:546-553 (2004). In addition, an autosomal dominant form of Stargardt Disease is caused by mutations in the ELOV4 gene. See Karan, et al., Proc. Natl. Acad. Sci. (2005). Patients are diagnosed as having Stargardt Disease by any of the following examples of assays:

A direct-sequencing mutation detection strategy which involves sequencing all exons and flanking intron regions of ABCA4 or ELOV4 for sequence mutation(s);
Genomic Southern analysis;
Microarray assays that include all known ABCA4 or ELOV4 variants; and
Analysis by liquid chromatography tandem mass spectrometry coupled with immunocytochemical analysis using antibodies and Western analysis.

Fundus photographs, fluorescein angiograms, and scanning laser opthalmoscope imaging along with the history of the patient and his or her family are methods to anticipate and/or confirm diagnosis.

Example 30

Formulations

Example 30a

Oral Composition

To prepare a pharmaceutical composition for oral delivery, 100 mg of a compound of any of Formula (I), or Formula (II) is mixed with 750 mg of starch. The mixture is incorporated into an oral dosage unit for, such as a hard gelatin capsule, which is suitable for oral administration.

Example 30b

Parenteral Composition

To prepare a parenteral pharmaceutical composition suitable for administration by injection, 100 mg of a water-soluble salt of a compound of any of Formula (I), or Formula (II) is dissolved in DMSO and then mixed with 10 mL of 0.9% sterile saline. The mixture is incorporated into a dosage unit form suitable for administration by injection.

Example 30c

Sublingual (Hard Lozenge) Composition

To prepare a pharmaceutical composition for buccal delivery, such as a hard lozenge, mix 100 mg of a compound of any of Formula (I), or Formula (II) is mixed with 420 mg of powdered sugar, 1.6 mL of light corn syrup, 2.4 mL distilled water, and 0.42 mL mint extract. The mixture is gently blended and poured into a mold to form a lozenge suitable for buccal administration.

Example 30d

Inhalation Composition

To prepare a pharmaceutical composition for inhalation delivery, 20 mg of a compound of any of Formula (I), or Formula (II) is mixed with 50 mg of anhydrous citric acid and 100 mL of 0.9% sodium chloride solution. The mixture is incorporated into an inhalation delivery unit, such as a nebulizer, which is suitable for inhalation administration.

Example 30e

Rectal Gel Composition

To prepare a pharmaceutical composition for rectal delivery, 100 mg of a compound of any of Formula (I), or Formula (II) is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 30f

Topical Gel Composition

To prepare a pharmaceutical topical gel composition, 100 mg of a compound of any of Formula (I), or Formula (II) is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topic administration.

Example 30g

Ophthalmic Solution Composition

To prepare a pharmaceutical opthalmic solution composition, 100 mg of a compound of any of Formula (I), or Formula (II) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

The examples and embodiments described herein are for illustrative purposes only and various modifications or changes suggested are to be included within the spirit and purview of this application and scope of the appended claims.

What is claimed is:

1. A pharmaceutical composition comprising a compound of Formula (I):

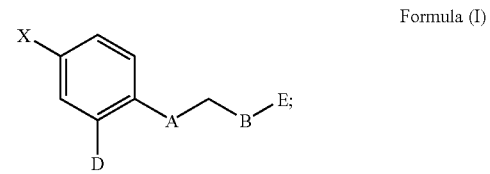

Formula (I)

wherein:
A is O, NH, or S;
B is a bond, —($C_2$-$C_7$)alkyl, —($C_2$-$C_7$)alkenyl, —($C_3$-$C_8$)cycloalkyl, —($C_3$-$C_8$)heterocycloalkyl, —($C_3$-$C_8$)cycloalkenyl, or —($C_3$-$C_8$)heterocycloalkenyl;
D is isopropyl, isobutyl, sec-butyl, tert-butyl, cyclopropyl, cyclobutyl, cyclopentyl, methylenecyclopropyl, methylenecyclobutyl, or methylenecyclopentyl;
E is (C=O)—OR, —O—(C=O)—R, —(C=O)—R, —OR, a carboxylic acid bioisostere, —(C=O)—$NR^1R$, $NR^1$—(C=O)—R, —($C_1$-$C_7$)alkyl-(C=O)—OR, or —($C_1$-$C_7$)alkyl-(C=O)—$NR^1R$;

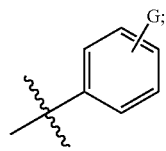

R is H or

G is —OR¹, —(C₁-C₆)alkyl, —(C₁-C₆)alkyl-OR¹, halogen, —CO₂R¹, —(C₁-C₆)alkyl-CO₂R¹, NHR¹, —(C₁-C₆)alkyl-NHR¹, —(C=O)NHR¹, —(C₁-C₆)alkyl-(C=O)NHR¹, —NHR¹(C=O)R¹, or —(C₁-C₆)alkyl-NHR¹(C=O)R¹;

R¹ is H or (C₁-C₆)alkyl; and

X is a halogen;

or a pharmaceutically acceptable prodrug, salt thereof; and a pharmaceutically acceptable excipient.

2. The pharmaceutical composition of claim 1 having the structure of Formula (II):

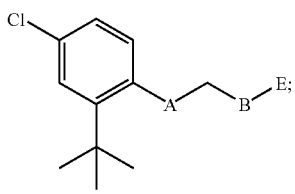

Formula (II)

wherein:

A is O, NH, or S;

B is —(C₂-C₇)alkyl, —(C₂-C₇)alkenyl, —(C₃-C₈)cycloalkyl, —(C₃-C₈)heterocycloalkyl, —(C₃-C₈)cycloalkenyl, or —(C₃-C₈)heterocycloalkenyl;

E is (C=O)—OR, —O—(C=O)—R, —(C=O)—R, —OR, a carboxylic acid bioisostere, —(C=O)—NR¹R, NR¹—(C=O)—R, —(C₁-C₇)alkyl-(C=O)—OR, or —(C₁-C₇)alkyl-(C=O)—NR¹R;

R is H or

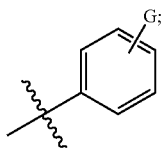

G is —OR¹, —(C₁-C₆)alkyl, —(C₁-C₆)alkyl-OR¹, halogen, —CO₂R¹, —(C₁-C₆)alkyl-CO₂R¹, NHR¹, —(C₁-C₆)alkyl-NHR¹, —(C=O)NHR¹, —(C₁-C₆)alkyl-(C=O)NHR¹, —NHR¹(C=O)R¹, or —(C₁-C₆)alkyl-NHR¹(C=O)R¹;

R¹ is H or (C₁-C₆)alkyl; and or a pharmaceutically acceptable prodrug, salt thereof.

3. The pharmaceutical composition of claim 2 wherein A is O.

4. The pharmaceutical composition of claim 3 wherein B is —(CH₂)ₙ and n is 2-6, or B is —(C₃-C₈)cycloalkyl.

5. The pharmaceutical composition of claim 4 wherein E is (C=O)—OR, a carboxylic acid bioisostere, —(C=O)—NR¹R, —(C₁-C₇)alkyl-(C=O)—OR, or —(C₁-C₇)alkyl-(C=O)—NR¹R.

6. The pharmaceutical composition of claim 5 wherein R is

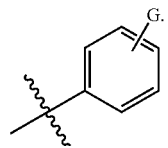

7. The pharmaceutical composition of claim 4 wherein E is (C=O)—OR.

8. The pharmaceutical composition of claim 7 wherein R is H.

9. The pharmaceutical composition of claim 1 selected from the group consisting of: 5-(2-tert-butyl-4-chlorophenoxy)-N-(4-hydroxyphenyl)pentanamide, 7-(2-tert-butyl-4-chlorophenoxy)-N-(4-hydroxyphenyl)heptanamide, 4-(5-(2-tert-butyl-4-chlorophenoxy)pentanamido)benzoic acid, 4-(3-((2-tert-butyl-4-chlorophenoxy)methyl)cyclopentanamido)benzoic acid, 5-(2-tert-butyl-4-chlorophenoxy)pentanoic acid, 4-(2-tert-butyl-4-chlorophenoxy)butanoic acid, 2-(3-((2-tert-butyl-4-chlorophenoxy)methyl)cyclopentyl)acetic acid, 7-(2-tert-butyl-4-chlorophenoxy)heptanoic acid, 4-(5-(2-tert-butyl-4-chlorophenoxy)pentanamido)benzamide, 3-((2-tert-butyl-4-chlorophenoxy)methyl)cyclohexanecarboxylic acid, 3-((2-tert-butyl-4-chlorophenoxy)methyl)cyclopentanecarboxylic acid, 3-((2-tert-butyl-4-chlorophenylamino)methyl)cyclopentanamide, 4-(3-((2-tert-butyl-4-chlorophenoxy)methyl)cyclopentanecarboxamido)benzoic acid, and 5-(2-tert-butyl-4-chlorophenylthio)pentanoic acid 10. The pharmaceutical composition of claim 1 wherein the pharmaceutical composition is formulated for oral administration.

* * * * *